US007277874B2

(12) United States Patent
Sumner, II et al.

(10) Patent No.: US 7,277,874 B2
(45) Date of Patent: Oct. 2, 2007

(54) COMPUTER ARCHITECTURE AND PROCESS OF PATIENT GENERATION, EVOLUTION, AND SIMULATION USING KNOWLEDGE BASE SCRIPTING

(75) Inventors: Walton Sumner, II, St. Louis, MO (US); Michael D. Hagen, Lexington, KY (US)

(73) Assignee: American Board of Family Medicine, Inc., Lexington, KY (US)

( * ) Notice: Subject to any disclaimer, the term of this patent is extended or adjusted under 35 U.S.C. 154(b) by 0 days.

(21) Appl. No.: 11/203,230

(22) Filed: Aug. 15, 2005

(65) Prior Publication Data

US 2005/0289092 A1    Dec. 29, 2005

Related U.S. Application Data

(60) Continuation of application No. 10/265,599, filed on Oct. 8, 2002, now Pat. No. 7,024,399, which is a division of application No. 09/521,242, filed on Apr. 5, 2000, now Pat. No. 7,107,253.

(60) Provisional application No. 60/127,850, filed on Apr. 5, 1999.

(51) Int. Cl.
  *G06F 17/00*  (2006.01)
  *G06N 5/00*  (2006.01)
(52) U.S. Cl. ...................................................... 706/45
(58) Field of Classification Search .................... 706/45
  See application file for complete search history.

(56) References Cited

U.S. PATENT DOCUMENTS

| 3,008,000 A | 11/1961 | Morchand |
| 3,484,950 A | 12/1969 | Serrell et al. |
| 3,537,190 A | 11/1970 | Serrell et al. |
| 4,360,345 A | 11/1982 | Hon |
| 4,547,161 A | 10/1985 | Manning |
| 4,797,104 A | 1/1989 | Laerdal et al. |

(Continued)

FOREIGN PATENT DOCUMENTS

WO          WO98/02836      *    1/1998

(Continued)

OTHER PUBLICATIONS

Tanha et al, "An Intelligent Monitoring System for Patient Health Care", IEEE/EMBS Oct. 30-Nov. 2, 1997.*

(Continued)

*Primary Examiner*—Anthony Knight
*Assistant Examiner*—Michael B. Holmes
(74) *Attorney, Agent, or Firm*—Irah H. Donner; Wilmer Cutler Pickering Hale and Dorr LLP

(57) ABSTRACT

A method and system for patient generation and evolution for a computer-based testing system and/or expert system. One or more belief networks, which describe parallel health state networks are accessed by a user or a computer. A knowledge base, at least in part, is scripted from the one or more belief networks by the computer. A model patient at least in part, is instantiated by the computer from the scripted knowledge base. Optionally, the model patient is evolved by the computer in accordance with the parallel health state networks and responsive to a received course of action.

21 Claims, 27 Drawing Sheets

U.S. PATENT DOCUMENTS

| | | | |
|---|---|---|---|
| 4,872,122 | A | 10/1989 | Altschuler et al. |
| 4,978,305 | A | 12/1990 | Kraft |
| 5,002,491 | A | 3/1991 | Abrahamson et al. |
| 5,005,143 | A | 4/1991 | Altschuler et al. |
| 5,011,413 | A | 4/1991 | Ferris et al. |
| 5,033,969 | A | 7/1991 | Kamimura et al. |
| 5,059,127 | A | 10/1991 | Lewis et al. |
| 5,103,408 | A | 4/1992 | Greenberg et al. |
| 5,133,046 | A | 7/1992 | Kaplan et al. |
| 5,141,439 | A | 8/1992 | Cousins |
| 5,163,131 | A | 11/1992 | Row et al. |
| 5,180,309 | A | 1/1993 | Egnor |
| 5,195,033 | A | 3/1993 | Samph et al. |
| 5,204,813 | A | 4/1993 | Samph et al. |
| 5,211,564 | A | 5/1993 | Martinez et al. |
| 5,219,291 | A | 6/1993 | Fong et al. |
| 5,240,419 | A | 8/1993 | deGyarfas |
| 5,574,828 | A | 11/1996 | Hayward et al. |
| 5,594,638 | A | 1/1997 | Iliff |
| 5,644,686 | A | 7/1997 | Hekmatpour |
| 5,657,255 | A | 8/1997 | Fink et al. |
| 5,660,176 | A | 8/1997 | Iliff |
| 5,680,590 | A | 10/1997 | Parti |
| 5,687,716 | A | 11/1997 | Kaufmann et al. |
| 5,764,923 | A | 6/1998 | Tallman et al. |
| 5,853,292 | A | 12/1998 | Eggert et al. |
| 5,935,060 | A * | 8/1999 | Iliff ............................ 600/300 |
| 5,956,501 | A | 9/1999 | Brown |
| 6,021,404 | A | 2/2000 | Moukheibir |
| 6,049,794 | A | 4/2000 | Jacobs et al. |
| 6,234,964 | B1 * | 5/2001 | Iliff ............................ 600/300 |
| 6,246,975 | B1 * | 6/2001 | Rivonelli et al. ............. 703/11 |
| 6,260,035 | B1 | 7/2001 | Horvitz et al. |
| 6,262,730 | B1 | 7/2001 | Horvitz et al. |
| 6,292,771 | B1 | 9/2001 | Haug et al. |
| 6,556,977 | B1 | 4/2003 | Lapointe et al. |
| 6,692,258 | B1 | 2/2004 | Kurzweil et al. |
| 2001/0001852 | A1 | 5/2001 | Rovinelli et al. |
| 2001/0053875 | A1 | 12/2001 | Iliff |

FOREIGN PATENT DOCUMENTS

| | | |
|---|---|---|
| WO | WO-00/65523 | 11/2000 |
| WO | WO-02/05205 | 1/2002 |

OTHER PUBLICATIONS

Krol et al, "Object-Oriented Model of a Health Care System", IEEE Symposium on Computer-Based Medical System, Jun. 1998.*

Altman, Russ B. et al. Aug. 1995. "A Programming Course in Bioinformatics for Computer and Information Science Students." Knowledge Systems Laboratory Report. KSL-95-64.

Anjewierden, Anjo et al. 1992. "Shelly -Computer Aided Knowledge Engineering," Knowledge Acquisition. pp. 109-125.

Ash, David et al. Jan. 1992. "Action-Based Fault Hiearchies for Real-Time Response." Knowledge Systems Laboratory Report. KSL-92-05.

Badler, N.I. et al. Mar. 27-29, 1995, "MediSim; Simulated Medical Corpsmen and Casualties for Medical Forces Planning and Training." Proceedings of the National Forum on Military Telemedicine Online Today: Research, Practice and Opportunities. pp. 21-28.

Balla, J.I. et al. Mar. 4, 1989. "Obstacles to Acceptance of Clinical Decision Analysis." B.M.J. vol. 298, pp. 579-582.

Barnett, G. Octo et al. 1983. "Computers in Medical Education Present and Future." Proceedings of the Seventh Annual Symposium on Computer Applications in Medical Care, Washington, DC: IEEE Press. pp. 11-13.

Barnett, G. Octo. 1974. "The Use of a Computer-Based System to Teach Clinical Problem Solving." Computers in Biomedical Research. New York: Academic Press. vol. 4, pp. 301-319.

Barroso, Luiz Andre et al. Feb. 1995. "RPM: A Rapid Prototyping Engine for Multiprocessor Systems." Computer. pp. 26-34.

Baud, PhD, Robert H. et al. 1996. "Knowledge Sources for Natural Language Processing."pp. 70-74.

Becker, MD. W.J. Oct. 1994. "Canadian Specialty Examinations: Considerations for the Future."Annals RCPSC. vol. 27. No. 7. pp. 409-412.

Bellazzi et al. Jun. 1992. "GAMEES II: An Environment For Building Probabilistic Expert Systems, Based on Arrays of Bayosian Belief Networks." IEEE Symposium on Computer-Based Medical Systems.

Bergeron, MD, Bryan. 1991. "Illiad; A Diagnostic Consultant and Patient Simulator." MD Computing. vol. 8, No. 1, pp. 46-53.

Berman, Lewis et al, 1993. "Automated Integration of External Databases: A Knowledge-Based Approach to Enhancing Rule-Based Expert Systems." Computers and Biomedical Research. 26, pp. 230-241.

Bhansali, Sanjay et al. Jan. 1992. "Synthesis of UNIX Programs Using Dorivational Analogy."Knowledge Systems Laboratory Report. KSL-92-02.

Bioder, T. et al. Sep. 10-13, 1995. "A Computer Based Interactive Learning and Reference Tool for Transthoracic Echocardiographic Images," Computer in Cardiology 1995, pp. 617-620.

Bishop, M.D. 1992. "The Unitied Medical Language System (UMLS)." Computing. vol. 9, No. 4, pp. 221-225.

Bishop, PhD, Charles W. et al. 1992. "Representing Medical Knowledge: Reconciling the Present or Creating the Future?" M.D. Computing. vol. 9, No. 4, pp. 218-220.

Bishop, PhD, Charles W. Oct.-Dec. Supplement 1991. "Alternate Approaches to a UMLS," Medical Decision Making. vol. 11, No. 4, pp. S99-S102.

Board of Directors of the American Medical Informatics Association. Jan./Feb. 1994. "Standards for Medical Identifiers. Codes and Messages Needed to Create an Efficient Computer-stored Medical Record." Journal of the American Medical InformaticsAssociation. vol. 1, No. 1, pp. 1-7.

Born, Andreas et al. "A Blackborad-Approach to a Knowledge Based Tutoring System for Linear Programming." Institute for Informatik/WWZ. Switzerland.

Boxer, Aaron. 1995. "Where Buses Cannot Go." IEEE Spectrum, pp. 41-45.

Bradshaw, Jeffery M. et al. 1991. "Knowledge Acquisition Techniques for Decision Analysis Using AXOTL and AOUINAS," Knowledge Acquisition. 3, pp. 49-77.

Breuker. Joost et al. 1989. "Models of Expertise in Knowledge Acquisition." Topics in Expert Design. pp. 265-295.

Brinkely, Joel, May 29, 1994. "The Furor Over Data on Doctors: You Bet Your Life. Do You Know the Odds?" The New York Times.

Buekens, F, et al. 1993, "The Explanatory Role of Events in Casual and Temporal Reasoning in Medicine." Methods of Information in Medicine. 32, pp. 274-278.

Campbell, James R. et al. "Phase II Evaluation of Clinical Coding Schemes: Completeness, Taxonomy, Mapping, Definitions and Clarity." Dept. of Internal Medicine, University of Nebraska.

Campbell, Keith E. et al. Oct. 1991. "Creation of a Systematic Domain for Medical Care: The Need for a Comprehensive Patient-Description Vocabulary." Knowledge Systems Laboratory Report. KSL-91-60.

Campbell. MD. Keith E. et al. 1996. "Galapagos: Computer Based Support for Evolution of a Convergent Medical Terminology." AMIA, Inc. pp. 269-273.

Cason, PhD. Gerlod J. Dec. 1980. "Test Results Depend on Response Format." Office of Educational Development, University of Arkansas for Medical Sciences, vol. 6, No. 8.

Cawley, M.G. et al. 1991. "Data Representation for Subsequent Image Interpretation." Med. Inform. vol. 16, No. 2, pp. 125-136.

Chan, Tak-Wai. "Learning Companion Systems, Social Learning Systems and Intellignet Virtual Classrooms." Dept. of Computer Science and Information Engineering, National Central University, Taiwan.

Chandrasekaran, B. Fall 1986. "Generic Tasks in Knowledge-Based Reasoning: High-Level Building Blocks for Expert System Design." IEEE Expert.

Chang, et al. Jun. 1994. "A Knowledge Engineering System For MEDAS." IEEE Seventh Symposium on Computer-Based Medical Systems.

Charniak, Eugene. 1991. "Bayesian Networks without Tears." AI Magazine, pp. 50-63.

Chin, Homer L. et al. Oct.-Nov. 1989. "Caso-Based Tutoring from a Medical Knowledge Base." Computer Methods and Programs in Biomedicine. Netherlands. vol. 30, No. 2-3, pp. 185-198.

Christonsen, Caryn et al. Sep. Supplement 1991. "Framing Bras Among Expert and Novice Physicians." Academic Medicine. vol. 66, No. 9, pp. S76-S78.

Chung, Jaesam. "An Advance Toward Instructional Management: Prescriptive Knowledge Base of Learner Control." Indiana University. pp. 1-9.

Cimino, J.J. 1995. "Review Paper: Coding Systems in Health Care." Methods of Information in Medicine. 35, pp. 273-284.

Cimino, MD, James J. et al. Jan./Feb. 1994. "Knowledge Based Approaches to the Maintenace of a Large Controlled Medical Terminology." Journal of the American Medical Informatics Association. vol. 1, No. 1, pp. 35-50.

Clauser, Brian E. et al. Winter 1995. "Scoring a Performance Based Assessment by Modeling the Judgements of Experts." Journal of Educational Measurement. vol. 32, No. 4. pp. 397-415.

Clyman, MD, Stephen G. et al, 1990. "Status Report on the NBME's Computer-Based Testing." Academic Medicine. vol. 65, No. 4, pp. 235-241.

Combs, David M. et al. Aug. 1988. "From Expert Models to Expert Systems: Yranslation of an Intermediate Knowledge Representation." Knowledge Systems Laboratory Report. KSL-88-58.

Cook, John et al. "COLERIDGE: Composition Learning Environment for Reflection About Intentions and Dialogue Goals in Education".

Cooper, Gregory F. 1986. "A Diagnostic Method that Uses Casual Knowledge and Linear Programming in the Application of Bayes' Formula." Computer Methods and Programs in Biomedicine, vol. 22. pp. 223-237.

Culhane, Charles. "Streamlining for Managed Care." American Medical Newsletter.

David, Jean-Marc et al. 1993. "Second Generation Expert Systems: A Step Forward in Knowledge Engineering." Springer Verlag. New York, NY. pp. 3-23.

Davis Randall. Spring 1982. "Expert Systems: Where Are We? And Where Do We Go From Here?" The AI Magazine. vol. 3, pp. 3-22.

Dawes, Robyn M. et al. Mar. 31, 1989. "Clinical Versus Actuarial Judgment." Science. vol. 243, pp. 1668-1674.

Day, Susan C. et al. Sep. Supplement 1990. "The Validity of an Essay Test of Clinical Judgment." Academic Medicine. vol. 65, No. 9, pp. 539-540.

Diamond, MD, George A. et al. Jun. 14, 1979. "Analysis of Probability As An Aid in the Clinical Diagnosis of Coronary Artery Disease." The New England Journal of Medicine. vol. 300, No. 24, pp. 1350-1358.

Dolan, MD, James G. et al. Jan.-Mar. 1989. "The Analytical Hierarchy Process in Medical Decision Making: A Tutorial." Medical Decison Making. vol. 9, No. 1, pp. 40-50.

Doughly, Ken. Sep. 1993. "Auditing the Disaster Recovery Plan." EDPACS: The EDP Audit, Control, and Security Newsletter. vol. 21, No. 3.

Egar, John W. et al. Nov. 1992, "Graph-Grammar Productions for the Modeling of Medical Dilemmas." Knowledge Systems Laboratory Report. KSL-92-15.

Elstein, Arthur S. et al. Mar. 1990. "Medical Problem Solving: A Ten Year Retrospective." Evaluation & Health Professions. vol. 13, No. 1, pp. 5-36.

Elstein, PhD, Arthur S. et al. 1993. "Beyond Multiple Choice Questions an Essays: The Need for a New Way to Assess Clinical Competence." Academic Medicine. vol. 58, No. 4, pp. 244-249.

Ericcson, K.A. et al. 1984. "Protocol Analysis." Cambridge, MA: MIT Press.

Eriksson, Henrik et al. Apr. 1993. "Task Modeling with Reusable Problem-Solving Methods." Knowledge Systems Laboratory Report. KSL-92-43.

Eriksson. Henrik et al. May 1993. "Conceptual Models for Automatic Generation of Knowledge-Acquisition Tools." Knowledge Systems Laboratory Report. KSL-92-28.

Eriksson, Henrik et al. Nov. 1994. "Generation of Knowledge Acquistion Tools from Domain Ontologies." Knowledge Systems Laboratory Report. KSL-93-56.

Eriksson, Henrik, 1992. "Metatool Support for Custom-tailored, Domain-oriented Knowledge Acquistion." Knowledge Acquisition. vol. 4, pp. 445-476.

Eskenasi, Avram et al. May 1993. "Incorporating Sludent Models in Adaptive Testing Systems." Educational & Training Technology International. vol. 30, No. 2, pp. 135-143.

European Search Report from European Application No. 00921673.0 mailed Jun. 11, 2003.

Farr, Brad R. et al. 1992. "Represontation of Proforonces in Decision-Support Systems." Computers and Biomedical Research. 25 pp. 324-335.

Felciano, Ramon M. et al. Nov. 1994. "Multimedia Clinical Simulation Based on Patient Records: Authoring, User Interface, Pedagogy." Knowledge Systems Laboratory Report. KSL-94-43.

Frawley, K.A. et al. Nov. 5, 1993. "Face to Face: Do Computerized Patient Records Risk Invading Patient Privacy More than Paper Records".

Friedman, MD, Richard B. Jan. 1973. "A Computer Program for Simulating the Patient-Physician Encounter." Journal of Medical Education. vol. 48, pp. 92-97.

Friedman, PhD, Carol et al. 1995. "The Canon Group's Effort: Working Toward a Merged Model." Journal of the American Medical Informatics Association. vol. 2, No. 1, pp. 4-18.

Frost, R.D. et al. 1993. "Integrated Clinical Decision Support Using an Object-Orionted Database Management System." Methods of Information in Mecicine. 32, pp. 154-160.

Genesereth, Michael R. 1982. "Diagnosis Using Hierarchical Design Models." Proceedings of National Conference on AI. pp. 278-283.

Gennari, John H. et al. Mar. 1995. "Rouse with Protoge-II: From Elevators to Ribosomes."Knowledge Systems Laboratory Report. KSL-94-71.

Gennari, John H. et al. May 1994. "Mapping Domains to Methods in Support of Reuse." Knowledge Systems Laboratory Report. KSL-93-57.

Gorevini et al. Sep. 1990. "Modeling the Treatment Scheme of Sustained Ventricular Tachycardia with a Bayesian Belief Network." IEEE Proceedings of Computers in Cardiology.

Gibbons, Andrew S. et al. May 1993. "The Future of Computer-Managed Instruction (CMI)." Educational Technology. pp. 7-11.

Gilardoni, Luca et al. "Hierarchucal Pattern Matching for Knowledge Based News Calegorization." Quinary SpA. Milano. Italy. pp. 67-81.

Gitlin, R.D. et al. 1992. Data Communication Principles. Plenum Press.

Gonella, J.S. et al, 1994, "Disease Staging Clinical Criteria," MEDSTAT Systems. 4th (supplementary) Edition.

Goodkovsky, Vladimir A. et al. "Pop Class Intelligent Tutoring Systems: Shell, Toolkit & Design Technology." Moscow State Institute for Physics and Engineering.

Goodyear, O.M. et al. 1991. "Integrating a Medical Database and Advisory System." Med. Inform. vol. 16, No. 3. pp. 315-321.

Green James H. 1992. The Irwin Handbook of Telecommunications. Irwin Professional Publishing. Second Edition.

Green, Larry A. et al. Sep. 1993. "How Representative of Typical Practice are Practice Based Research Networks?" Arch Family Med. vol. 2, pp. 939-949.

Greenbaum, J. et al. 1991. "Understanding Practice: Video as Medium for Reflection and Design, IN." Design at Work: Cooperative Design of Compute Systems. Lawrence Earlbaum, Associates. pp. 65-89.

Gu, Huanying (Helen) et al. "Utilizing OODB Schema Modeling for Vocabulary Management." CIS Dept. & CMS NJIT, Newark, New Jersey. pp. 274-278.

Guslafson, PhD, David H. et al. Jan-Mar. 1986 "Decision Theoretic Methodology for Severity Index Development." Medical Decision Making. vol. 6. No. 1. pp. 27-35.

Hakman, M. et al. 1991. "KBSIM: A System for Interactive Knowledge-Based Simulation." Computer Methods and Programs in Biomedicine. Elsevier Publishers B.V. vol. 34, pp. 91-113.

Haladyna, Thomas M. 1989. "A Taxonomy of Multiple-Choice Item-Writing Rules." Applied Measurement in Education. 2(1), pp. 37-50.

Harless. William G. 1976. "Merit—An Application of Case." Information Technology in Health Science Education. New York: Plenum Press. pp. 565-569.

Hartz., MD, PhD, Arthur et al. Jul. Sep. 1986. "Stochastic Thresholds." Medical Decision Making. vol. 6, No. 3, pp. 145-148.

Heckerling, P.S. et al. 1991. "The Effect of Incomplete Knowledge on the Diagnosis of a Computer Consultant System." Med. Inform, vol. 16, No. 4. pp. 363-370.

Heckerman, D.E. et al. Jul. 1992. "Toward Normative Expert Systems: Part I the Pathfinder Project." Knowledge Systems Laboratory Report. KSL-92-66.

Hersch, MD, William R. et al. Jan./Feb. 1994. "A Performance and Failure Analysis of Saphire with a Medline Test Collection." Jounal of the American Medical Informatics Association. vol. 1, No. 1, pp. 51-60.

Herskovits, Edward et al. Aug. 1990. "Kutato: An Entropy-Driven System for Construction of Probabilistic Expert Systems, from Databases." Knowledge Systems Laboratory Report. KSL-90-22.

Herzog, Christian. "Understanding Students' Solutions in SYPROS." AI-ED 95,Poster Session.

Hietala, Penlti et al. "A Framework for Building Agent-Based Learning Environments." Dept. of Computer Science, University of Tampere, Finland.

Hilden, MD, Jorgen et al. Jan.-Mar. 1992. "A Pitfall in Utility Assessment—Patients' Undisclosed investment Decisions." Medical Decision Making. vol. 12, No. 1, pp. 39-43.

Hohne, K.H. et al. Jan. 1996. "A 'Virtual Body' Model for Surgical Education and Rehearsal." Computer. vol. 29, Issue 1, pp. 25-31.

Horvitz, Eric J. Aug. 1990. "Rational Metareasoning and Compilation for Optimizing Decisions Under Bounded Resources." Knowledge Systems Laboratory Report. KSL-89-81.

Hughes, Christopher. 1989. "The Representation of Uncertainty in Medical Expert Systems." Med. Inform. vol. 14, No. 4, pp. 269-279.

Ikeda, Mitsuru et al. "Ontological Issues of CSCL Systems Design." ISIR. Osaka Unviersity, Osaka. Japan. pp. 242-249.

International Preliminary Examination Report from PCT Application No. PCT/US00/08942.

International Search Report from PCT Application No. PCT/US00/08942.

Isaacs, E. et al. 1993. "Graphical Access to Medical Expert Systems: IV. Experiments to Determine the Role of Spoken Input." Methods of Information in Medicine. 32, pp. 18-32.

Jain, Nielsh L. et al. 1992. "Ranking Radiotherapy Treatment Plans Using Decision-Analytic and Heuristic Techniques," Computers and Biomedical Research. vol. 25, pp. 374-383.

Jambaud, Pierre et al. "Contribution to Negotiation Studying: A Knowledge Items Approach." LIRMM. UMR CNRS-UM2 n 9928, Montpellier Cedex.

Jimison, Holly B. et al. Jun. 1992. "Patient-Specific Explanation in Models of Chronic Disease." Knowledge Systems Laboratory Report. KSL-92-60 cited by other.

Jirousek, Radim et al. Jun. 1997. "Constructing Probabilistic Models." International Journal of Medical Informatics. Elsevier Scientific Publishers. vol. 45, No. 1-2, pp. 9-18.

Johansson, B. et al. 1998. "Database and Knowledge Base Integration A Data Mapping Method for Arden Syntax Knowledge Modules. " Methods of Information in Medicine. 35. pp. 302-308.

Johansson, Bo, G. et al. Nov. 8-11, 1992. "An Object Oriented Approach to Interpret Medical Knowledge Based on Ardon Syntax." Proceedings of Sixteenth Annual Symposium on Computer Applications in Medical Care: A Conference of the American Medicalinformatics Association. pp. 52-56.

Jonasson, David H. 1993. "Constructivist Uses of Expert Systems to Support Learning." Journal of Computer-Based Instruction. vol. 20. No. 3, pp. 86-94.

Kahn, M.G. et al. 1987. "Representation and Use of Temporal Information in ONCOCIN." Knowledge Systems Laboratory Report. KSL-85 8.

Kahn, Michael G. et al. Nov. 1989. "Model-Based Interpretation of Time-Varying Medical Data." Knowledge Systems Laboratory Report. KSL-89-34.

Kahn, Michael G., et al. 1991. "TQuery: A Context-Sensitive Temporal Query Language." Computers and Biomedical Reserch. 24, pp. 401-419.

Kaplan, Simon M. et al. Aug. 18-20, 1997. "Designing Support for Remote Intensive-Caro Telehealth Using the Locales Framework." Proceedings of the Conference on Desiging Interacive Systems: Processes, Practices, Methods and Techniques. TheNetherlands. pp. 173-184.

Kassirer, MD. Jerome P. et al. 1987. "Decision Analysis: A Progess Report." Annals of Internal Medicine. pp. 275-291.

Katz, Irvin R. 1994. "From Laboratory to Test Booklet: Using Expert Novice Comparisons to Guide-Design of Performance Assessments." Division of Cognitive and Instructional Science Educational Testing Service.

Kelly, G.A. 1995. "The Psychology of Personal Constructs." New York, NY: Norton Press.

Klein, David A. et al. Jan. 1992. "Interactive Diagnosis and Repair of Decision-Theoretic Models." Knowledge Systems Laboratory Report. KSL-90-19.

Kleinmuntz, Benjamin. Mar. 20, 1992. "Computers as Clinicians: An Update." Computer Biol. Med., vol. 22, No. 4, pp. 227-237.

Kolstad, Rosemarie K. 1983, "The Failure of Distractors on Complex Multiple-Choice Items to Prevent Guessing." Education Research Quarterly. vol. 8, No. 2, pp. 44-50.

Koubek, Richard J. 1989. "The Implementation and Evaluation of a Theory for High Level Cognitive Skill Acquisition Through Expert Systems Modeling Techniques." Ergonomics, vol. 32. No. 11, pp. 1419-1429.

Kreitar, Clarence D. et al, 1989. "Effectiveness of Multiple True-False Items." Applied Measurement in Education. vol. 2, No. 3, pp. 207-216.

LaDuca, Anthony Jun. 4, 1994. "Framing the Primary Care Physician: Lessons From Physician Licensure." AAFP Primary Care Competencies Conference.

Lane, C.D. et al. 1986 "Graphical Access to Medical Expert Systems: II Design of an Interface for Physicians." Knowledge Systems Laboratory Report. KSL-85-15.

Lanzola, G. et al. 1992. "A Specialized Framework for Medical Diagnostic Knowledge-Based Systems." Computers and Biomedical Research. vol. 25, pp. 351-365.

Loman, Stephane et al. "A Multi-Agent Approach to Model Student Reasoning Process." IREMIA. Universite de La Reunion. La Reunion. France. pp. 258-264.

Lou, Won-Jeng et al. Jun. 10-12, 1994, "Educational Patient Simulation in MEDASPC." Proceedings of the 1994 IEEE Seventh Symposium on Computer Based Medical Systems. pp. 88-93.

Lewinson, Lisa. Jul./Aug. 1994. "Representing Medical Knowledge—The Arden Syntax." PC AI, pp. 32-35.

Li, Zhongmin et al. Aug. 1991. "Developing a Research Reference Interface for Knowledge-Based Instructional Design Tools." Educational Technology. pp. 7-16.

Lim, Ian et al. 1993. "Rule Based Artifical Intelligence Expert System for Determination of Upper Extremity Impairment Rating." Computer Methods and Programs in Biomedicine. 39. pp. 203-211.

Lindberg, D.A.B. et al. 1993. "The Unified Medical Language System." Methods of Information in Medicine. vol. 32, pp. 281-291.

Linster, Marc. 1969, "Towards a Second Generation Knowledge Acquisition Tool." Knowledge Acquistion. vol. 1, pp. 163-183.

Linster, Mark et al. Nov. 1992. "Use of KADS to Create a Conceptual Model of the ONCOCIN Task." Knowledge Systems Laboratory Report. KSL-92-36.

Lowe, MD, Henry J. et al. Apr. 13, 1994, "Understanding and Using the Medical Subject Headings (MeSH) Vocabulary to Perform Literature Searches." JAMA. vol. 271, No. 14, pp. 1103-1108.

Marek, Victor et al. Mar. 29, 1996. "Alogrithms for Knowledge Acquisition and Patient Generation." University of Kentucky. pp. 1-36.

Mays. Eric et al. 1996. "Scalable and Expressive Medical Terminologies." pp. 259-263.

McLeish, Mary et al. May 1987. "Issues in the Development of Intelligent Tutoring Systems." Dept. of Computing & Information Science, University of Guelph, Ontario. pp. 108-124.

McSherry, D.M.G. 1986. "Intelligent Dialogue Based on Statistical Models of Clinical Decision-Making." Statistics in Medicine. vol. 5, pp. 497-502.

Mehrez, PhD, Abraham et al. Apr.-Jun. 1989. "Quality-Adjusted Life Years, Utility Theory and Healthy-Years Equlvalents." Medical Decision Making. vol. 9, No. 2, pp. 142-149.

Merola, A. John et al. 1973. "Computer-Supported Independent Study in the Basic Medical Sciences." Information Technology in Health Science Education. New York; Plenum Press. pp. 17-43.

Miaoulis, G. et al. 1992. "New Role of a Medical Documentation System." Med. Inform. vol. 17, No. 3, pp. 165-178.

Midoro et al. "Interactive Video and Artifical Intelligence: A Convenient Marriage." PLET. vol. 25, No.4, pp. 299-309.

Miller, MD, Randolph et al. 1986. "Quick Medical Reference (QMR) for Diagnostic Assurance." MD Computing. vol. 3, No. 5, pp. 34-49.

Millis, MD, David H. Aug. 1990, "PSY/JD: An Advisory System for Legal Aspects of Decision Making in the Psychiatric Emergency Room." Knowledge Systems Laboratory Report. KSL-90-54.

Moda, C.J. et al. 1984. "A Mathematical Overview of a Computer Simulation Model of Maternity Histories with Illustrative Examples." IMA Journal of Mathematics Applied in Medicine & Biology. vol. 1, pp. 107-121.

Molta, Enrico et al, 1991, "Methodological Foundations of KEATS, the Knowledge Engineer's Assistant." Knowledge Acquisition. vol. 3, pp. 21-27.

Mullins, MD, H.C. et al. 1996, "The Efficacy of SNOMED, Read Codes and UMLS in Coding Ambulatory Family Practice Clinical Records." pp. 135-139.

Musen, M.A et al., 1995. "PROTEGE-II: Computer Support for Development of Intelligent Systems from Libraries of Components." MEDINFO 95 Proceedings. IMIA.

Musen, Mark A. 1989, "Automated Support for Building and Extending Expert Models." Knowledge Systems Laboratory Report. KSL-86-26.

Musen, Mark A. et al. 1987. "Use of a Domain Model to Drive an Interactive Knowledge-Editing Tool." Knowledge Systems Laboratory Report. KSL-86-24.

Musen, Mark A. et al. Apr. 1995. "A Component Based Architecture for Automation of Protocol-Directed Therapy." Knowledge Systems Laboratory Report. KSL-95-28.

Musen, Mark A. et al. Nov. 1992. "T-HELPER: Automated Support for Community-Based Clinical Research." Knowledge Systems Laboratoy Report. KSL-92-08.

Musen, Mark A. et al. Oct. 1991. "A Problem-Solving Model for Protocol-Based Care: From e-ONCOCIN to EON." Knowledge Systems Laboratory Report. KSL-91-61.

Musen, Mark A. et al. Sep. 1994. "PROTEGE-II: Computer Support for Development of Intelligent Systems from Libraries of Components." Knowledge Systems Laboratory Report. KSL-94-60.

Musen, Mark A. Jan. 1989. "Languages for Knowledge Acquistion: Building and Extending Models." Knowledge Systems Laboratory Report. KSL-89-07.

Musen, Mark et al. "Rationale for Knowledge Base Redesign in a Medical Advice System," Knowledge Systems Laboratory Report. KSL-85-17.

Naeymi-Rad, Frank. 1989. "A Feature Dictionary Supporting a Multi-Domain Medical Knowledge Base." Computer Methods and Programs in Biomedicine. vol. 30, pp. 217-228.

National Institutes of Health: National Library of Medicine. Aug. 1992. "Fact Sheet: Grateful Med.RTM.," U.S. Department of Health and Human Services.

National Institutes of Health: National Library of Medicine. Feb. 1992. "Fact Sheet: National Library of Medicine Outreach." U.S. Department of Health and Human Services.

National Institutes of Health: National Library of Medicine. Jan. 1993. "Fact Sheet: UMLS.RTM. Information Sources Map," U.S. Department of Health and Human Services.

National Institutes of Health: National Library of Medicine. Jan. 1993, "Fact Sheet: UMLS.RTM. Metathesauras.RTM,." U.S. Department of Health and Human Services.

National Institutes of Health: National Library of Medicine. Jan. 1993. "Fact Sheet: Unified Medical Language System. RTM.." U.S. Department of Health and Human Services.

National Institutes of Health: National Library of Medicine. Jul. 1992. "Fact Sheet: The National Library of Medicine." U.S. Department of Health and Human Services.

National Institutes of Health: National Library of Medicine. Nov. 1991. "Fact Sheet: UMLS.RTM. Information Sources Map." U.S. Department of Health and Human Services.

National Institutes of Health: National Library of Medicine. Nov. 1991. "Fact Sheet: UMLS.RTM. Metathesaurus.TM.." U.S. Department of Health and Human Services.

National Institutes of Health: National Library of Medicine, Nov. 1991. "Fact Sheet: UMLS.RTM. Semantic Network." U.S. Department of Health and Human Services.

National Institutes of Health: National Library of Medicine, Nov. 1991, "Fact Sheet: Unified Medical Language System," U.S. Department of Health and Human Services.

National Institutes of Health: National Library of Medicine. Nov. 1992. "Fact Sheet: UMLS.RTM. Semantic Network." U.S. Deaprtment of Health and Human Services.

National Institutes of Health: National Library of Medicine. Nov. 1992. "NLM Seeks Volunteers to Test Access to Citations of HSR Literature in Mediars." U.S. Department of Health and Human Services.

National Institutes of Health: National Library of Medicine. Nov. 1992. "NLM's Health Services Research Information Program: Highlights of Activities." Department of Health & Human Services.

National Institutes of Health: National Library of Medicine. Oct. 1991. "Fact Sheet: National Network of Libraries of Medicine." U.S. Department of Health and Human Services.

Norman, Joseph, Mar. 1995, "Building the Computer-Based Patient Record," Knowledge Systems Laboratory Report. KSL-95-24.

Nowlan, W.A. et al. 1994. "From Terminology to Terminology Services." pp. 150-154.

Okamoto, Toshio et al, "The Intelligent Learning Support System on the Distributed Cooperative Environment." The Graduate School of Information Systems, University of Electro-Communications, Tokyo, Japan.

Paquette, Gilbert et al. Nov.-Dec. 1994. "An Intelligent Support System for Course Design." Educational Technology. pp. 50-57.

Pouker, Stephen G. et al. Jan. 29, 1987. "Medical Progress-Decision Analysis." The New England Journal of Medicine. vol. 316, No. 5.

Porroault, Leslie E. Oct. 1987. "Automatic Test Case Generation by Modeling Patient States and Physician Actions." Knowledge Systems Laboratory Report. KSL-87-63.

Pinciroli, F. et al. 1992. "Object-Orientated DBMS Techniques for Time-Oriented Medical Record." Med Inform. vol. 17, No. 4. pp. 231-241.

Polaschek, Jeanette X. et al. Aug. 1990. "A Computer Program for Statistically Based Decision Analysis." Knowledge Systems Laboratory Report. KSL-90-50.

Pole, P.M. et al. 1996. "Mapping the Galen Core Model to Snomed III: Initial Experiments." AMIA. Inc. pp. 100-104.

Poon, Alex et al. Nov. 1992. "Augmented Transition Networks as a Representation for Knowledge-Based History-Taking Systems." Knowledge Systems Laboratory Report. KSL-92-20.

Poses et al. Oct.-Dec. 1988. "Evaluating Physicians' Probabilistic Judgments." Medical Decision Making. vol. 8, No. 4. pp. 233-240.

Puerta, Angel R. et al. Aug. 1992. "Modeling Tasks with Mechanism." Knowledge Systems Laboratory Report. KSL-92-30.

Puerta, Angel R. et al, Aug. 1994. "Model-Based Generation of User Interfaces." Knowledge Systems Laboratory Report. KSL-94-51.

Rassinoux, PhD, Anne Marie et al. 1996. "Modeling Principles for QMR Medical Findings." pp. 264-268.

Rector, A.L. et al, 1993. "A Framework for Modelling the Electronic Medical Record." Methods of Information in Medicine. 32, pp. 109-119.

Rector, A.L. et al. 1994, "Goals for Concept Representation in the GALEN Project." Medical Informatics Group, Dept. of Computer Science, University of Manchester.

Rector, MD, PhD, A.L. et al. Jan./Feb. 1995. "Medical-Concept Models and Medical Records: An Approach Based on Galen and Pen & Pad." Journal of the American Medical Informatics Association. vol. 2, No. 1, pp. 19-35.

Reshetar, Rosemary A. et al. Apr. 1992. "An Adaptive Testing Simulation for a Certifying Examination." Presented at the Annual Meeting of the American Educational Research Association. San Franciso. CA.

Rikken, Flour et al. "Specifying Adverse Drug Reactions by Formulating Contexts Through CLARIT Processing of Medical Abstracts".

Rocha, Roberto A. et al. 1996. "Coupling Vocabularies and Data Structures: Lessons from LOINC.TM.." pp. 90-94.

Rothenfluh, Thomas E. et al. Feb. 1994. "Reusable Onlologies, Knowledge Acquisition Tools and Performance Systems: PROTEGE-II Solutions and Sisyphus-2." Knowledge Systems Laboratory Report. KSL-93-65.

Rothwell, MD. David J. et al. 1996. "Managing Information with SNOMED: Understanding the Model." pp. 80-83.

Rovinolli, PhD, Richard J. "Research and Developmental Issues for a Computer-Based Testing Project for the American Board of Family Practice".

Rubenstein, R.Y. 1981 "Simulation and the Monte Carlo Method." John Wiley & Sons, Inc. New York, NY.

Russ, Thomas A. 1986. "A System for Using Time Dependent Data in Patient Management." MEDINFO 86. Elsevier Science Publishers B.V. pp. 165-169.

Ryan, Margaret. Apr. 29, 1996. "Distance Health Care is Latest Medicine." Electronic Engineering Times. pp. 55-56.

Sager, PhD. Naomi et al. Mar./Apr. 1994. "Natural Language Processing and the Representation of Clinical Data." Journal of the American Medical Informatics Association. vol. 1, No. 2, pp. 142-160.

Santos-Gomez, Lucinio et al. 1992. "Empirical Evaluation of Decision Tables for Constructing and Compreshending Expert System Rules." Knowledge Acquisition. vol. 4, pp. 427-444.

Satomura, Y. et al. 1992. "Automated Diagnostic Indexing by Natural Language Processing." Med. Inform. vol. 17, No. 3, pp. 149-163.

Schroder, Martin. "Knowledge-Based Processing of Medical Language: A Language Engineering Approach." German Conference on Artificial Intelligence.

Schwartz, William B. et al. "Artifical Intelligence in Medicine: Where Do We Stand." Sounding Board. vol. 316. No. 11, pp. 685-688.

Seidel, Robert J. 1994. "An Historical Perspective and a Model for Evaluation of Intelligent Tutoring Systems." Journal of Educational Computing Research. vol. 10(2), pp. 103-128.

Shahar, Yuval et al. Feb. 1995. "Knowledge Based Temporal Abstraction in Clinical Domains." Knowledge Systems Laboratory Report. KSL-95-23.

Shahar, Yuval et al. Nov. 1991. "Temporal-Abstraction Mechanisms in Management of Clinical Protocols." Knowledge Systems Laboratory Report. KSL-91-19.

Shahar, Yuval. Mar. 1995. "A Framework for Knowledge Based Temporal Abstraction." Knowledge Systems Laboratory Report. KSL-95-29.

Shahar, Yuvel et al. Dec. 1992. "RESUME: A Temporal-Abstraction System for Patient Monitoring." Knowledge Systems Laboratory Report. KSL-92-84.

Shahar, Yuvel et al. Nov. 1992. "A Temporal Abstraction System for Patient Monitoring." Knowledge Systems Laboratory Report. KSL-92-14.

Shea, Judy A. et al. 1992. "An Adaption of Item Modeling for Developing Test-Item Banks." Teaching and Learning in Medicine. vol. 4, No. 1, pp. 19-24.

Shwe, Michael et al. Jan. 1992. "An Empirical Analysis of Likelihood-Weighting Simulation on a Large, Multiply-Connected Belief Network," Knowledge Systems Laboratory Report. KSL-90-23.

Simmons, R. et al. 1993. "The Roles of Knowledge and Representation in Problem Solving." Springer Verlag. New York, NY. pp. 27-45.

Simmons, Reid. "Generate, Test and Debug: A Paradigm for Combining Associational and Causal Reasoning In." School of Computer Science, Carnegie Melon University, Pittsburgh, Pennsylvania.

Sittig, PhD, Dean F. et al. Jan./Feb. 1995. "Evaluating a Computer Based Experiential Learning Simulation: A Case Study Using Criterion Referenced Testing." Computers in Nursing. vol. 13, No. 1, pp. 17-24.

Sleeman, D. "Intelligent Tutoring Systems: A Review." School of Education & Dept. of Computer Science, Stanford University.

Solomon, PhD, David J., et al. Feb. 1992. "A Pilot Study of the Relationship Between Experts Ratings and Scores Generated by the NBME's Computer-Based Examination System." Academic Medicine. vol. 67. No. 2, pp. 130-132.

Spector, J. Michael et al. Oct. 1992. "Intelligent Frameworks for Instructional Design." Educational Technology. pp. 21-27.

Spohn, Darren L. 1993. Data Network Design. McGraw-Hill, Inc.

Spyns, P. 1996. "Natural Language Processing in Medicine: An Overview," Methods of Information in Medicine. 35, pp. 285-301.

Stallings, William. 1993. Computer Organization and architecture, MacMillian Publishing Co. Third Edition.

Stein, Adam et al. 1996. "Knowledge Acquisition for Temporal Abstraction." pp. 70-74.

Stevens, R.H. et al. Nov. 1989. "Evaluating Preclinical Medical Students by Using Computer-Based Problem-Solving Examinations." Academic Medicine. vol. 64, pp. 685-687.

Stillman, MD, P.L. et al. 1978. "Ensuring the Clinical Competence of Medical School Graduates Through Standardized Patients." Arch. Int. Med. vol. 147, pp. 1049-1052.

Stocking, Martha L. Oct. 1994. "An Alternative Method for Scoring Adaptive Tests, Research Report." Educational Testing Service. RR-94-98.

Stonebraker, Michael. "The Design of the Postgres Storage System." EECS Dept. University of California, Berkeley, California.

Stuart-Buttle, C.D.G. et al. 1996. "A Language of Health in Action: Read Codes, Classifications and Groupings." pp. 75-79.

Suchman, Lucy A. et al. "Understanding Practice: Video as a Museum for Reflection and Design".

Sumner II et al, "Simulating Patient with Parallel Health State Networks" Proceedings of the American Medical Informatics Association AnnualSymposium, 1998.

Sumner II, MD, Walton et al Jan.-Feb. 1996. "A Revolution in the Assessment of Clinical Knowledge." JABFP, vol. 9, No. 1, pp. 41-52.

Sumner, II, MD, Walton et al. "Describing Medicine and Generating Patients with Parallel Health State Networks".

Sumner, II, MD, Walton et al. 1993. "Designing a Knowledge Base to Support Family Practice Certification Examinations." Presented at Proceedings of the Seventh Annual Symposium and Computer Applications in Medical Care, Washington, DC.

Sumner, II, MD. Walton et al. 1995. "Data Transformations for Patient Simulations." Paper presented at the the Proceedings of the Nineteenth Annual Sumposium on Computer Applications in Medical Care, New Orleans, LA.

Sumner, II, MD. Walton et al. 1998. "Simulating Patients with Parallel Health State Networks." AMIA 1998 Annual Symposium. pp. 438-442.

Sumner, II, MD, Walton, Jan. 1993. "A Review of Iliad and QMR for Primary Care Providers: Two Diagnostic Computer Programs." Archives of Family Medicine. vol. 2, pp. 87-95.

Tocuci, Gheorghe et al, 1994. "A Framework for Knowledge Based Refinement Through Multistrategy Learning and Knowledge Acquisition." Knowledge Acquisition. 6, pp. 137-162.

Tsuji, S. et al. 1986. "Graphical Access to Medical Expert Systems: I. Design of a Knowledge Engineer's Interface." Knowledge Systems Laboratory Report. KSL-85-11.

Tu, S.W. et al. Dec. 1989. "Episodic Skeletal-Plan Refinement Based on Temporal Data." Knowledge Systems Laboratory Report. KSL-87-70.

Tu, S.W. et al. Nov. 1992. "A Methodology for Determining Patients' Eligibility for Clinical Trials." Knowledge Systems Laboratory Report. KSL-92-78.

Tu, Samson W. et al. Dec. 1994. "Ontology Based Configuration of Problem Solving Methods and Generation of Knowledge-Acquisition Tools: Application of PROTEGE-II to Protocol-Based Decision Support." Knowledge Systems Laboratory Report. KSL-94-22.

Van der Lei, J. et al. Nov. 1990. "Critiquing Physician Decision Making Using Data from Automated Medical Records: Assessing the Limitations." Medical Computer Science Laboratory.

Van der Lei, Johan et al. Aug. 1991. "A Model for Critiquing Based on Automated Medical Records." Knowledge Systems Laboratory Report. KSL-91-18.

Van der Lei, Johan et al. Dec. 14, 1991. "Comparison of Computer-Aided and Human Review of General Practitioners' Management of Hypertension." The Lancet. vol. 338, pp. 1504-1508.

Van Marcke, Kris et al. "Learnor Adaptivity in Generic Instructional Stralogies." Knowledge Technologies, N.V. pp. 323-337.

Van Marcke, Kris. "A Generic Task Model for Instruction." Knowledge Technologies N.V. Brussels, Belgium. pp. 171-194.

Wallace, Scott. May 1994. "The Computerized Patient Record." BYTE. pp. 67-73.

Webster, Laurio et al. 1993. "Exercise Countermeasure Protocol Management Expert System." Computer Methods and Programs in Biomedicine, 39, pp. 217-223.

Weinberg, Arron D. 1973. CAI at the Ohio State University College of Medicine (1973). Computer Biology Medicine. vol. 3, pp. 299-305.

Wellman, Michael P. et al. Oct.-Dec. 1989. "Automated Critiquing of Medical Decision Trees." Medical Decision Making. vol. 9, No. 4, pp. 272-284.

Widman, Lawrence E. 1989. "Expert System Reasoning About Dynamic Systems by Semi-Quantitative Simulation." Computer Methods of Programs in Biomedicine. pp. 95-113.

Widman, MD, PhD, Lawrence E. 1986 "Representation Method for Dynamic Casual Knowledge Using Semi-Quantitative Simulation," MEDINFO 86. Elsevier Science Publishers. pp. 180-184.

Wigton, Robert S. Oct.-Dec. 1988. "Use of Linear Models to Analyze Physicians Decisions." Medical Decision Making. vol. 8, No. 4, pp. 241-267.

Woodward, PhD, Beverly. Nov. 23, 1995. "The Computer Based Patient Record and Confidentiality." Sounding Board. vol. 333, No. 21, pp. 1419-1422.

Woolf, Beverly Park. "Toward a Computational.Model of Tutoring." ETR& D. vol. 40, No. 4, pp. 49-64. cited by other.

Yoshikawa, Masazumi et al, "Constraint Satisfaction with a Multi-Dimensional Domain:" C & C Systems Research & Laboratories, NEC Corporation, Japan, pp. 252-259.

Zahedi, Fatemeh. 1990. "A Method for Quantitative Evaluation of Expert Systems." European Journal of Operational Research. 48. pp. 136-147.

Zech, Linda et al. 1995. "Computer Technology and Complex Problem Solving: Issues in the Study of Complex Cognitive Activity." EARLI, Symposium.

Zenq, Quing et al. 1996. "Mapping Medical Vocabularies to the Unified Medical Language System." pp. 105-109.

* cited by examiner

COMPUTER ARCHITECTURE AND PROCESS OF PATIENT GENERATION, EVOLUTION, AND SIMULATION USING KNOWLEDGE BASE SCRIPTING

RELATED APPLICATIONS

This application is a continuation of U.S. Ser. No. 10/265,599, filed Oct. 8, 2002, now U.S. Pat. No. 7,024,399 which is a divisional of U.S. Ser. No. 09/521,242, filed Apr. 5, 2000, now U.S. Pat. No. 7,107,253 which claims priority to U.S. Ser. No. 60/127,850, filed Apr. 5, 1999, the details of which are hereby incorporated by reference.

FIELD OF THE INVENTION

The present invention is generally related to a computer architecture and process for patient generation, evolution, and simulation, and more particularly to a computer architecture and process for patient generation, evolution, and simulation for a computer based testing system using belief networks and/or causal probabilistic networks as a scripting language.

BACKGROUND OF THE RELATED ART

Medical certifying organizations have traditionally relied upon paper and pencil cognitive examinations as a method for the assessment of the candidate's medical knowledge. Traditional formats such as multiple choice questions have well-defined operating characteristics and reliability for examining cognitive knowledge capabilities. See, for example, Stocking M L, An alternative method for scoring adaptive tests, Research Report RR-94-98, 1994, incorporated herein by reference.

However, these tools generally measure in only cognitive knowledge. These methods provide only primitive ability to assess a candidate's problem-solving abilities. See, for example, Stillman P L, Swanson D B, Ensuring the clinical competence of medical school graduates through standardized patients, Arch Int Med 1978, Vol. 147, pages 1049-52, incorporated herein by reference.

Several organizations have previously experimented with computer-delivery of clinical content and evaluation. In the late 1960s and 1970s, the Ohio State University developed a self-directed Independent Study Program which utilized a "Tutorial Evaluation System," for conveying curriculum content. See, for example, Weinberg A D, CAI at the Ohio State University College of Medicine, Comput Biol Med 1973, Vol. 3, pages 299-305; Merola A J, Pengov R E, Stokes B T, Computer-supported independent study in the basic medical sciences in: DeLand E C (ed). Information Technology in Health Science Education, Plenum Press, New York, 1973, incorporated herein by reference.

Co-synchronously Dr. Octo Barnett's laboratory at the Massachusetts General hospital began development of clinical simulations. See, for example, Barnett G O, The use of a computer-based system to teach clinical problem-solving, Computers in Biomedical Research, Academic Press, New York 1974; Vol. 4, pages 301-19; Barnett G O, Hoffer E P, Famiglieti K T, Computers in medical education: present and future, Proceedings of the Seventh Annual Symposium on Computer Applications in Medical Care, IEEE Press, Washington, D.C. 1983, pages 11-13, incorporated herein by reference. The clinical simulations used the MUMPS language.

At approximately the same time, investigators at the University of Illinois developed a simulation model known as (Computer-Associated Simulation of the Clinical Encounter, or "CASE"). See, for example, Harless W G, Farr N A, Zier M A, et al., MERIT—an application of CASE, Deland E C (ed), Information Technology in Health Science Education, Plenum Press, New York 1978, pages 565-69, incorporated herein by reference. This system was at one time considered by the American Board of Internal Medicine (ABIM) as at least one component of a recertification process. Friedman R B, A computer program for simulating the patient-physician encounter, J Med Educ 1973, Vol. 48, pages 92-7, incorporated herein by reference. Research supported by the ABIM demonstrated that a computerized examination system appeared feasible in professional evaluation/certification settings. Reshetar, R A, et al., An Adaptive Testing Simulation for a Certifying Examination, presented at the Annual Meeting of the American Educational Research Association, San Francisco, Calif., April, 1992, incorporated herein by reference.

Stevens and colleagues have also demonstrated the feasibility of using computer-based systems for testing problem-solving ability in undergraduate medical school curriculum applications. See, for example, Stevens R H, et al, Evaluating Preclinical Medical Students by Using Computer-Based Problem-Solving Examinations, Academic Medicine 1989, Volume 64, pages 685-87, incorporated herein by reference. Sittig and colleagues have also examined the utility of computer-based instruction in teaching naïve users basic computer techniques such as "drag and drop" and other computer operations. See, for example, Sittig D F, Jiang Z, Manfre S, et al., Evaluating a computer-based experiential learning simulation: a case study using criterion-referenced testing, Comput Nurs; 1995, Vol. 13, pages 17-24, incorporated herein by reference.

We have determined that the above described medical assessment processes suffer from two weaknesses: 1) test development requires re-generation of an examination with new material on a recurring (usually annual) basis; 2) although multiple choice questions demonstrate reliable performance in measuring cognitive knowledge, the use of this format for assessing clinical problem solving has not been supported by the literature. Another system was developed at the University of Wisconsin. This project served as the nidus for the Computer-Based Examination (CBX) developed by the National Board of Medical Examiners (NBME). See, for example, Friedman R B, A computer program for simulating the patient-physician encounter, J Med Educ 1973, Vol. 48, pages 92-7; Clyman, Stephen G., Orr, Nancy A., Status Report on the NBME's Computer-Based Testing, Academic Medicine 1990, Vol. 65, pages 235-41, incorporated herein by reference. NBME's CBX development project has been in evolution for over a decade, and has demonstrated validity in examining professional degree candidates. See, for example, Solomon D J, Osuch J R, Anderson K, et al., A pilot study of the relationship between experts' ratings and scores generated by the NBME's computer-based examination system, Academic Medicine 1992, Vol. 67, pages 130-32, incorporated herein by reference.

However, we have determined that the CBX model suffers from the problem that the clinical simulations are "hardwired" in computer source code which must be re-coded for each new examination. Once the simulation has been used widely, the examination contents are no longer secure, necessitating continuous cycles of new simulation development.

The expert system literature describes the evolution in evaluation and training systems. Early artificial intelligence/ expert system work concentrated on "rules of thumb" or heuristics to represent problem-solving strategies identified by domain experts. See, for example, David J M, Krivine J P, Simmons R., Second generation expert systems: a step forward in knowledge engineering, in: David J M, Krivine J P, Simmons R. Second Generation Expert Systems, Springer Verlag, New York, N.Y. 1993, pages 3-23, incorporated herein by reference. We have determined that these rule-based systems were necessarily constrained to narrow domains, and that the knowledge contained in the rules was difficult to validate. Id.

In addition, early expert systems suffered from rapidly declining performance when exposed to circumstances outside narrowly defined domains. See, for example, Davis R. Expert systems: where are we and where do we go from here, AI Magazine, 1983, Vol. 3, pages 3-22; Simmons R. Generate, Test and Debug: A paradigm for combining associational and causal reasoning, in: David M, Krivine J P, Simmons R., Second Generation Expert Systems, Springer Verlag, New York, N.Y. 1993, pages 79-92, incorporated herein by reference. We have determined that this phenomenon occurred at least in part due to interactions among the many rules needed to define a domain. Recent work indicates that the robustness of such systems is enhanced by providing knowledge of different types. See, for example, Simmons R, Davis R., The roles of knowledge and representation in problem solving, In: David M, Krivine J P, Simmons R., Second Generation Expert Systems, Springer Verlag, New York, N.Y. 1993, pages 27-45, incorporated herein by reference.

We have further determined that experts generally not only relate to one dimension of knowledge when defining a rule, but also rely upon expansive knowledge of how systems work (i.e., physiology and pathophysiology in the medical domain) in performing real-world problem-solving. See, for example, Davis R., Expert systems: where are we and where do we go from here, AI Magazine, 1983, Vol. 3, pages 3-22, incorporated herein by reference. This realization has led to re-thinking regarding structure of knowledge-based systems to reflect the tasks such a system should accomplish, the methods the system should use to accomplish the tasks, and the knowledge required to support these methods. See, for example, David J M, Krivine J P, Simmons R., Second generation expert systems: a step forward in knowledge engineering, In: David J M, Krivine J P, Simmons R., Second Generation Expert Systems, Springer Verlag, New York, N.Y. 1993, pages 3-23, incorporated herein by reference.

We have also determined that knowledge-acquisition for such systems entails development of a model for the domain and instantiation (i.e., encode and enter needed information into the system's data structure) of the model with information acquired from knowledge donors. See, for example, David M, Krivine J P, Simmons R., Second generation expert systems: a step forward in knowledge engineering, In: David M, Krivine J P, Simmons R., Second Generation Expert Systems, Springer Verlag, New York, N.Y. 1993, pages 3-23; Breuker J, Weilenga B., Models of expertise in knowledge acquisition, In: Gida and Tasso (eds), Topics in Expert System Design: Methodologies and Tools, North Holland Publishing, 1989, incorporated herein by reference.

To obviate the above described weaknesses, we have determined that it is desirable to provide a computer-based testing project which will: 1) instantiate medical knowledge as object-oriented data structures known as knowledge base of family medicine; 2) utilize the medical knowledge structures to create realistic clinical scenarios (simulated patients); and 3) assess the candidate's clinical problem solving ability as the effective intervention in the clinical progress of the simulated patient through the selection of various actions made available by the testing system.

Applicants have recognized a need for a method and system for evaluating or educating a user using belief networks or causal probabilistic networks, such as Bayesian networks, to describe health state evolution, medical finding reveal structures, and/or management plan critiques.

Applicants have also recognized a need for an expert system for facilitating a user in the treatment of an actual patient using belief networks or causal probabilistic networks, such as Bayesian networks, to describe health state evolution, medical finding reveal structures, and/or management plan critiques.

SUMMARY OF THE INVENTION

The computer-based testing system described herein represents knowledge at multiple levels of complexity. For example, reactive airways disease is represented as a series of health states: Normal (Non-reactive) Airways, Reactive Airways-Mild, Reactive Airways-Moderate, and Reactive Airways-Severe. Each health state contains identifiers which relate the particular health state to precedents and antecedents (e.g., Normal Airways serves as the precursor health state for Mild Reactive airways disease, and Mild, Moderate and Severe Reactive Airways Disease represent target health states from the Normal circumstance.)

Each health state in turn has associated findings, and specific findings. For example, the Normal Airways state, the Finding "Shortness of Breath" is instantiated with the Specific Finding "No shortness of breath." Similarly, other Findings such as Respiratory Function and Severe Asthma Attack Frequency are instantiated with corresponding normal Specific Findings (Normal Respiratory Functions, and No Severe Attacks.) This representation transports to each new health state in a manner which we have determined to be analogous to diagnosis. See, for example, Genesereth M., Diagnosis using hierarchical design models, Proc. National Conference on AI, 1982, incorporated herein by reference.

The computer-based testing system of the present invention partitions knowledge into fundamental types: Health States, Agents, Findings, Specific Findings and Patterns describe system behaviors and characteristics. Courses-of-Action describe human activities which modify and evaluate the health state information and characteristics described in the model. Subdivision of knowledge types in this manner facilitates the knowledge acquisition process. This subdivision also promotes multiple levels of knowledge abstraction, which enhances the system's ability to represent varying levels of complexity.

For example, in the Computer-Based Testing System, a pattern such as incidence is further sub-divided into sub-patterns such as incidence in females versus males, and incidence in various racial/ethnic groups.

Multiple levels of abstraction and types of knowledge impose a substantial knowledge acquisition challenge. Knowledge acquisition includes several possible methodologies, including direct questioning of domain experts/ protocol analysis, see, for example, Ericsson Ka A, Simon H A, Protocol Analysis: Verbal Reports as Data, MIT Press. Cambridge, Mass. 1984, incorporated herein by reference, psychometric methods, see, for example, Kelly G A, The Psychology of Personal Constructs, Norton Press, New York, N.Y. 1955, incorporated herein by reference, and ethnographic methods, Suchman L A, Trigg R H, Understanding Practice: Video as a Medium for Reflection and Design, In: Greenbaum, J, Kyng M (eds)., Design at Work: Cooperative Design of Compute Systems, Lawrence Earlbaum Associates 1991, pages 65-89, incorporated herein by reference.

Advantageously, the Computer-Based Testing System of the present invention has included a blend of these approaches. Direct questioning has been used in querying family practice physicians regarding their knowledge of and approaches to specific knowledge domains (such as osteoarthritis). Additionally, knowledge acquisition has included access to appropriate scientific literature, which functionally serves to provide an ethnographic assay of actual practice. Knowledge acquisition has also entailed protocol analysis, both in terms of analyzing specific physicians' problem solving methodologies and incorporating explicit clinical processes such as those presented in published clinical guidelines (a specific example here is the otitis media with effusion guideline developed by the Agency for Health Care Policy and Research).

To facilitate development of such a system, the present invention is divided into three components: the knowledge base, the patient simulation generator, and the presentation system. The knowledge base has been designed and represented as a series of entity-relationships. The model has several fundamental entities: Patient, Health States, Findings, Courses of Action, and Agents. These entities have relationships of INTERACTS_WITH, CONTACTS, IS_RELATED, EXHIBITS, HAS, EXPOSED_TO, LEADS_TO, ASSOC_WITH, LINKS_TO, USES, IDENTIFY, MANAGE, ALTER, REVEAL, and EVALUATE.

FIG. 1 describes an overall or conceptual view of the entities and relationships included in the model. Rectangles indicate entities between entities in the model. Hexagons indicate relationships. Solid lines indicate Medical Knowledge Relationships (e.g., a course of action such as treatment with non-steroidal anti-inflammatory agents can modify specific findings such as pain in the patient with osteoarthritis.) Dotted lines indicate Simulation/Evolution relationships which define how a particular domain simulation has proceeded.

The patient simulation generator of the present invention relies upon a series of generation methods to instantiate patients for presentation to the certification/recertification candidate. The processes function to evolve the patient forward (to reflect progression of the disease process and response to interventions) and backward in time (to create a past history for the patient.) To accomplish these tasks, the system utilizes processes for:
1. Content specification—these processes define the scope of the simulation
2. Patient generation:
    Past History ("backward" generation)
    Present and Future History ("forward" generation)
3. Simulation processes (in addition to patient generation):
    Interface processes (for presentation of the patient findings developed from generation processes.)
    Book-keeping processes (for keeping track of candidates' responses and patient evolution)

The patient generation process proceeds on the basis of a specific health state identifier (coded in the database as a name and SNOMED code) passed to the process at the start of the simulation. The SNOMED International structured vocabulary is a versatile nomenclature for describing medical ideas. See, for example, Côté R A, Rothwell D J, Palotay J L, Beckett R S, Brochu L, editors, SNOMED International: The systematized nomenclature of human and veterinary medicine, 3rd ed. Northfield, Ill., College of American Pathologists, 1993, incorporated herein by reference. This nomenclature allows one to make inferences from the codes used to represent each idea. For instance, the code F-37022 represents "retrosternal chest pain." The first character, "F," indicates that the code is from a broad class of ideas called functions. The next to digits, "37," indicate that the code involves a refinement of the code F-37000, "chest pain, not otherwise specified." Similarly, code F-37020 specifies "precordial chest pain." The code F-37022 implies that retrosternal chest pain is a kind of precordial chest pain, which is a kind of chest pain, which is a kind of function.

The generation process produces a complete patient description which reflects the EXHIBITS, HAS, INTERACTS-WITH, EXPOSED-TO, IS-RELATED, and CONTACTS relationships described earlier. These generated entity relations are stored as a collection of records referred to as the "White Board" data structures. The information in these records serves as input to the patient evolution process, which in turn evolves the patient's health status and medical/personal characteristics as a function of the passage of time or physician/examinee intervention.

The original patient generation process is generally called once at the session's start; the system calls the evolution processes repeatedly in response to time progression and physician action.

The first phase of patient generation entails development of the patient's history outline. This outline describes the series of health states and risk factors the patient experienced to reach the current health state, TS. To develop TS, the system first calls the procedure GenderRace, which establishes the patient's sex and racial/ethnic origin. Next, the system establishes the patient's age and age at onset through the OnsetAge procedure. The CreatePerson process then assigns the patient a birth date and name.

Once the patient's age, sex, racial/ethnic origin, and age at onset of the condition have been established, the OutlineFirstStep procedure defines the precursor states and risk factors which serve as the substrata for evolving the patient to the current time and target health state. The OutlineGeneralStep procedure is then called iteratively until the patient has arrived at the current TS. These processes are described in greater detail below.

Logical and procedural knowledge in the database described as "reasoning elements" (RE) (for example, Bayesian network describing a generation method, Bayesian network describing a treatment plan, and the like), included in the generation methods described above, "shape selectors" which describe distributions for the n patterns by which health states evolve (patterns in turn are specified by findings and subpatterns), and courses of action (COA) which represent possible further diagnostic and management strategies which candidates might select.

The patterns and subpatterns are represented as probability distributions (discrete and continuous as appropriate for particular finding) specified through the knowledge acquisition process. At the beginning of a simulation, random number generation is used to select a "master percentile" (MP) which then serves as the reference for selecting particular patterns, findings and subpatterns from the appropriate specified distributions. These selected patterns are queried to provide description of specific findings such as hyperglycemia in response to physician/examinee requests for information which are in the form of "courses of action" for a particular health state (e.g., hyperglycemia as a manifestation of diabetes.)

Once presented with the patient description (age, race, sex, clinical findings), the candidate then selects appropriate COA's for further evaluation and/or management of the patient's health state. Selection of an interventional COA invokes pattern modifiers which evolve the patient's health state by implementing shape modifiers. These modifiers act upon the initially selected health state patterns to redefine the patient's health state or findings (e.g., a COA of insulin administration would alter the hyperglycemic finding specified in the health state descriptions for diabetes mellitus.)

As mentioned earlier, COA's also include options for further testing/diagnostic procedures. For example, the candidate might choose to select a glycosylated hemoglobin evaluation; the COA process would access the pattern for glycosylated hemoglobin instantiated at the beginning of the simulation but which might not be reported unless specifically asked for by the candidate.

A COA can modify the health state in which a patient exists at one point in time. When the candidate selects such a COA, the simulated patient evolves to a new health state patterns associated with the new health state in the knowledge base. In order to avoid "state explosion", health states closely associated with each other are represented as parallel health states not as combined health state entities.

For example, the initially generated patient for a case of osteoarthritis might demonstrate mild osteoarthritis. However, other health states, such as obesity, might influence the progress of the patient's arthritis from mild to moderate or severe disease. To avoid combinatoric health state explosion, we have implemented a concept of parallel networks of health states. In this representation, a newly-generated patient will exhibit instantiated health state patterns for the primary domain (in this case osteoarthritis) and for the parallel health states (obesity in this example) which influence the primary health state's progress.

As shown in FIG. 2, osteoarthritis can progress over time from the normal state to mild, moderate or severe osteoarthritis. For this particular illness, progress occurs in one direction only; osteoarthritis does not regress once developed, but can stabilize at a particular degree of severity. Obesity represents a parallel health state which can influence the progression of osteoarthritis. Mild, moderate, and severe obesity can influence this progress at different rates: the model permits representation of greater impact for more severe obesity states. Notice also that obesity can regress (e.g., severe obesity can revert to moderate obesity, etc.).

Any one of a number of health states might exist which could progress independently of osteoarthritis. For example, the patient who has osteoarthritis will frequently utilize non-steroidal anti-inflammatory drugs (NSAID's) for treatment. These agents can improve the symptoms of osteoarthritis, but also impact on the parallel state of peptic ulcer disease. Treatment with NSAID's can induce an ulcer, which can then evolve either on the basis of physician/examinee intervention for it, and/or for the course and treatment for other parallel health states, and time with the course and treatment of osteoarthritis.

The computer based testing system's fidelity depends upon access to a rich representation of health state-specific knowledge. This knowledge consists, as described above, in more detail below. The template includes a NAME for the health state and an associated SNOMED code. The template also includes specific descriptions of the FINDINGS, PATTERNS and SUBPATTERNS for these FINDINGS. The patterns and subpatterns are stored as a series of time and value pairs. As an example of such patterns, consider the example of Reactive Airways Disease (RAD). One finding of interest is the prevalence of RAD as a function of age, sex, and race. The prevalence for this finding appears in the knowledge base as collection of graphs illustrating the population prevalence conditioned on age, sex and race. Likewise, data such as acute exacerbation rates are represented as event rate distributions. The subpatterns also include information describing how various treatment modalities will modify the exacerbation rate and other pertinent findings such as peak expiratory flow rates and symptoms such as shortness of breath.

The present invention provides a prototypical process for developing domain-specific knowledge. The template for each domain includes, for example, the following hierarchy:

HEALTH STATE: {name assigned by the knowledge donor, e.g., "Normal Airway Reactivity"}
SNOMED CODE: {appropriate SNOMED code}
PREVALENCE: {age-sex-race specific prevalence; represented as pattern}
INCIDENCE: {age-sex-race specific incidence; represented as pattern}
FINDING: {general name for set of findings, e.g., "Asthma Attack Frequency" in reactive airways disease}
Specific Finding: {description of specific instance of a FINDING; e.g., for the FINDING of asthma attack frequency, one specific finding is "No Attacks", associated with "Normal Airway Reactivity"}

Each HEALTH STATE affects multiple FINDINGS, which in turn have Specific Findings appropriate for that FINDING in that HEALTH STATE. Data such as incidence, prevalence, and attack rates are represented as PATTERNS (graphical functions which support the patient generation simulation processes). The information is collected in paper template form, and then transferred into computer-readable format using, for example, any standard Knowledge Acquisition (KA) tool to enter the information into an object-oriented database.

The KA "front end" may be developed, for example, in the Visual Basic® and Visual C++® programming environments. Courses-of-Action (COA), such as further evaluation and/or management strategies, are entered using a standard editor that creates text files describing appropriate evaluation/management steps to support the simulation processes. The COA editor may also be designed under the Microsoft Visual environments mentioned earlier.

The knowledge acquisition step includes the following subcomponents:
A. Health state specification
B. Enumeration of FINDINGs for the health state, and agreement among the development team members
C. Population of templates with knowledge
D. Entry of health state knowledge into knowledge base using KA tool and/or direct high level pseudo-coding
E. Debugging, including generating multiple simulations, to test system stability/credibility
F. Validation including review of generated cases by representative groups of family physicians It is a feature and advantage of the present invention to: (1) allow testing at remote sites and convenient times; (2) uniformly test an expanded range of important family practice activities, with fewer questions on exotic problems; (3) adapt tests to examinees' responses or needs; and (4) create reasonable questions at test sites to simplify administrative, economic, and especially security issues.

It is another feature and advantage of the present invention to provide an approach that does not incur high maintenance costs and produces efficient and affordable scenarios for a computer-based testing system.

It is another feature and advantage of the present invention to provide a formal model of family medicine to achieve a relevant and realistic implementation of a computer based examination.

It is another feature and advantage of the present invention to provide an examination that does not require replacement with new questions in order to preserve security of the certification process.

It is another feature and advantage of the present invention to provide a computer based testing system that may measure problem-solving capabilities.

It is another feature and advantage of the present invention to provide a computer based testing system that relies upon a knowledge base of family practice which contains "patterns" and "subpatterns" which depict in probabilistic terms disease/condition incidence, prevalence, evolution over time, and response to interventions.

The present invention is based, in part, on our discovery that prior computer based testing systems suffer from various problems, including the problem that the clinical simulations are "hard-wired" in computer source code or static data structures which must be re-coded or reinstantiated for each new examination. Accordingly, in prior art computer based testing systems, once the simulation has been used widely, the examination contents are no longer secure, necessitating continuous cycles of new simulation development.

The present invention is also based, in part, on our realization that the computer based testing system needs to be capable of efficiently generating new patient cases for each candidate examined, and capable of effectively testing a candidate's problem-solving ability. We have discovered that the above may be accomplished using a knowledge base of family practice which contains "patterns" and "subpatterns" which depict in probabilistic terms disease/condition incidence, prevalence, evolution over time, and response to interventions.

To achieve the above features and advantages, as well as other features and advantages that will be apparent from the detailed description provided below, a computer implemented simulation and evaluation method simulates interventions to a patient by a user, and evaluates the interventions responsive to predetermined criteria and the interventions. The method includes defining a test area to evaluate the user on at least one predetermined criterion, selecting genetic information of the patient responsive to the test area, and generating a patient history responsive to the test area and the genetic information. The method also includes receiving at least one intervention input by the user, and evaluating the user responsive to the intervention and predetermined criteria.

In accordance with another embodiment of the invention, a computer system and computer readable tangible medium is provided that stores the process thereon, for execution by the computer.

In accordance with another embodiment of the invention, a computer readable tangible medium is provided that stores an object including the entity relationship model thereon, for execution by the computer.

It is another feature and advantage of another embodiment of the instant invention to include a method for evaluating or educating a user. The method includes the following sequential, non-sequential, or sequence-independent steps. Plurality of parallel health state networks are generated, for example, by a user or a computer. One or more first Bayesian networks, which describe each of the parallel health state networks generated by a user or a computer. One or more second Bayesian networks, which describe rates of progression within and/or between the parallel health state networks, and describe task factors that affect the rates of progression, generated by a user or a computer. One or more third Bayesian networks which support reveal structures to limit display of patient test data to patient test data specifically requested by the user, are generated by a user or a computer. One or more fourth Bayesian networks which support plan critiques of queries of and treatment prescribed by the user, are generated by a user or a computer.

A knowledge base is scripted by the computer from the one or more first Bayesian networks and the one or more second Bayesian networks. A model patient, at least in part, is instantiated by the computer from the scripted knowledge base. A course of action or a query for a specific medical finding concerning the model patient is received by the computer from the user responsive to the instantiated model patient. If the query is received, the specific medical finding is displayed by the computer to the user based at least in part on the one or more third Bayesian networks, and repeating the receiving step.

The model patient is evolved by the computer in accordance with the parallel health state networks and responsive to the received course of action. The receiving, displaying, and evolving steps are repeated by the computer until the user has completed treatment of the model patient. An optimum combination of treatment and queries based, at least in part, on the one or more fourth Bayesian networks and the instantiated model patient is generated by the computer. The query and the treatment by the user is evaluated by the computer in comparison to the generated optimum combination of treatment and queries.

Optionally, the parallel health state networks describe primary networks defining disease evolutions, secondary networks defining risk factors affecting progression through a particular or given primary network of the plurality of primary networks, and/or tertiary networks defining causal probabilistic medical complications attributed to one or more stages in the primary network and/or medical complications attributed to management of the one or more stages.

It is another feature and advantage of the instant invention to provide a computer readable medium including instructions being executed by a computer. The instructions instruct the computer to execute an educational or testing system for physicians. The instructions include the following sequential, non-sequential, or sequence-independent steps. One or more first belief networks which describes parallel health state networks are accessed, for example, by a computer. A knowledge base, at least in part, is scripted from the one or more first belief networks by the computer. A model patient, at least in part, is instantiated by the computer from the scripted knowledge base. Optionally, for the computer readable medium, the parallel health state networks describe primary networks defining disease evolutions, secondary networks defining risk factors affecting progression through a primary network of the plurality of primary networks, and/or tertiary networks defining causal probabilistic medical complications attributed to at least one stage in the primary network and/or medical complications attributed to management of the one or more stages.

Optionally, the instructions further include one or more second belief networks, which describe rates of progression within and/or between the parallel health state networks, and describe task factors that affect the rates of progression, are accessed by the computer or the user. Optionally, one or more third belief network, which supports reveal structures to limit display of patient test data to patient test data specifically requested by the user, are accessed, for example, by the computer. Optionally, one or more fourth belief networks which support plan critiques of queries of and treatment prescribed by the user, are accessed by the user or the computer. Optionally, the scripting step includes scripting the knowledge base by the computer, at least in part, from the one or more second belief networks. Optionally, a course of action or a query for a specific medical finding concerning the model patient is received by the computer from the user responsive to the instantiated model patient. If the query is received, the specific medical finding is displayed by the processor to the user based at least in part on the at least one third network, and the receiving step is repeated by the processor.

Optionally, the model patient is evolved by the computer in accordance with the parallel health state networks and responsive to the received course of action. Optionally, the receiving, displaying, and evolving steps are repeated by the computer until the user has completed treatment of the model patient. Optionally, an optimum combination of treatment and queries is generated by a processor based on the one or more fourth belief networks and the instantiated model patient. Optionally, the query and the treatment by the user are evaluated by the computer in comparison to the generated optimum combination of treatment and queries.

It is another feature and advantage of the instant invention to include a system for evaluating or educating a user. The system includes means for scripting a knowledge base from at least one first belief network and at least one second belief network. The system includes means for instantiating a model patient, at least in part, from the scripted knowledge base. The system includes means for receiving a course of action or a query for a specific medical finding concerning the model patient from the user responsive to the instantiated model patient. The system includes means for displaying, if the query is received, the specific medical finding to the user based at least in part on at least one third belief network, and activating the receiving means.

The system includes means for evolving the model patient in accordance with the at least one first belief network and the at least one second belief network and responsive to the received course of action. Optionally, the system includes means for communicating with the receiving means, the displaying means, and the evolving means until the user has completed treatment of the model patient.

Optionally, the system includes means for generating an optimum combination of treatment and queries based on at least one fourth belief network and the instantiated model patient. Optionally, the system includes means for evaluating the query and the treatment by the user in comparison to the generated optimum combination of treatment and queries.

Optionally, the system includes means for generating parallel health state networks describing primary networks defining disease evolutions, secondary networks defining risk factors affecting progression through a primary network of the plurality of primary networks, and/or tertiary networks defining causal probabilistic medical complications attributed to at least one stage in the primary network and/or medical complications attributed to management of the at least one stage.

Optionally, the system includes means for generating the at least one first belief network which describes each of the plurality of parallel health state networks. Optionally, the system includes means for generating the at least one second belief network which describes rates of progression within and/or between the parallel health state networks, and describes task factors that affect the rates of progression. Optionally, the system includes means for generating the at least one third belief network which support reveal structures to limit display of patient test data to patient test data specifically requested by the user. Optionally, the system includes means for generating the at least one fourth belief network which supports plan critiques of queries of and treatment prescribed by the user.

It is another feature and advantage of the instant invention to include an expert system. The expert system includes a processor. The expert system also includes a computer-readable medium storing instructions executable by the processor.

The instructions include the following sequential, non-sequential, or sequence-independent steps. Parallel health state networks are accessed by the processor and which describe primary networks defining disease evolutions, secondary networks defining risk factors affecting progression through a primary network of the plurality of primary networks, and/or tertiary networks defining causal probabilistic medical complications attributed to at least one stage in the primary network and/or medical complications attributed to management of the at least one stage.

One or more first belief networks, which describe each of the plurality of parallel health state networks, are accessed by the processor. One or more second belief networks, which describe rates of progression within and/or between the parallel health state networks, and describe task factors that affect the rates of progression, are accessed by the processor. One or more third belief networks, which support reveal structures to limit display of patient test data to patient test data specifically requested by the user, are accessed by the processor. One or more fourth belief networks, which support plan critiques of queries of and treatment prescribed by the user, are accessed by the processor. Patient data for an actual patient is received by the processor by user input.

A virtual patient having characteristics consistent with the received patient data and based, at least in part, on the at least one first belief network and the at least one second belief network is instantiated by the processor. A query for a specific medical finding concerning the actual patient, or a course of action responsive to at least one normal or abnormal health state of the plurality of health states of the virtual patient is generated by the processor. The normal or abnormal health state corresponds to at least part of the received patient data. The specific medical finding from the user, if a query therefor is generated.

The virtual patient is evolved by the processor in accordance with the at least one first belief network and/or the at least one second belief network, and responsive to the received specific medical finding and/or the generated course of action. Optionally, the instructions for the expert system further includes repeating the generating, receiving, and evolving instruction steps until the user has dispensed treatment of the actual patient based on the generating course of action. Optionally, the instructions further include storing the evolved virtual patient for subsequent access by the user, and repeating the generating, receiving, evolving, repeating, and storing instruction steps upon each subsequent access by the user at least until the treatment of the actual patient is completed.

It is another feature and advantage of the instant invention to include a system for educating or evaluating a user. The system includes a model patient generator including a knowledge base scripted from one or more first causal probability networks, one or more second causal probability networks. The one or more first causal probability networks describe each parallel health state network of a plurality of parallel health state network. The one or more second causal probability networks describe at least one rate of progression within and/or between the parallel health state networks, and which describe at least one task factor that affects the one rate of progression. The patient generator instantiates, upon user input, a model patient in a whiteboard, at least in part, from the scripted knowledge base. The patient generator receives a course of action or a query for a specific medical finding concerning the model patient from the user responsive to the instantiated model patient. The whiteboard optionally displays, if the query is received, the specific medical finding to the user based, at least in part, on at least one third belief network, which supports patient health state reveal structures. The whiteboard evolves the model patient in accordance with the plurality of parallel health state networks and responsive to the received course of action.

It is another feature and advantage of the instant invention to include a system communicatable with a computer network. The system includes a server communicatable with a user via the computer network. The server is in communication with a processor and a computer-readable medium storing instructions executable by the processor. The instructions include the following sequential, non-sequential, or sequence-independent instruction steps. Parallel health state networks are accessed by a user or the processor and which describes primary networks defining disease evolutions, secondary networks defining risk factors affecting progression through a primary network of the plurality of primary networks, and/or tertiary networks defining causal probabilistic medical complications attributed to one or more stage in the primary network and/or medical complications attributed to management of the one or more stage.

One or more first belief networks, which describe each of the plurality of parallel health state networks, are accessed by the user or the processor. One or more second belief networks which describe rates of progression within and/or between said plurality of parallel health state networks, and to describe task factors that affect the rates of progression, are accessed by the user or the processor. One or more third belief networks, which supports plan critiques of queries of and treatment prescribed by the user, are accessed by the user or the processor.

Patient data for an actual patient are received by user input to the processor. A virtual patient, having characteristics consistent with the received patient data and based, at least in part, on the one or more first belief networks and the one or more second belief networks, is instantiated by the processor. A query to the user for a specific medical finding concerning the actual patient, or a course of action based, at least in part on the virtual patient and the one or more third belief networks are generated by the processor. The specific medical finding is received by the processor from the user responsive to the generated query. The virtual patient is evolved by the processor in accordance with the one or more first belief network and/or the one or more second belief network, and responsive to the received specific medical finding.

Optionally, the instructions of expert system further include repeating the generating, receiving, and evolving instructions steps until the user has dispensed treatment of the actual patient based on the generating course of action. Optionally, the evolved virtual patient is stored by the processor for subsequent access by the user. Optionally, the generating, receiving, evolving, repeating, and, storing instructions are repeated by the computer upon each said subsequent access by the user at least until the treatment of the actual patient is completed.

It is another feature and advantage of the instant invention to include a system communicatable with a computer network. The system includes a server communicatable with a user via the computer network. The server is in communication with a processor and a computer-readable medium storing instructions executable by the processor.

The instructions include the following sequential, non-sequential, or sequence-independent instruction steps. Optionally, parallel health state networks are accessed by the processor or a user and which describe primary networks defining disease evolutions, secondary networks defining risk factors affecting progression through a primary network of the primary networks, and/or tertiary networks defining causal probabilistic medical complications attributed to one or more stages in the primary network and/or medical complications attributed to management of the one or more stages.

One or more first belief networks which describe each of the plurality of parallel health state networks are accessed. One or more second belief networks, which describe rates of progression within and/or between said plurality of parallel health state networks, and describe task factors that affect the rates of progression, are accessed. One or more third belief networks, which support reveal structures to limit display of patient test data to patient test data specifically requested by the user, are accessed. One or more fourth belief networks, which supports plan critiques of queries of and treatment prescribed by the user, are accessed. A knowledge base is scripted by the processor or a user from the one or more first belief networks and the one or more second belief networks.

A model patient is instantiated by the processor, based, at least in part, from the scripted knowledge base. A course of action or a query for a specific medical finding concerning the model patient is received by the processor from the user responsive to the instantiated model patient. If the query is received by the processor, the specific medical finding is displayed by the processor to the user based at least in part on the one or more third belief networks, and repeating the receiving instruction. The model patient is evolved by the processor in accordance with at least one of the one or more first belief networks and the one or more second belief networks and responsive to the received course of action.

Optionally, the instructions further include repeating by the processor the receiving, displaying, and evolving instructions until the user has completed treatment of the model patient. Optionally, an optimum combination of treatment and queries is generated by the processor based on the one or more fourth belief networks and the instantiated model patient. Optionally, the query and the treatment by the user is evaluated by the processor in comparison to the generated optimum combination of treatment and queries.

It is a feature and advantage of another embodiment of the instant invention to include a knowledge base module for an educational or testing system or an expert system. The knowledge base module includes one or more first causal probability networks, which describe each parallel health state network of a plurality of parallel health state networks. The module includes one or more second causal probability networks, which describe one or more rates of progression within and/or between the parallel health state networks, and which describe one or more task factors that affect the one or more rates of progression. The module also includes one or more third causal probability networks, which describe plan critiques including peer-accepted courses of action for addressing the parallel health state networks.

It is a feature and advantage of another embodiment of the instant invention to include a computer network appliance. The network appliance includes a thin client programmably connected via a computer network to a single web hosting facility. The single web hosting facility includes a server communicatable with a user via the computer network. The server is in communication with a processor and a computer-readable medium storing instructions executable by the processor.

The instructions include the following sequential, non-sequential, or sequence-independent instruction steps. Parallel health state networks describing primary networks defining disease evolutions, secondary networks defining risk factors affecting progression through a primary network of the plurality of primary networks, and/or tertiary networks defining causal probabilistic medical complications attributed to at least one stage in the primary network and/or medical complications attributed to management of the at least one stage are accessed by the user or the processor.

One or more first belief networks, which describe each of the parallel health state network, are accessed by the user or the processor. One or more second belief networks, which describe rates of progression within and/or between said plurality of parallel health state networks, and describe task factors that affect the rates of progression, are accessed by the user or the processor. One or more third belief networks, which support reveal structures to limit display of patient test data to patient test data specifically requested by the user, are accessed by the user or the processor. One or more fourth belief networks, which supports plan critiques of queries of and treatment prescribed by the user, are accessed by the user or the processor.

A knowledge base from the one or more first belief networks and/or the one or more second belief networks is scripted by the processor. A model patient, at least in part, is instantiated from the scripted knowledge base by the processor. A course of action or a query for a specific medical finding concerning the model patient is received by the processor from the user responsive to the instantiated model patient. If the query is received, the specific medical finding is displayed by the processor to the user based in part on the one or more third belief networks, and repeating the receiving instruction step. The model patient is evolved by the processor in accordance with the parallel health state networks and responsive to the received course of action.

Optionally, the instructions for the computer network appliance repeating the receiving, displaying, and evolving instruction steps until the user has completed treatment of the model patient. Optionally, the instructions include generating an optimum combination of treatment and queries based on the one or more fourth belief networks and the instantiated model patient, and evaluating the query and the treatment by the user in comparison to the generated optimum combination of treatment and queries.

It is a feature and advantage of another embodiment of the instant invention to include a computer network appliance. The computer network appliance includes a thin client programmably connected via a computer network to a single web hosting facility. The single web hosting facility includes a server communicatable with a user via the computer network. The server is in communication with a processor and a computer-readable medium storing instructions executable by the precessor.

The instructions include the following sequential, non-sequential, or sequence-independent instruction steps. Parallel health state networks describing primary networks defining disease evolutions, secondary networks defining risk factors affecting progression through a primary network of the plurality of primary networks, and/or tertiary networks defining causal probabilistic medical complications attributed to at least one stage in the primary network and/or medical complications attributed to management of the at least one stage, are accessed by the user or the process. One or more first belief networks, which describes each of the parallel health state networks, are accessed by the user or the processor. One or more second belief networks, which describe rates of progression within and/or between said plurality of parallel health state networks, and describe task factors that affect the rates of progression, are accessed by the user or the processor. One or more third belief networks which support plan critiques of queries of and treatment prescribed by the user, are accessed by the user or the processor.

Patient data for an actual patient are received by user input. A virtual patient having characteristics consistent with the received patient data and based, at least in part, on the one or more first belief networks and/or the one or more second belief networks are instantiated by the processor.

A query to the user for a specific medical finding concerning the actual patient, or a course of action based, at least in part on the virtual patient and the one or more third belief networks are generated by the processor. The specific medical finding is received by the processor from the user responsive to the generated query. The virtual patient is evolved by the processor in accordance with the one or more first belief networks and/or the one or more second belief networks, and responsive to the received specific medical finding.

The instructions for the optionally expert system further include repeating the generating, receiving, and evolving instruction steps until the user has dispensed treatment of the actual patient based on the generating course of action, and storing the evolved virtual patient by the processor for subsequent access by the user. Optionally, the generating, receiving, evolving, repeating, and storing instruction steps are repeated by the processor upon each said subsequent access by the user at least until the treatment of the actual patient is completed.

It is a feature and advantage of another embodiment according to the instant invention to include a system communicatable with a computer network. The system includes a server communicatable with a user via the computer network. The server is in communication with a processor and a computer-readable medium storing instructions executable by the processor.

The instructions include the following sequential, non-sequential, or sequence-independent steps. Parallel health state networks, describing primary networks defining disease evolutions, secondary networks defining risk factors affecting progression through a primary network of the plurality of primary networks, and/or tertiary networks defining causal probabilistic medical complications attributed to at least one stage in the primary network and/or medical complications attributed to management of the at least one stage, are accessed by the processor or a user.

One or more first belief networks, which describe each of the plurality of health states in parallel networks, are accessed by the processor or a user. One or more second belief networks, which describe transitions between health states within parallel networks, and describe task factors that affect the rates of progression, are accessed by the processor or a user. One or more third belief networks, which support reveal structures to limit display of patient test data to patient test data specifically requested by the user, are accessed by the processor or a user. One or more fourth belief networks, which support plan critiques of queries of and treatment prescribed by the user, are accessed by the processor or a user.

A knowledge engineer, such as a developer or a standard data mining process, scripts a knowledge base by specifying one or more first belief networks and/or the one or more second belief networks. A model patient is instantiated by the processor based, at least in part, from the scripted knowledge base. A course of action or a query for a specific medical finding concerning the model patient is received by the processor from the user responsive to the instantiated model patient. If the query is received, the specific medical finding is displayed by the processor to the user based at least in part on the one or more third belief networks, and repeating the receiving instruction step. The model patient is evolved by the processor in accordance with the one or more first belief networks and/or the one or more second belief networks and responsive to the received course of action.

Optionally, the instructions further include repeating the generating, receiving, and evolving instruction steps until the user has dispensed treatment of the actual patient, at least in part, based on the generated course of action, and storing the evolved virtual patient by the processor for subsequent access by the user. Optionally, the generating, receiving, evolving, repeating, and storing instruction steps are repeated by the processor upon each subsequent access by the user at least until the treatment of the actual patient is completed.

It is a feature and advantage of another embodiment of the instant invention to include a method for educating or evaluating a user. The method includes the following sequential, non-sequential, or sequence-independent steps. A virtual patient is instantiated for display to the user, for example, by a computer. The virtual patient includes a number of health states. A query is received from the user for a medical finding concerning the instantiated virtual patient. Optionally, responsive to the received query, a specific medical finding is generated at least in part from a first causal probabilistic network defining a health state reveal structure corresponding to the instantiated virtual patient. Optionally, responsive to the received query, an indication of an inappropriate query is generated based, at least in part, on a second causal probabilistic network defining a medical practice management plan. By way of illustration, the medical practice management plan includes healthcare provider or medical insurance-approved medical finding queries.

It is a feature and advantage of another embodiment of the instant invention to include a method for educating or evaluating a user. A virtual patient is instantiated by a computer for display to the user. The virtual patient includes a plurality of health stages. A query for a medical finding concerning the instantiated virtual patient is received by the computer. Responsive to the received query, a specific medical finding is generated by the computer, at least in part, from a first causal probability network defining a health state reveal structure corresponding to the instantiated virtual patient. Responsive to the received query, an indication of an inappropriate query, based, at least in part, on a second causal probability network defining a medical practice management plan. Responsive to the received course of action, an indication of an inappropriate course of action by the computer based, at least in part, on the second causal probability network. Optionally, the medical practice management plan includes healthcare insurer approved medical finding queries. Advantageously, such a method is used to familiarize doctors new to a health care plan with management approved medical tests and/or medical procedures.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

The above objects of the invention, together with other apparent objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter forming a part hereof, wherein like numerals refer to like elements throughout, and in which there is illustrated preferred embodiments of the invention.

NOTATIONS AND NOMENCLATURE

Figure 1:
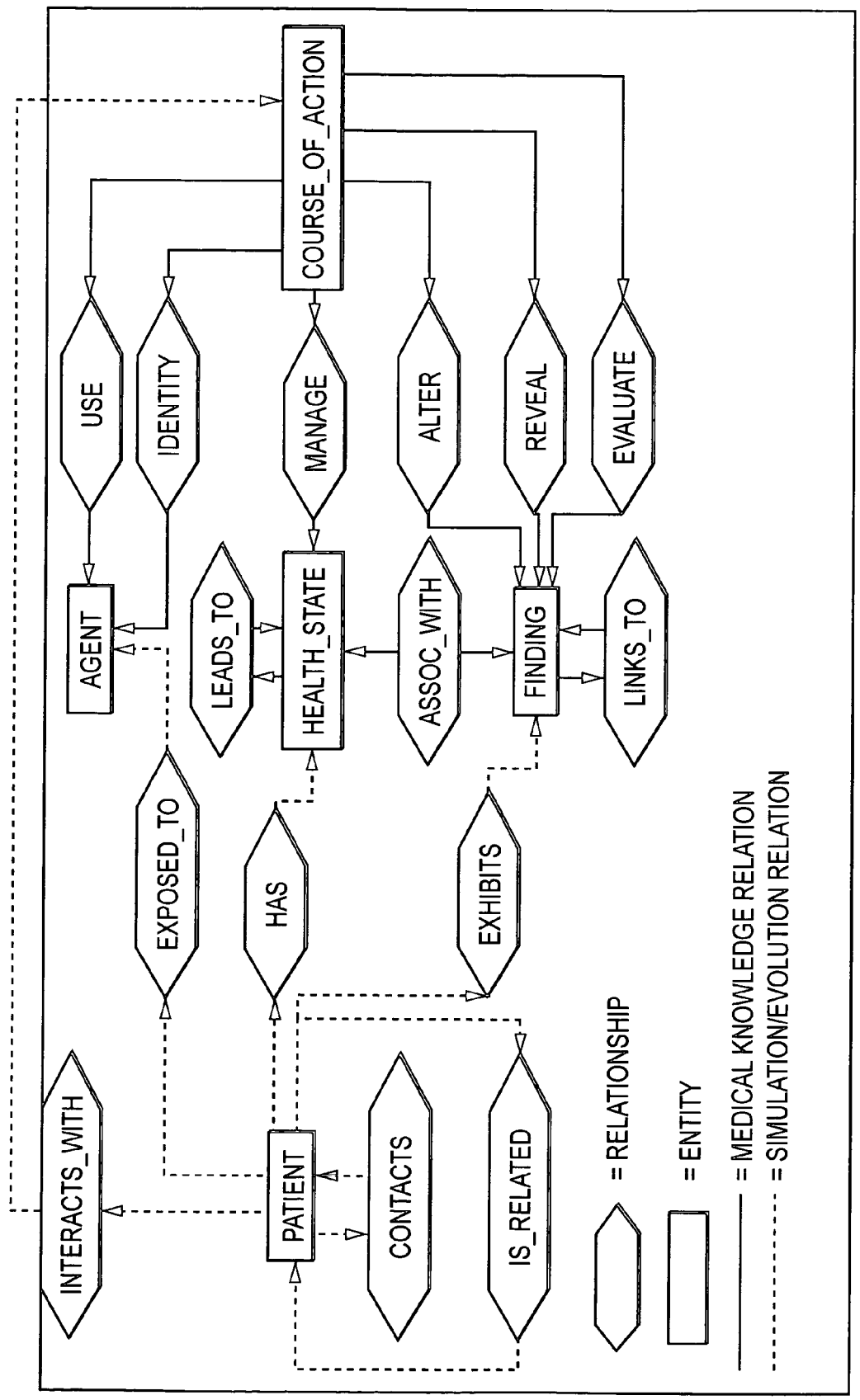
FIG. 1 is a diagram describing an overall or conceptual view of the entities and relationships in the model used in the computer based examination system of the present invention.
Figure 2:
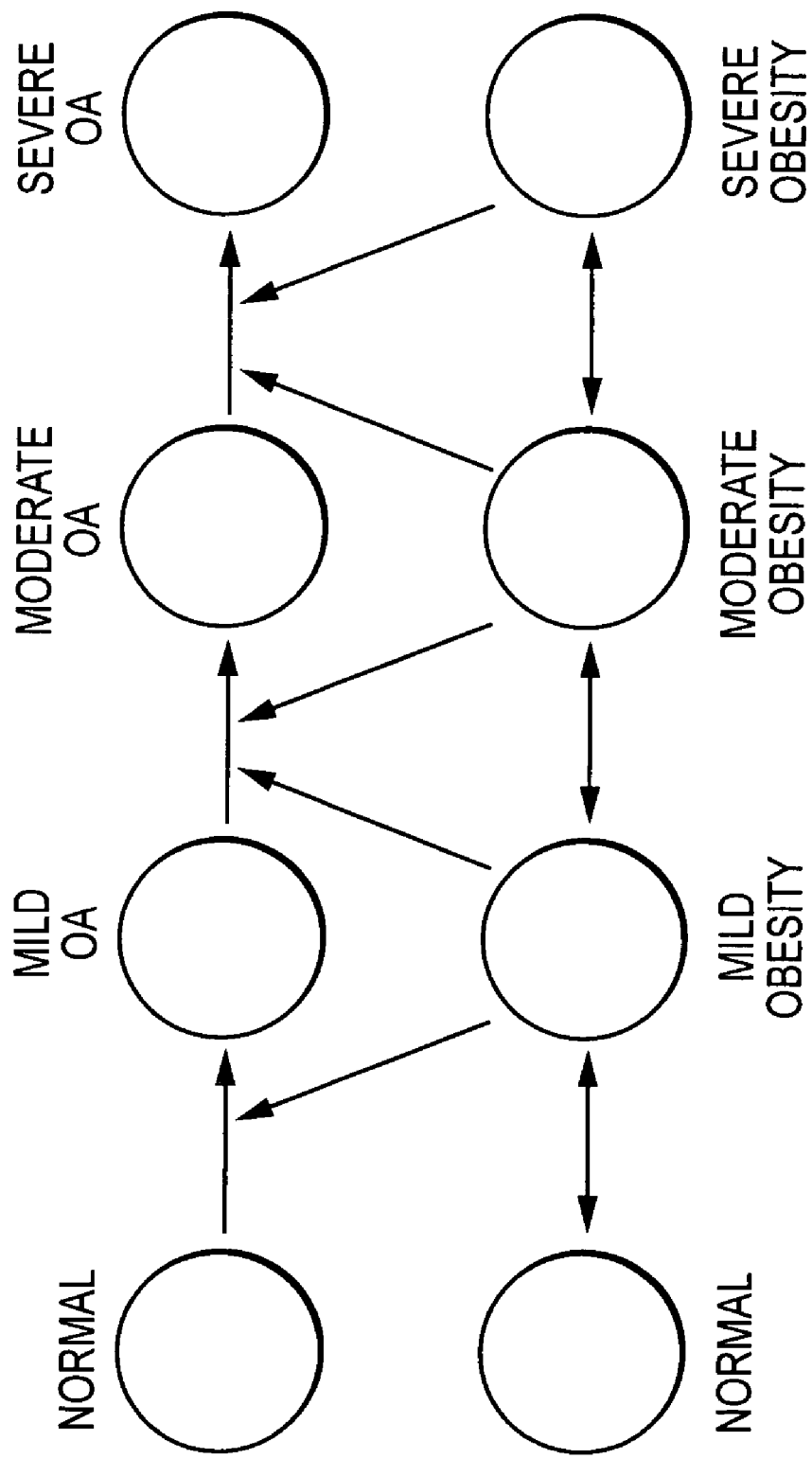
FIG. 2 is a diagram describing the progression of osteoarthritis over time from the normal state to mild, moderate or severe states of osteoarthritis.

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

BEST MODE FOR CARRYING OUT THE INVENTION

The computer-based testing system described herein represents knowledge at multiple levels of complexity.

The computer-based testing system of the present invention partitions knowledge into fundamental types: Health States, Agents, Findings, Specific Findings, Patterns and Sub-patterns describe system behaviors and characteristics. Courses-of-Action describe tasks and methods used to apply, modify, and evaluate the health state information and characteristics described in the model. Subdivision of knowledge types in this manner facilitates the knowledge acquisition process. This subdivision also promotes multiple levels of knowledge abstraction, which enhances the system's ability to represent varying levels of complexity.

For example, reactive airways disease is represented as a series of health states: Normal (Non-reactive) Airways, Reactive Airways-Mild, Reactive Airways-Moderate, and Reactive Airways-Severe. Each health state contains identifiers which relate the particular health state to precedents and antecedents (e.g., Normal Airways serves as the precursor health state for Mild Reactive airways disease, and Mild, Moderate and Severe Reactive Airways Disease represent target or sequential successor health states from the Normal circumstance.)

Each health state in turn has associated findings, and specific findings. For example, in the Normal Airways state, "Asthma Attack Frequency" appears as a Finding which is instantiated with the Specific Finding "No attacks." Similarly, other Findings such as Respiratory Function and Severe Asthma Attach Frequency are instantiated with corresponding normal Specific Findings (Normal Respiratory Functions, and No Severe Attacks.) This representation transports to each new health state in, what we have determined to be somewhat analogous to diagnosis.

Advantageously, the Computer-Based Testing System of the present invention in the knowledge acquisition process uses direct questioning in querying family practice physicians regarding their knowledge of and approaches to specific knowledge domains (such as osteoarthritis). Additionally, knowledge acquisition has included access to appropriate scientific literature, which functionally serves to provide an ethnographic assay of actual practice.

Overview of Testing/Recertification Process

The testing and/or recertification process, for example, unfolds as follows. After initial certification, examinees initiate recertification software on workstations on computer systems. The examinee begins recertifying at any convenient time and could suspend the examination at the conclusion of any simulated patient encounter. The software of the present invention presents a patient by using text, illustrations, still pictures, and video. The examinee questions and examines the simulated patient, reaches conclusions about the situation, and suggests treatment options. The simulated patient may express preferences about these options.

After receiving a treatment plan, the patient leaves, maybe follows the plan, and perhaps later returns for follow-up. In the meantime, the examinee sees other simulated patients. To discourage cheating, the software offers so many cases that a diplomate observing another examinee recertify gains little advantage with regard to test content.

The present invention maintains records of the information gathered, the hypotheses entertained, and the recommendations made for each patient. After monitoring performance on several similar cases (for instance, cases involving diagnosis and management of adult-onset diabetes mellitus), the program draws conclusions about the physician's ability to handle this class of problems. If competence has been demonstrated, the class of problems may be removed from further consideration for several years. Until competence has been demonstrated, the physician receives feed-back on specific areas for improvement and continues to see cases from this class of problems.

The testing and/or recertification process could eventually become a continuous learning experience at the office or home. Some recertification activities might qualify as continuing medical education, partially offsetting the time needed to recertify. Examinees could anticipate failure to recertify and take corrective measures years before actually failing.

The present invention provides an approach that does not incur high maintenance costs to maintain efficient and affordable examinations. The present invention also provides a formal model of family medicine to achieve a relevant and realistic implementation of this kind of computer-based examination.

In general, a model describes the kinds of information that could be collected regarding a topic. For instance, a model of a mailing address should include at least a name, street address, apartment number, city, state, and ZIP code. A database built upon this model could list these items for each entry. Not every item in the model should be described for every entry in the database; many addresses have no apartment number. Incomplete database entries still provide useful information; even if a street address is missing, the city to search can be found.

Finally, the model limits what the database could do; it could not easily list first names. A model of diagnostic medicine of the present invention includes diseases, historical and examination data, and links between diseases and data. These models represent knowledge that physicians apply to uncertain or imprecise cases. The address example suggests a list of simple observations, called a database. A diagnostic program uses a collection of more abstract information, such as a statistical summary of a database, to draw inferences about a single case. The program and its information are often called a knowledge base.

We have determined that a well-designed formal model supports automatically created case simulations, reducing the long-term cost of writing cases by hand and improving security. The formal model of the present invention considers that medicine is full of diagnostic complexities including disease interaction. Thus, diabetes could change the severity of pain experienced during an acute myocardial infarction. With this information, the knowledge base of the present invention is able to support a realistic simulation process—a simulated diabetic having an acute myocardial infarction will experience a specific discomfort. The present invention attempts to carefully define interactions for a number of health states that constitute the bulk of family medicine.

We have further determined that diagnosis and patient management are inextricably linked to time. Time receives relatively little attention in many knowledge bases and is often summarized very succinctly. For instance, a knowledge base might describe "chest pain lasting more than 30 minutes" as a symptom of acute myocardial infarction. This knowledge base could misinterpret 29 minutes of chest pain as evidence against acute myocardial infarction, and 2 years of chest pain as an indicator of acute myocardial infarction. The present invention also supports the related concepts of continuity of care and observation.

In addition to these problems, family physicians deal with a host of issues that we have determined are not routinely modeled in diagnostic software. Most of these issues reflect the overwhelming importance of patient management in family medicine.

First, family medicine occurs in a social context that is often ignored in computer-generated simulations. Knowledge bases do not model social interactions or family structure.

Second, family practice patients arrive with attitudes shaped by experience, and physicians must adjust their strategies to cope with those attitudes. Adjustments range from changing interview style to altering treatments. Variability in patient attitudes limits the likelihood that there exists one best answer for groups of patients with similar medical conditions.

Third, family physicians emphasize helping patients improve the length and quality of their lives. Family physicians spend considerable time reassuring worried patients, alleviating symptoms, and preventing the onset or progression of disease.

We have determined that the final testing and/or recertification problem, evaluating the responses of diplomates, also requires a model of what family physicians do. All dichotomous evaluations, especially pass-fail tests, use arbitrary standards. The challenge is to set standards using generally agreeable and meaningful criteria. The present invention provides the flexibility to determine to whom the criteria should be agreeable—certainly to diplomates, but perhaps also to patients, insurers, or other customers. Specifying these customers will help establish meaningful criteria for certification decisions.

For instance, diplomates have an interest in maintaining respected credentials, patients want effective care, insurers desire low costs, and public health advocates have an interest in clinical guidelines. It is not at all clear how to respond to these diverse interests. The present invention delivers flexible models to describe the consequences of family practice activities, as seen by various parties, so that board certification remains a pertinent process regardless of changes in the health care system.

We have determined that a model is needed to describe the scope of family medicine in epidemiologic terms, while including the information about individual variation that differentiates individualized patient care from public health. The model will be the foundation of a family practice knowledge base storing data about family medicine. The model also supports other applications of benefit to family physicians. Specific software applications might involve medical records, structured vocabularies, medical reference tools, decision support systems, and continuing education programs.

Data structures to describe the activities of family physicians include a series of entity-relation diagrams. In an entity-relation diagram, entities usually represent things (nouns). The relations (verbs) illustrate how the entities interact. For instance, an entity-relation diagram of an address list might have an entity called "person," and an entity called "place," connected by a relation called "is at." One could read this diagram, "person is at place." The person entity would store people's names, the place entity would store addresses, and the "is at" relation would describe when and why this person is at that place. Thus, a person could now live at one place, previously live at another place, and continuously work at the first place. One person, two places, and three "is at" relations describe this address history. This address model is flexible and realistic.

We have determined that an important class of events exist in the model of family medicine, which we call "modifying relations," or modifiers. In database terms, modifiers are relations between traditional relations. Modifiers extend the conventional entity relation diagram and provide a means of managing statistically dependent events.

Model Structure

Figure 3:
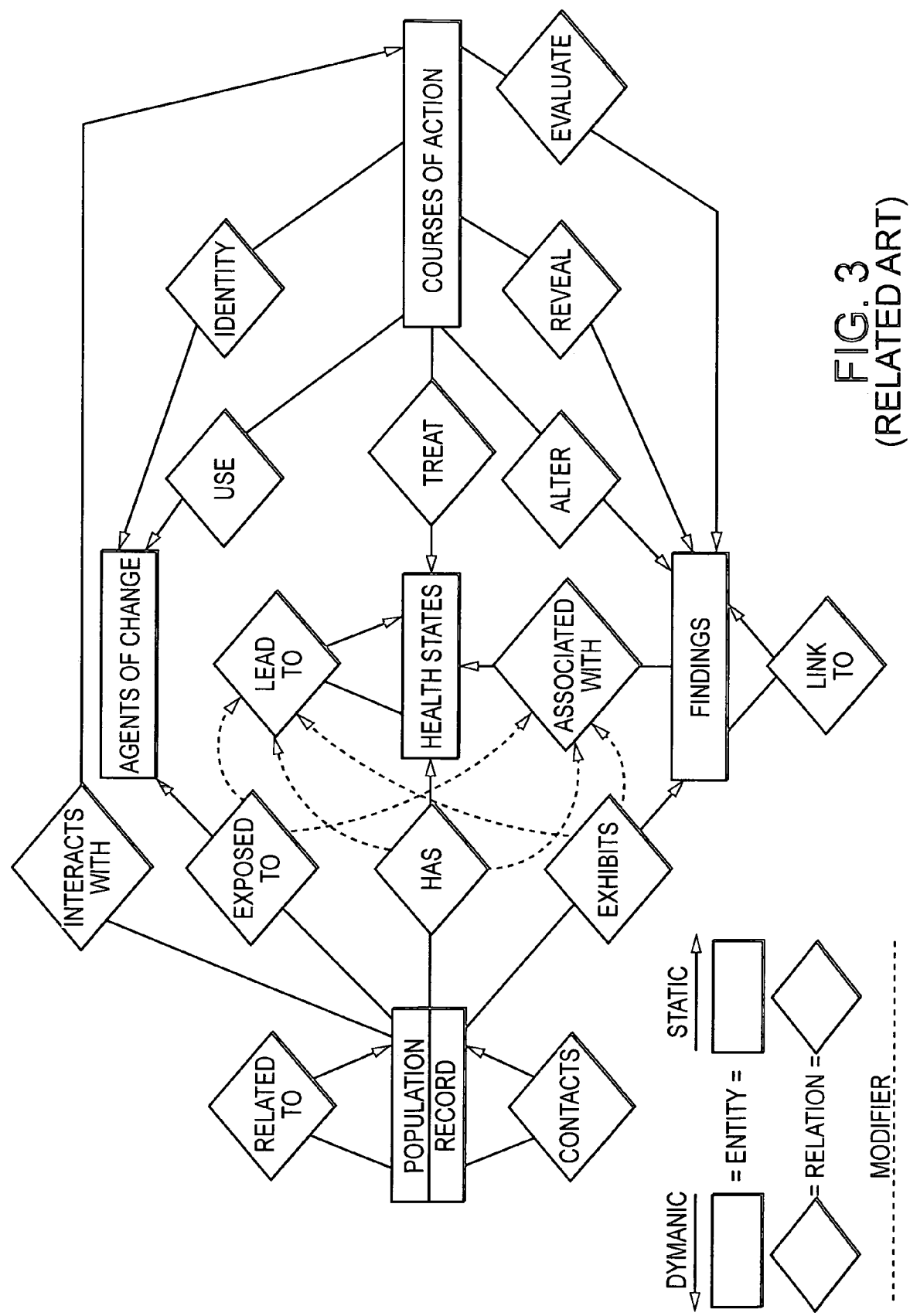
FIG. 3 is a detailed diagram of the family medicine model, including the major entities, relations and modifying relations.

The family medicine model includes the major entities, relations and modifying relations shown in detail FIG. 3. Formal concepts in the model are capitalized throughout the text. The model emphasizes diagnostic and management issues, variability in populations, and time. It describes consequences of anatomic and physiologic processes, but largely omits anatomic and physiologic reasoning as such. It is also capable of describing interpersonal relationships and is expendable to include an explicit representation of families or communities.

Modifiers (for example, Bayesian network from a Lead to relation, Bayesian network describing risk factors for progression, and the like) are relations that might change values in other relations. Dynamic entities and relations contain information relevant to patient simulations. Dynamic information for an individual patient is derived from data in other dynamic and static entities and relations. The dynamic Record entity has relations mirroring the Population's relations. Static entities and relations contain the best available medical knowledge, similar to data in medical literature.

The following major entities appear in the design: Populations, Records, Health States, Findings, Courses of Action, and Agents of Change.

Populations represent real humans; their relations should precisely describe all data that physicians consider. Populations can be large groups with a shared characteristic, such as white males or single-parent families. An individual patient is a Population of 1; a pregnant woman is a Population of 2; a nuclear family with 2 children and 2 parents is a Population of 4.

Records model beliefs about people; a Record's relations summarize inferences about a Population. If a parent brings an infant to the office, this design represents the infant as a Population, the parent as another Population, and the parent's description of the infant as a Record. The physician can obtain historical information about the infant from two sources: the physician's medical Record of the infant, and the parent's Record of the infant. The physician can obtain current objective information by examining the infant as a Population. The data linked to Populations are absolutely precise, but can be observed, if at all, only during medical encounters. Records summarize the history of those real data imprecisely and potentially inaccurately.

Populations have Records of themselves, modeling a patient's self-image and memories. As with other Records, a patient's self-Record summarizes historical information with variable accuracy and might be the physician's only source of some historical information.

A Population is primarily a list of relations with other entities. A Record not only lists relations with other entities, but also defines encounters during which these relations were discovered. A Record can contain conflicting data acquired at different encounters.

Health States include all normal health states; classic disease presentations; early, subtle, or late disease presentations; and some disease combinations. Health States also include groups of Health States with shared characteristics, such as cardiovascular diseases and diseases of glucose intolerance. The SysteMetrics Corporation publishes Disease Staging Clinical Criteria, which define numerous stages in the development of diseases. See, for example, Gonella J S, Louis D Z, Gozum M E, editors, Disease staging clinical criteria, 4th ed. Ann Arbor, Mich.: MEDSTAT Systems, 1994, incorporated herein by reference.

Each of these stages represents a distinct Health State entity in this design. The SysteMetrics staging of diabetes mellitus defines stage 1.1 as asymptomatic diabetes, stage 1.2 as symptomatic diabetes, stage 1.3 as type I diabetes mellitus, and stage 2.1 as diabetes with end-organ damage. Each of these stages defines at least one Health State by the presence of specific objective criteria.

Stage 2.1 might be divided into a group of Health States representing each damaged end organ. To represent multiple end organ damage, one might simply superimpose these states.

Findings include genetic, physiologic, symptomatic, physical, and test-generated data, and clusters of such data. For instance, musculoskeletal chest pain could be a Finding. This Finding could be an example of a Finding called chest pains, which would represent all kinds of chest pains. Chest pains could be an example of a still larger Finding called symptoms. Findings are defined by a collection of one or more Features, whose current value can be described by a number on a scale. One Feature pertinent to pain is severity, which might be described on a 10-point scale.

Structures called Patterns describe the possible values of each Feature over time. A Pattern typically lists a series of values and corresponding percentiles at several points in time. Pediatric growth charts are the most widely used real example of Patterns. A blank growth chart illustrates at least the following observations: (1) Normal birth weights vary within a narrow range. (2) Weight increases relatively rapidly in the first few months and years. (3) The absolute variation in weight (e.g., the difference between 90th and 10th percentile weights) increases after birth. (4) Most people reach a fairly constant weight by early adulthood. A pattern listing 10th and 90th percentile weights for people at age 0, 1 year, 2 years, and so on, illustrates the same concepts.

Growth charts also predict future values from past information. A child at the 50th percentile for weight now is expected to stay near the 50th percentile. If this child later reaches the 5th percentile of weight, the expected pattern is absent. The ensuing diagnostic evaluation is an effort to account for the deviation by finding a weight Pattern that explains all observations. These concepts extend easily to many other values, such as temperature. People have an average temperature of about 37° C., but some are a little cooler and some a little warmer. Normal temperature fluctuates within a narrow range during a lifetime, and most deviations from that range are considered abnormal.

Another example would be ST segments on a electrocardiogram. Following an acute myocardial infarction, ST segments usually rise by varying amounts, fall, and return to normal. The ST segment deviation from base line varies with time and can be described by a Pattern, similar to the variation in weights of growing children.

Many values change in predictable ways. Patterns might have cycles, sub-Patterns, and sub-sub-Patterns to describe these changes. The average value of a variable often changes during a lifetime, while the instantaneous value depends on a combination of annual, lunar, and circadian cycles. For instance, a nonpregnant 20-year-old woman should experience predictable lunar and circadian temperature fluctuations.

Sub-Patterns also describe consequences of other events, such as taking a drug. For instance, a dose of acetaminophen might lower a fever for 4 hours. A fever responsive to acetaminophen could be modeled by a high-temperature Pattern with a sub-Pattern indicating 4 hours of normal temperatures following acetaminophen doses. A person experiencing this fever and taking acetaminophen every 4 hours maintains a normal temperature. A physician observing this temperature Pattern would need to halt the acetaminophen to distinguish between a normal temperature and fever responsive to acetaminophen.

Sub-Patterns characterize Features and therefore Findings. For instance, one of the chest pain Findings might be "crushing substernal chest pain relieved by rest or nitroglycerin and exacerbated by exertion." This description implies a Finding with a designated location, a "crushing" Feature with some pattern, and 3 sub-Patterns describing the effect of rest, nitroglycerin, and exercise. The clinical appearance of simulated patients with this Finding might still vary, depending on the allowed variation in sub-patterns. For instance, pain might be more quickly relieved by nitroglycerin than rest or vice versa.

Finally, Patterns include Shape Selectors that help maintain consistency between variables. Shape Selectors are an example of Reasoning Elements, for example, small programs loosely based on the structure of Arden syntax medical logical modules. See, for example, Johansson B G. Wigertz O B, An Object oriented approach to interpret medical knowledge based on the Arden syntax, Proc Annu Symp Comput Appl Med Car, 1992, pages 52-56, incorporated herein by reference.

Reasoning Elements define variables; assign their values from data about the simulation; use loops, "if . . . then" statements, equations, and random numbers to reach conclusions; and finally produce some output. In Findings, the Shape Selector produces one percentile curve to represent the values of a Feature in an individual patient. For instance, although pediatric growth charts allow considerable variation in normal height and weight, one child will exhibit a precise series of values for both height and weight. Height will closely track one percentile curve, as will weight. The percentile of the height curve often limits the possible percentiles of the weight curve: healthy children at 95th percentile height rarely exhibit 5th percentile weight. Most children follow a weight percentile equal to the height percentile _20. The weight Shape Selector can use this equation to restate the familiar height-weight growth chart.

Patterns model time and are one approach to interrelated medical observations. Time affects most numeric values in the model. Consequently, Patterns appear in nearly every entity and relation. Patterns describe the incidence of diseases at different ages, the likelihood of diseases progressing with time, and concentrations of drugs.

Courses of Action (COA) represent people's activities. Not only can these activities be medical, such as taking a blood pressure or performing a coronary artery bypass graft, but they can also include attending school, working, asking and answering questions, and following advice.

Populations invoke Courses of Action to decide when to visit a physician, how to answer questions, and whether to follow advice. Therefore, Courses of Action may advantageously be written to include missed appointments, lying to physicians, and ignoring physician advice. These actions could even depend on aspects of the physician's conduct, such as how the physician chooses to obtain information.

Courses of Action have complex internal structures. A Course of Action organizes Step, which gather, process, and modify information about Populations or Records. For example, a Step might be to obtain a blood pressure from a person. Each Step uses a Reasoning Element to accomplish its tasks. In the case of obtaining a blood pressure, the Reasoning Element would determine and report the simulated patient's systolic and diastolic blood pressure.

A group of Steps that can occur in any sequence is called a Batch. For example, when checking both right and left arm blood pressures, the order in which the arms are checked is probably unimportant, so these can be distinct Steps within a Batch. The Course of Action lists a series of Batches that must be executed in sequence, and describes any mandatory delays between Batches.

For example, to check orthostatic blood pressures, recumbent pressures would be obtained in one Batch. The patient would sit or stand in a second Batch. After a short mandatory delay, sitting or standing pressures would be obtained in a third Batch. Courses of Action also describe possible earnings, costs, pleasure, and discomfort that motivate people to seek or avoid activities.

Agents include physical, chemical, biological, behavioral, and social events capable of influencing health States or Findings. These Agents can be therapeutic, injurious, or both. Agent descriptions include data about intake, metabolism, and excretion, as applicable. For instance, a long-acting steroid is a chemical agent. Following intramuscular injection, the steroid will have predictable local and systemic concentration Patterns as the chemical dissipates from the injection site. The steroid might be metabolized to other compounds and excreted. Exposure to Agents normally occurs during a Course of Action, as this example illustrates.

The model of Agents describes their recognition, their presence, and the presence of metabolites or byproducts. Other parts of the model, such as the sub-Patterns of Findings, describe the effects of Agents.

Table 1 lists relations shown in FIG. 3. The Health States Lead to Health States relation describes how diseases evolve, and is therefore, critical for simulations. Preventive medicine scenarios might use this relation to generate patients who would benefit from screening. Case management problems can use this relation to model both the past and evolving history of a patient.

TABLE 1

Relations Between Entities

Population Contacts Population
Population Related to Population
Population Interacts with Courses of Action
Population Exposed to Agents of Change
Population Has Health States
Population Exhibits Findings
Agents of Change Cause Health States
Health States Lead to Health States
Findings Associated with Health States
Findings Link to Findings
Course of Action use Agents of Change
Courses of Action Identify Agents of Change
Courses of Action Treat Health States
Courses of Action Alter Findings
Courses of Action Reveal Findings
Courses of Action Evaluate Findings Note: These relations link entities in the model together.

Unlike traditional knowledge bases, this relation links Findings (with their Patterns) to a Health State, rather than linking a range of Finding values to a Health State. Sensitivity and specificity are represented as age dependent Patterns, rather than constants. The sensitivity of a Finding will be lower and the specificity higher in this model than in traditional knowledge bases.

The Findings Link to Findings relation describes causal associations between Finding Patterns, such as "severe cough causes abdominal muscle pain." This relation contains data about causality, mechanisms, and temporal constraints. This relation facilitates reasoning about Findings.

The Courses of Action Treat Health States relation illustrates means of curing Health States or preventing their progression. Treatments therefore modify probabilities in a lead to relation.

Courses of Action have three relations with Findings. The first, Alter, implies changing a Feature Pattern by invoking a sub-Pattern. For example, giving acetaminophen could alter a fever. The second relation, Reveal, links examining Courses of Action to the Findings they produce. For instance, a procedure called "taking a blood pressure" reveals systolic blood pressure. The third relation, Evaluate, links a Finding to a Course of Action that might be used to investigate its cause. This relation would link a Finding of systolic hypertension to a Course of Action describing its work-up.

The Population Contacts Population relation traces transmission of communicable Agents and potentially beliefs. Population Is Related to Population describes biological and social relations and the history of those relations, and traces transmission of genetic Agents. These two relations allow descriptions of arbitrarily defined families, with arbitrarily harmonious interactions.

The Population Interacts with Courses of Action relation describes why the Population began the Course of Action, what the Courses of Action cost interested parties, and how comfortable the Population was during the Courses of Action. This model allows a patient to remember an unpleasant experience and resist having it repeated. Because Courses of Action can include negative (buying a therapy) or positive (receiving a paycheck) change in wealth, this relation is also capable of being used to model patients' economic inability to follow medical advice.

The Population Exposed to Agents of Change relation describes perceptions about the exposure, knowledge of exposure, and the course of Action responsible for the exposure. This relation can describe exactly how an Agent was distributed in, metabolized by, and excreted from this Population.

The Population Has Health States relation includes the preceding Health State, a list of Findings attributable to the Health State, and the age at onset, diagnosis, and evolution of the Health State. Health States affect different individuals in different ways, and treatment often depends on the patient's impairments and perceptions. Consequently, a patient's beliefs about disease progression and perceptions of a Health State belong in the Has relation.

The Population Exhibits Findings relation has similar perception attributes. Perceptions can be divided into Dysutility and concern. Dysutility indicates a trade-off a patient would accept to return to normal. Concern indicates a trade-off a patient would accept for full reassurance that a Finding or Health State does not portend future Dysutility. For instance, a patient with a minor left-sided chest pain might rate its current Dysutility as $5 ("I would spend $5 to relieve this pain for today."), and the concern as $100 ("I would spend $100 for assurance that nothing serious caused this pain."). If the pain persists unchanged, both of these values might decline as the patient learns to cope with the discomfort and becomes confident that the symptom has no prognostic importance. Thus, patients can have changing attitudes about stable conditions. Patients would typically seek medical care when provoked to so by a Dysutility or concern.

Records have the same relations as Populations, except that the details are always more ambiguous, inaccurate, or both. For instance, a patient might have influenza starting December 15, while his Record of himself indicates that he developed influenza between December 10 and December 13. The patient's Record of himself is both ambiguous (there are 4 possible days of onset) and incorrect (none of the days is December 15).

We have further determined that the data described in the Lead to, Associated with, and Link to, relations often change with medical interventions or other events. Modifiers describe events that cause a permanent variation in the expected history of these relations. For instance, an event might make evolution to another Health State more or less likely (regular low-dose aspirin reduces the risk of acute myocardial infarction), or could permanently alter the likelihood of exhibiting a finding (cardiac transplant prohibits myocardial ischemic pain). The dashed lines in FIG. 3 show Modifiers. The following examples illustrate some modifiers (for example, Bayesian network from a Lead to relation, Bayesian network describing risk factors for progression, and the like).

Population Interacts with Courses of Action modifies Health States Lead to Health States. An appendectomy alters the progression of acute appendicitis to appendiceal rupture. For example, life-span-altering interventions always modify a Lead to relation.

Population Exhibits Findings can modify Health States Lead to Health States. For example, being overweight increases chances of developing a deep vein thrombosis or pulmonary embolism.

Population Has Health States can modify Health States Lead to Health States. Diabetes accelerates the onset of cardiovascular disease.

Population Has Health States can modify Findings Associated with Health States. Diabetic neuropathies diminish pain associated with myocardial infarction or extremity injuries.

Modifications of these relations account for many benefits ascribed to receiving medical care. Other benefits can occur when medical interventions temporarily decrease the severity o Findings.

The model described herein is intended to be a highly structured and realistic representation of family medicine that will guide the design of the family practice knowledge base and support the generation and evaluation of recertification examinations. In this model, the following are strong assumptions: (1) Health States are discrete and distinguishable on the basis of associated Findings, which are also discrete and distinguishable on the basis of the Patterns of their Features. (2) After choosing a percentile curve in a Pattern to represent some value, the percentile does not change substantially. (3) Changes in Patterns (e.g., the probability of one Health State evolving to another) can be described for important combinations of risk factors, interventions, and time of occurrence. (4) Transitions from one Pattern to another can be estimated by simple means. (5) Modifying relations do not have important interactions with one another. (6) Highly developed anatomic and physiologic models are not necessary, because associations between Findings provide the same information.

Although the model should have clear places to store nearly all interesting facts about family practice, test generation does not require a comprehensive description of all facts used in family practice. The proposed test generates plausible problems from a set of data intentionally skewed to generate interesting (i.e., discriminating) cases. The present invention provides the flexibility to avoid controversial questions by controlling skewed data. For instance, if the management of borderline diabetes is controversial, the present invention allows editing of the family practice knowledge base so that diabetics' fasting blood glucose levels are always markedly elevated. The family practice knowledge base would then be incapable of creating a borderline diabetic.

The diagram of the model illustrated in FIG. 3 reflects many family medicine concepts, and therefore, helps students, physicians and others understand the process at work in family medicine. For instance, the diagram illustrates that Populations have biological and social relations. Populations exist in Health States, which evolve into new, sometimes undesired Health States.

A major goal of family medicine is to retard or stop undesirable evolutions and promote desirable evolutions. Stopping one undesirable evolution could, however, result in a different undesirable evolution. In addition, physicians who treat symptoms will Alter Findings, but do not necessarily Treat Health States. Altering Findings usually changes current quality of life, whereas treating Health States usually changes future quality and quantity of life. Because Findings occur in the context of Health States, we have determined that physicians contemplate what Health States might be responsible for Findings, rather than Alter the Finding without considering future quality of life. The only tools available for these causes are Courses of Action. Physicians prescribe Courses of Action, but only patients Interact with Courses of Action. For example, the prescription does not guarantee that the patient follows the correct Course of Action. Agents (e.g., drugs) make a difference only when used in the context of a Course of Action.

The model's details provide further insights for students. First, time is an extremely important element of primary care. Patterns become more distinctive as time passes, simplifying diagnosis. The total risk of going from one Health State to another increases with time, increasing the value of early interventions. Second, patients have variable and evolving attitudes about Health States, Findings, and Courses of Action. The goal of medicine might not be to adhere to an endorsed Course of Action, but to optimize each patient's perception of his or her quality of life. To reach this goal, physicians adjust Courses of Action to accommodate individuals' attitudes. Third, the importance of time and attitude in optimizing the quality of a patient's lifetime suggests that continuity of care might help some patients.

The scope of family practice and the importance of protocols, time, individual variations and attitudes, and rationales distinguishes the content of the family practice knowledge base. That is, advantageously, some differential diagnosis of internally generated cases is possible using the model.

In this model, differential diagnosis largely depends on establishing the presence of Findings, which in turn depends on establishing the presence of Patterns and sub-Patterns of Features. Except in rare cases of pathognomonic values, confidence in the presence of a Pattern will increase with the passage of time.

We have also determined that the structure of an interface to medical reference systems might be enhanced using the model. Current reference systems use the structure of medical publications and lists of abstracted subject headings to facilitate searches through very large databases. These searches can yield large numbers of extraneous citations, especially for novice users.

The model suggests an alternative indexing strategy, as well as a graphical search interface. For instance, one could view a query interface similar to FIG. 3. To request a query about the effect of insulin treatment on the development of retinopathy in diabetic patients, one selects diabetes from an unrestricted list of Health States. The Lead to allows the user to select diabetic retinopathy from a list of diseases restricted to diabetic sequelae. The Modifier specifies which Course of Action or Agent of Change to consider. The computer delivers a list of references mentioning insulin in a diabetes Leads to diabetic retinopathy relation. Searching for a particular relation between two entities improves the efficiency of searches usually performed by naming the entities.

Overview of Patient Generation/Evolution Processes

Figure 4:
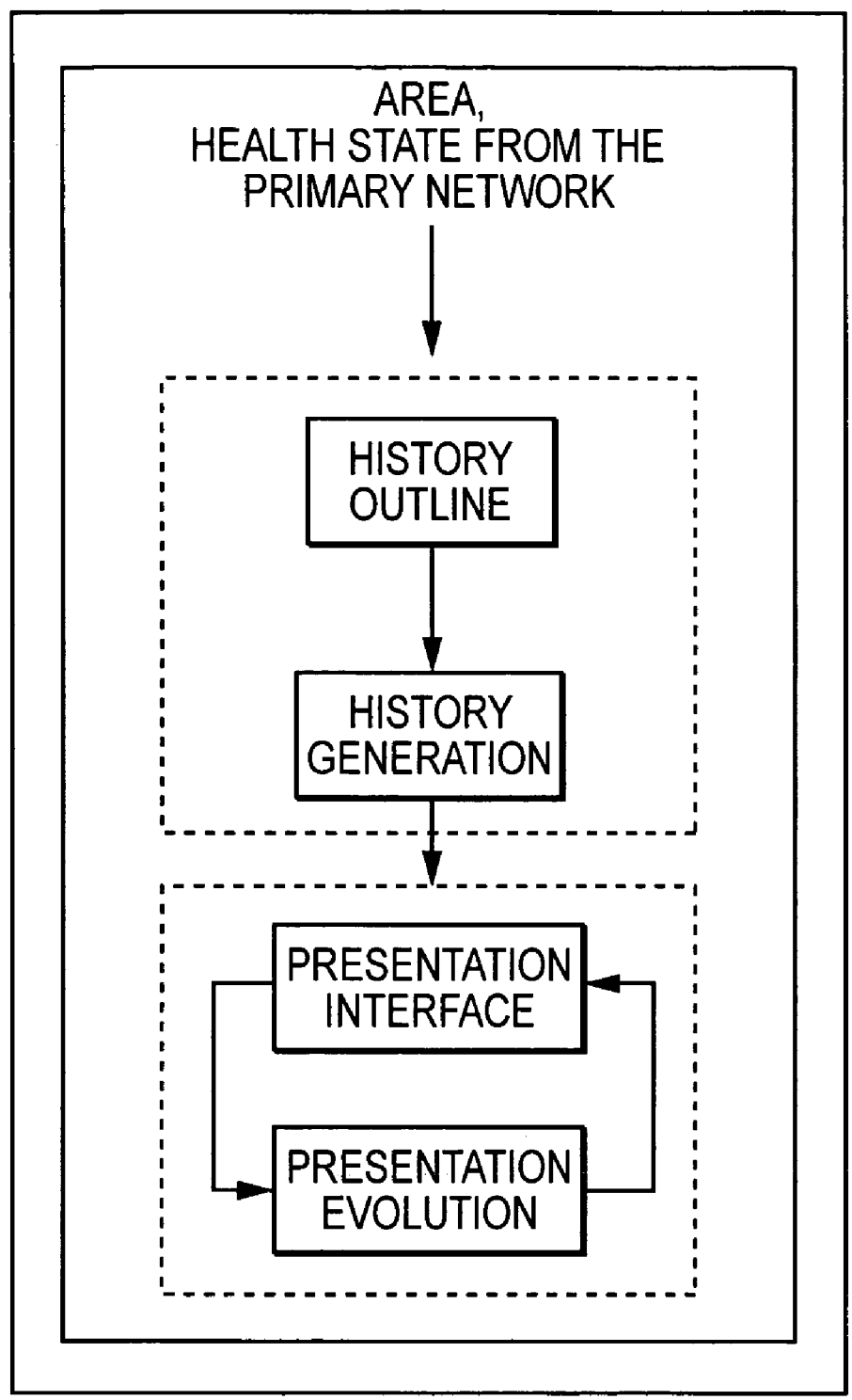
FIG. 4 is a flowchart of the overall process for the computer based examination system of the present invention.

We describe here an overview of processes used in the certification/recertification system. The processes are divided into four main groups:

1. Patient generation processes:
   history outline processes
   history generation processes 2. Simulation processes
    Presentation interface processes
    Patient evolution processes
    Patient generation processes are called once and produce the subject for the examination session. Simulation processes may be called repeatedly several times. The patient generation process presents the patient to the examinee, collect the examinee's responses and queries, and evolve the patient. See FIG. 4 for a pictorial overview of the system.

For the patient generation process, we assume that the area for the simulation—a specific object, say A, from the class AREA—and a health state, say H, from the primary network of the area A are given. For example, A may be the area of the adult onset diabetes and H may be the health state of symptomatic diabetes.

The patient generation process consists of two phases:
    1. history outline, and
    2. history generation.

The goal of the history outline phase is to generate a progression of health states and risk factors traversed by the patient on the way from the normal condition to the specified health state H. It starts with a call to the procedure that establishes sex and race of the patient being generated (referred to as procedure GenderRace). The next step establishes the age of onset of H (call to procedure OnsetAge).

The goal of the next step is to select the precursor state for the target state in the simulation as well as risk factors (circumstances) that will affect the patient under construction. This will be accomplished by a call to the procedure OutlineFirstStep.

Figure 5:
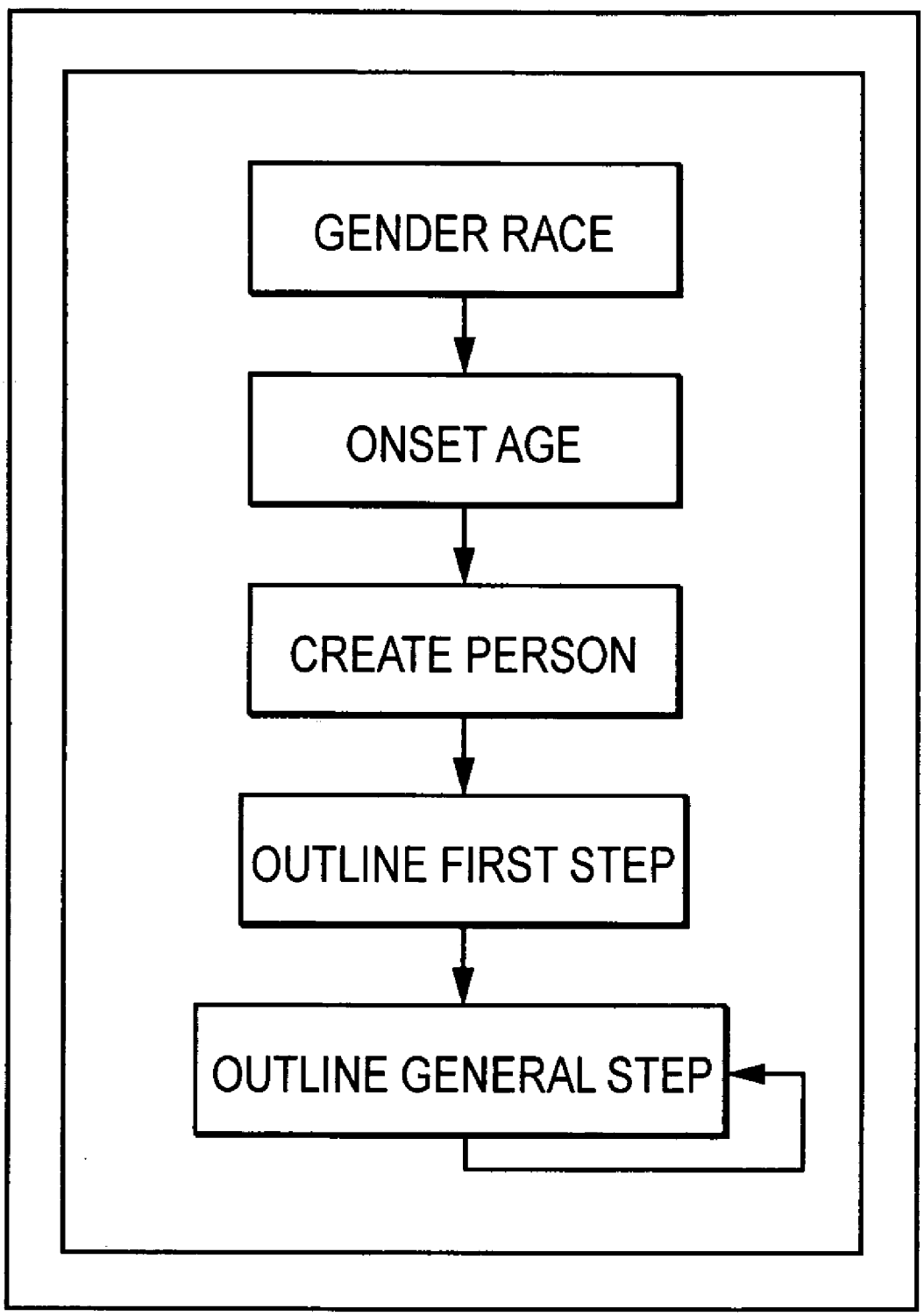
FIG. 5 is a flowchart of the history outline process which generates the patient history in the computer based examination system of the present invention.

The next procedure, OutlineGeneralStep, is called iteratively until the normal health state is reached. In each iteration, it finds the precursor health state as well as its onset time. When the normal health state is reached, the history outline phase is complete. See FIG. 5 for a flowchart of this process.

The GenderRace procedure generates sex and race of the patient under construction.

CreatePerson creates a basic description of the person. We select last, first and middle names, and age of the person, as well as two basic demographic findings: sex and race. These last data are stored as EXHIBITS tuples (since demographic findings are treated as findings).

The OutlineFirstStep procedure generates the precursor state for the target health state for the simulation, and its onset age. In addition, it selects circumstances to which the simulated patient has been subject. This procedure also creates an object HS_path, stored on the white board and containing the sequence of HAS instances for the precursors of TS, starting with the normal health state and ending with TS. This sequence will be used later in the history generation phase.

The Generating history outline, and more specifically, the OutlineGeneralStep procedure, generates the complete path of precursors of the target health state. It starts in the normal health state and terminates in the target health state TS (of course, the last but one state on the path has already been generated by OutlineFirstStep procedure).

History Generation

Figure 6:
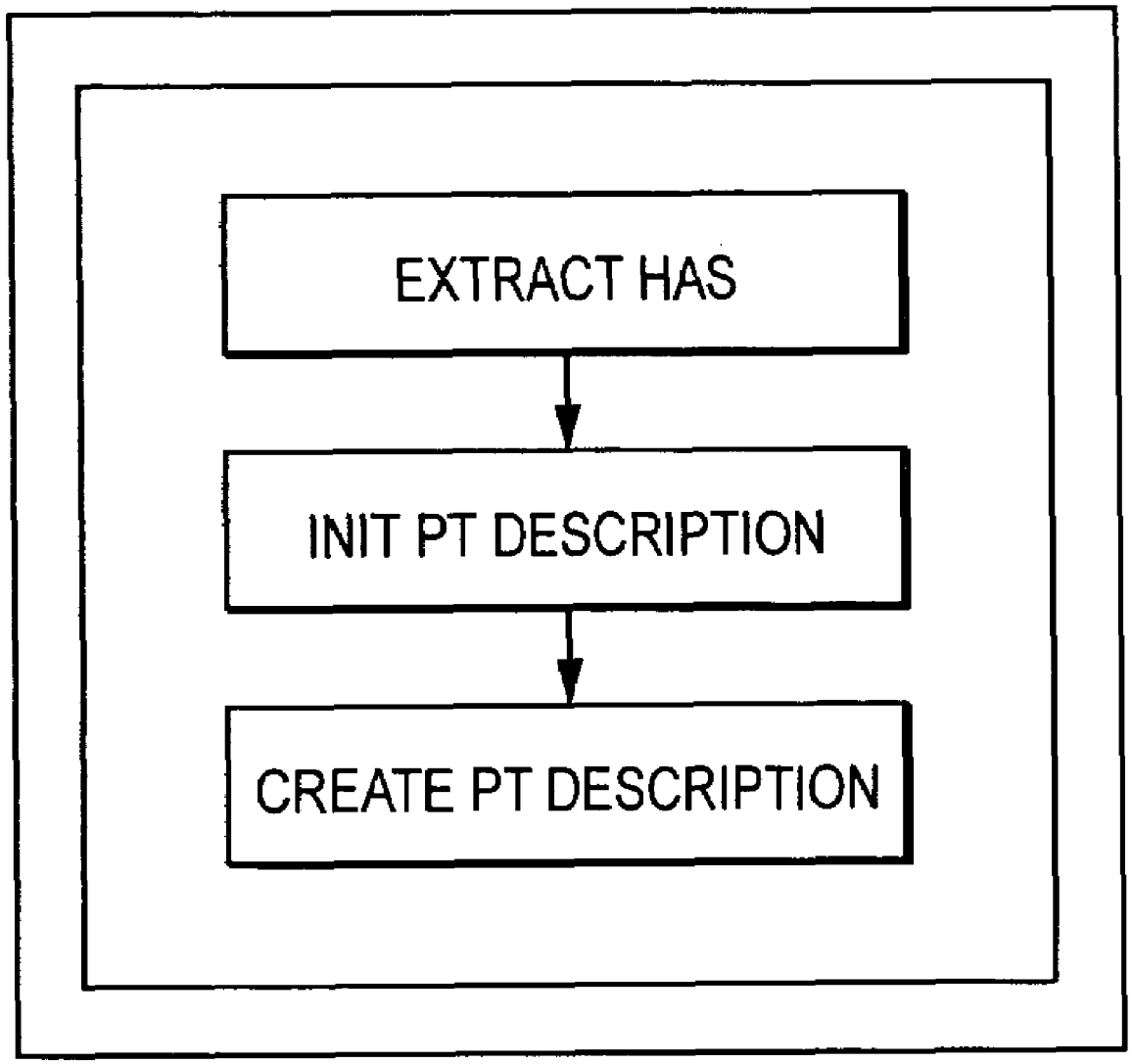
FIG. 6 is a flowchart of the history generation process which finds values for the patient history in the computer based examination system of the present invention.

The history generation phase finds values that are established in each case when they differ from normal (normal values are derived from the defaults maintained in the knowledge base). The general outline of this phase is given in FIG. 6.

The reasoning element, called generation method, describing how a given health state or a risk factor determines a finding, plays an important role in this phase. The generation method either provides a description of all relevant basic features at all relevant sites (for normal states), or determines which basic features at what sites need to be adjusted and by what specific findings. The main input for this phase is the list of associated objects attached to the object P of type PERSON (the object of the simulation).

The history generation process looks at all associated objects and modifies values of patterns describing relevant basic features so that the detailed description of the patient is consistent with the health state history as created in the earlier phase. Therefore, in this phase we focus on describing findings and their basic features. To this end, we look at all health states represented by HAS instances. We sort them according to their onset times. This results in a list in which all states normal in their areas precede all the abnormal states. The reason for this is that all normal states start at time 0. For each of these normal states we will run its generation method. This creates a list of finding names and site names to which the findings pertain, and defines the domain of all findings for which specific descriptions are created.

Next, for every finding, the patterns of its basic features are instantiated. We obtain these patterns from "normal" specific finding belonging to the finding in question. To select specific curves, we use a percentile value. This value will generally be selected from, for example, the range [0.15, 0.85] uniformly at random. Each time we need to use this value to select a specific pattern, we modify it, for example, by a randomly selected number from the range [−0.05,0.05]. In this fashion the modified value is, for example, in the range [0.10,0.90].

After all normal states are processed, patterns of all basic features of all relevant findings are instantiated for life. From now on, when processing other health states these patterns are modified. The idea is to run the generation method for a health state. As a result we get a list of sites and basic features which must be modified as well as specific findings where the new patterns can be found. If only some sites for the finding are generated, only those sites need to be modified. To modify the patterns, we use patterns captured by the appropriate specific finding. Again the basic percentile is varied and used in the selection. The selected pattern is then superimposed on the existing pattern (its values replace the old values starting with the onset age for the health state).

The generation method associated with the health state H, generates the list of relevant findings with additional information on sites and specific findings. That is, for each finding we maintain the list of sites and with each of those we associate the list of all basic features (names) corresponding to the finding. Finally, these basic features are described by their patterns.

The PatientDescription procedure selects HAS instances. It then arranges them according to onset times, generally earliest first. In this process, the procedure invokes the generation method procedures for each health state, thus creating EXHIBITS tuples describing findings associated with health states.

The InitPt Description (Initialize Patient Description) procedure initializes the list PATIENT FINDINGS, which contains all findings relevant to the primary health state as well as all secondary (modifying) health states. It creates all corresponding EXHIBITS instances and attaches them to the list associated_objects. All these findings are initialized to their normal values.

After the call to InitPtDescription, the domain of findings, sites and basic features, which subsequently will be modified, is defined. CreatePtDescription scans the list of HAS instances and adjusts findings so that the resulting patterns are consistent with the history of health states.

Patient Evolution

As explained earlier, we assume that data required by the processes is stored in the entity relationship model, white board (WB) and in the area of memory local to patient generation and evolution processes. This local memory will be denoted as LM. We start the evolution phase with the patient fully described and stored in the WB. An equivalent description exists in LM. Several HAS instances describe continuing health states (one of them -primary). After the assessment phase (requiring physical examination and history taking) the examinee proposes treatment consisting of one or more courses of action. These courses of action may alter some of the health states the patient is currently in. All selections made by the examinee are gathered in a table coa_list.

LEAD_TO data describes probabilistic information on progress from one health state to another. This data depends on modifiers. At present, we use a small generic set of modifiers: "fast progress," "moderate progress" and "slow progress." For each of these modifiers, and for an edge in the health state network between a precursor health state PS, and the target health state TS, the entity relationship model contains an estimate of the flow along that edge.

Courses of action are represented in WB by a table which describes their structure in terms of elementary courses of action. We will describe this structure below. In addition, each course of action contains a reasoning element. This reasoning element, given an edge (a pair (PS,TS)) and a set of other current health states (as modifying events), computes one of these three modifiers. Flows on the edges starting in the current health state are used in the selection process. Once the selection is made, duration risk stored in the appropriate LEAD_TO tuple is used to determine the onset time for the selected health state.

The following structure is used to represent a course of action COA in WB. The data is stored in a table with, for example, four columns (additional columns may be necessary later for evaluation purposes). The first column is labeled ECOA (elementary course of action). It lists all concrete elementary courses of action that might be used in a construction of COA. The second column describes the type of the corresponding elementary course of action. ECOAs of the same type are identified by the same integer in the second column. The third column contains one of five boolean operators: none (NOR), single (XOR), at least one (OR), some but not all (NAND), all (AND). All members of a type are assigned the same operator in column 3. The fourth column contains weights which are used in the matching process.

One of the courses of action listed with every health state is called TIME. It describes the effects of no specific action by the examinee and serves as a default course of action.

The evolution phase is accomplished by the procedure called Evolve. Evolve has three input parameters: patient P, patient's age T, and the list coa_list of COAs selected by the examinee. Evolve starts by creating the list of patient P continuing health states. This is accomplished by the procedure called SelectPresentHas. SelectPresentHas selects from the list of P associated objects those HAS instances that represent continuing health states. It arranges selected HAS instances in a list.

For each health state PS described by the list of selected HAS instances, we then identify in all the courses of action that are relevant to PS. It gathers all those courses of action that are in relation MANAGE with the health state PS, in the list called, for example, coas.

At this time, the closest COA, among those found relevant to PS, to the examinee selection (described, recall, by the list coa_list) is chosen. For the course of action, say COA, target states are created for PS, corresponding modifiers and flows. This data is used for evolution.

These steps are repeated for each health state PS. When the process is completed, all successor health states are represented by means of the corresponding HAS instances. The evolution step is completed with a call to CreateDescription procedure. It generates descriptions of specific findings corresponding to the health states.

Stochastic Process for Patient History Generation

The present invention provides a method to automate authoring of major events in simulated medical histories. We have designed a knowledge base with temporal descriptions of the incidence and prevalence of health conditions and plausible intervals between health conditions. Each health condition is part of a small sequence of related and mutually exclusive health conditions. Many of these small networks exist in parallel.

We have determined that a patient's overall health can be described by a vector indicating the patient's current health condition in each network. A patient's location in one network often affects timing of transitions in other networks. The knowledge base advantageously uses modifiers (for example, Bayesian network from a Lead to relation, Bayesian network describing risk factors for progression, and the like) to describe the influence of these and other risk factors, as well as interventions, on incidence and transition times. A stochastic history outlining algorithm uses these data to construct a lifetime and recent medical history whereby a patient might develop a specified vector of health conditions.

The present invention generates a large number of plausible history outlines. The present invention automates the authoring of major events in the lives of simulated patients. The present invention applies a Monte Carlo process to multiple stochastic trees, to generate large numbers of plausible case outlines. Further automated embellishment of these outlines yields complete, usable simulated case histories.

Previous efforts to simulate patients from data have used sensitivity information stored in a diagnostic database, or Quick Medical Reference®, to stochastically create a description of findings in a patient with a disease. See, for example, Bergeron B. Iliad: A Diagnostic Consultant and Patient Simulator, MD Computing 1991, Vol. 8, pages 46-53; Miller R A, Masarie F E, Myers J D, "Quick Medical Reference (QMR)" for diagnostic assurance, MD Computing 1986, Vol. 5, pages 34-49, incorporated herein by reference. However, we have determined that these simulations lack rich historical details and may generate implausible combinations of events. See, for example, Sumner W., A review of Iliad and QMR for primary care providers, Archives of Family Medicine 1993, Vol. 2, pages 87-95, incorporated herein by reference.

Some simulations generate patient details from a complete and precise mathematical model of pathophysiology. See, for example, Valdivia T D, Hotchkiss J, Crooke P, Marini J., Simulating the clinical care of patients: A comprehensive mathematical model of human pathophysiology, Proc 19th Annu Symp Comput Appl Med Care. 1995, page 1015, incorporated herein by reference. This elegant approach is feasible in intensive medical care and some restricted organ systems, but primary care problems are not so well understood at present, and therefore require empirical description.

Accordingly, we have also developed a process for generating detailed patient histories culminating in a specified set of simulated health problems. The first segment of the algorithm creates an outline of the medically important events in a patient's life, including the patient's age at the onset and termination of different health conditions or exposures to biologically active agents. The second segment of the algorithm yields a detailed description of continuously defined facts about the patient, such as physical and chemical characteristics, morphology, function, and sensations throughout life.

The history outlining algorithm essentially creates paths through temporally reversed Monte-Carlo processes, casting major events in a patient's history while guaranteeing that the history ends with specified medical conditions. See generally, Rubinstein R Y, Simulation and the Monte Carlo Method, New York, N.Y., John Wiley and Sons Inc.; 1981, incorporated herein by reference. This process is applied to a set of stochastic disease history models, each describing the evolution of one health problem.

A knowledge base stores these models, along with standard modifiers that calculate temporal constraints on disease progression, conditioned on comorbidities and treatments. This algorithm is capable of generating many plausible cases in a short period of time preceding an examination.

The "Health condition Leads To Health condition" cycle is the central component in the generation of a patient history. A health condition is a named collection of facts, which usually have prognostic implications. Typically, the facts that connote a health condition have a specified degree of variation from normal ranges, and are thought to arise from a common underlying cause. A health condition can usually be considered to be located at one or more body structures where that underlying cause is present.

Health conditions uses patterns and subpatterns to predict their prevalence and incidence, conditioned on factors such as sex and race. Prevalence and incidence are provided in a widely used structure called shape, which plots a value over time. In this situation, time indicates the simulated patient's age.

A health condition uses a generation method reasoning element to establish the facts pertaining to its instantiation. These facts may include events like drinking alcohol or driving cars, but most facts are specific instantiations of more generic medical concepts, such as symptoms or laboratory values, in specified body parts. For instance, the generic concept of "synovial fluid glucose level" might be instantiated as "normal" in "both knees." Shapes describe exactly how a value in this instantiation may reasonably evolve or fluctuate over time.

Two special classes of health conditions exist. First, normal health conditions are incident only at birth (or conception, depending on testing goals). Second, "Alive" is a health condition whose prevalence shows the proportion of a cohort that survives to any age. The age specific prevalence and incidence of all other health conditions are defined as the percentage of living individuals at that age who experience or acquire the condition, respectively.

The leads to relation connects one health condition (the precursor) to another (the target), and describes possible time intervals required for evolution from the precursor to the target. A Pattern describes a probability density function (pdf) of these time intervals, conditioned on comorbidities, treatments, and other risk factors. This duration pdf provides a time constraint mechanism. For instance, a duration pdf for the progression of mild to moderate knee osteoarthritis, given obesity, might indicate a probability density of zero in the first five years following the onset of mild osteoarthritis, a uniform probability density from year five to year twenty, and then a probability of zero. This implies that all simulated obese patients develop moderate osteoarthritis between five and twenty years after the onset of mild osteoarthritis, and forbids simulated onsets at other times.

The modifiers of a Lead to relation also provide time constraints for risk factors. This allows the model to represent the concept that obesity must exist for a period of at least 10 and up to 40 years for this duration pdf to apply.

Finally, the Lead to relation provides information about how quickly and completely to convert from the findings typical of the precursor to findings typical of the target. For instance, if each knee osteoarthritis stage is a health condition, and each stage has a typical degree of joint space narrowing, then the transition from one stage to another should be accompanied by more narrowing of the joint space. The Lead to relation can indicate that this narrowing occurs over years, and that the narrowing is nearly complete when the simulation asserts that the latter osteoarthritis stage is present.

A series of Lead to relations connect health conditions into small networks illustrating evolutionary sequences of events. These networks often suggest a disease staging scheme, such as (Stage 0) No Knee Osteoarthritis, (Stage 1) Mild Knee Osteoarthritis, (Stage 2) Moderate Knee Osteoarthritis, and (Stage 3) Severe Knee Osteoarthritis.

We call this sequence a parallel health condition network. It is "parallel" to many other networks of health conditions that exist simultaneously in a person. In general, a parallel health condition network lists transitions that occur among an exhaustive set of mutually exclusive health conditions occurring in one body part. For instance, the left knee of a patient exists in one of the health conditions in the osteoarthritis network. The right knee also exists in one of these conditions, but not necessarily the same condition found in the left knee. The patient simultaneously exists with one condition in a gastric ulcer network, a weight network, and numerous other networks.

A simulated patient's overall medical condition is therefore a vector, V, listing the current health condition from each parallel network at each involved site. A case specifies vector $V_0$, indicating the health conditions instantiated at the initial presentation of a simulated patient, and sufficient information to create a history of vectors culminating in $V_0$.

Most of the parallel networks in any given case are inactive. These define an initial, usually normal, (stage 0) condition of the parallel network. Most cases contain a few active parallel networks. Active networks presenting at stage 1 or higher represent active medical problems. Active networks presenting at stage 0 represent potential problems, such as complications resulting from an active problem or its treatment. The examinee's task is generally to identify and respond to active networks in advanced stages, while minimizing disease progression in active networks at stage 0.

Active networks can be divided into two categories. A case usually focuses on care for a primary network "P" (for instance, osteoarthritis of the knees). A comorbid network "C" usually includes health conditions that influence, or are influenced by, the stage of evolution of a primary network. For instance, obesity is a risk factor for osteoarthritis, and osteoarthritis may worsen obesity by limiting exercise. Comorbid networks that do not interact with the primary network in any important manner may serve as distractors.

For instance, an episode of urethritis might be irrelevant to osteoarthritis, but suggests Reiter's syndrome as an alternative explanation for knee pain with an effusion. An active, stage 0 comorbid network provides opportunities for complications. For instance, a simulated osteoarthritis patient presenting with a "No gastric ulcer" health condition could advance to "Gastric ulcer" after receiving steroidal nonsteroidal anti-inflammatory drugs.

When an active parallel network describes a chronic condition, acute exacerbations may be expected with some of the health conditions in the network. An exacerbation network "E" is a parallel network describing acute flares of illness that occur during a more chronic health condition. For instance, flares of knee pain with effusions may occur in patients with chronic osteoarthritis. In principle, health conditions within an exacerbation network can have their own exacerbations. The simulation process of the present invention allows exacerbation networks to contain cycles, unlike primary and comorbid networks.

A simulated patient's medical history is the sum of the events culminating in the case defining vector, $V_0$. The case provides sufficient information to create many plausible histories, but does not store histories per se. Consider a case defined to culminate in severe bilateral knee osteoarthritis and morbid obesity. The relative sequence of events on the primary and comorbid networks are not necessarily constrained. Obesity might be required to occur before the onset of mild osteoarthritis. However, the onset of morbid obesity could occur before or after the onset of moderate osteoarthritis.

The Cartesian product of two active, linear parallel health condition networks, P and C, yields a two dimensional web of health condition combinations. This product re-establishes the complexity avoided by the parallel network simplification, and calls attention to interactions between P and C. A vertex in this web is composed of the ith health condition in P and the jth health condition in C, and is represented by the vector $V_0=(P_i,C_j)$. Evolution can be assumed to occur in only one dimension at a time. If evolution in both networks can occur simultaneously in life, one can be assumed to occur first, and the other a moment later for purposes of the model. That is, the set of vectors $V_{-1}=\{(P_{i-1}, C_j)\}; (P_i, C_{j-1})\}$ are immediate precursors of vector $V_0$, but $(P_{i-1}, C_{j-1})$ is not. Similarly, the set of vectors $V_{-2}$ includes $(P_{i-2}, C_j)$, $(P_{i-1}, C_{j-1})$ and $(P_i, C_{j-2})$.

Three kinds of interaction are possible in the web formed by networks P and C. First, the networks may be completely independent, so that evolution along one dimension has no implications for evolution in the other. Second, progression through one network may depend on the concurrent condition of an independent network. For instance, the incidence of early osteoarthritis conditions is dependent on the presence of obesity. Finally, mutually dependent networks create a web in which progression through each network depends on the concurrent condition of the other network. For instance, a realistic simulation of a severe osteoarthritis history might require modeling a "vicious cycle" where obesity accelerates osteoarthritis, which in turn accelerates obesity.

The Cartesian product of N parallel health condition networks similarly yields an n-dimensional web of health condition combinations, with potentially complex interactions. Data acquisition for these webs is a daunting task, but might be simplified by (1) limiting the number of dimensions, (2) ignoring improbable health condition combinations, particularly when describing vicious cycles, and (3) assuming independence for some kinds of test cases even when dependence exists in reality.

Stochastic Process History Outlining Process

The goal is to produce patient care scenarios for recertifying diplomates to manage. The data described above allow automatic generation of such cases, starting from a case specification. The case is composed of primary network P, and comorbid health condition network C. Network P is composed of health conditions $P_0, \ldots P_n$ and "lead to" relations $PL_{0\to 1}, \ldots PL_{n-1 \to n}$. Network C is composed of health conditions $C_0, \ldots C_m$ and "lead to" relations $CL_{0\to 1}, \ldots CL_{m-1 \to m}$.

Chronic health condition $P_j$ in network P has acute flares described by parallel network E. Network E is composed of conditions $E_0, \ldots E_q$ and "lead to" relations $EL_{0\to 1}$, $EL_{1\to 0}, \ldots EL_{q-1\to q}, EL_{q\to q-1}$. The normal condition of network E is $E_0$, and the network may cycle through $E_0$ up to X times.

The vector $V_o=(P_i, C_j, E_k)$ summarizes the health conditions required at the presentation of the case. Health conditions $P_i$ and $E_k$ may be incident or prevalent at presentation. Incident health conditions would typically require both diagnosis and management, while prevalent health conditions would often be known diagnoses, and require only management decision. Health condition $C_j$ is usually prevalent.

The first step assigns the sex, race, and other genetically determined facts to the prospective patient. If $P_i$ is an incident health condition in the simulation, the incidence pattern for health condition $P_i$, is conditioned on sex and race. Sex and race are assigned by obtaining the area under the incidence curves for male and female patients of each race. The simulator makes a weighted random selection of the patient's sex on the basis of the results.

In the weighted random selection process, a series of positive values is normalized to one by dividing each value in the series by the sum of the series. The resulting series defines a probability distribution. To select an item according to this probability distribution, the interval from zero to one is divided into consecutive subintervals of lengths equal to the corresponding probability the series. A random number from zero to one is generated from the uniform distribution. The interval to which it belongs defines the selected item.

Because the incidence or prevalence of some illnesses, such as knee osteoarthritis, can increase dramatically with age, some correction to approximate the absolute number of cases occurring at each age may be useful, depending on the goals of the simulation. To obtain absolute numbers of incident or prevalent cases at each age in a cohort, the incidence or prevalence at each age is multiplied by the fraction of the cohort in that age interval. Formula 1 illustrates this calculation, and the general procedure for multiplying two shapes.

Formula 1. Absolute Prevalence of Health Conditions as a Function of Age:

$$\text{Absolute prevalence}(P_i,n)=\text{prevalence}(P_i, n) * \text{prevalence}(\text{Alive}, n)$$

Where prevalence (health condition, n)=the prevalence of health condition at age n years.

Similarly, the joint absolute prevalence of $P_i$ and $C_j$ can be calculated by multiplying the absolute prevalence of $P_i$ by the prevalence of $C_j$ in each age interval. Although the prevalence of either or both health conditions may be explicitly conditioned on the presence of the other, knowledge acquisition efforts are unlikely to capture such dependencies. Calculating the joint prevalence reduces the chance of creating an unsolvable history, for instance by creating a prevalent case of $P_i$ at an age where $C_j$ does not exist, regardless of the prevalence produced in knowledge acquisition. A weighted random selection of an age of presentation can be made from the product of the age specific prevalence of all representing health conditions, and the special condition "Alive."

Often, either $P_i$ or $E_k$ is an incident health condition, and the age of onset of the presenting health condition vector, $V_0 = (P_i, C_j, E_k)$, is determined by the preceding step. In addition, the immediately preceding health condition vector, $V_{-1}$, must be $(P_{i-1}, C_j, E_k)$ if $P_i$ is incident, because any other vector would make $P_i$ prevalent rather than incident at age N. More commonly, $E_k$ is incident and vector $V_{-1}$ must be $(P_i, C_j, E_{k-1})$. Alternatively, if $V_0$ consist only of $P_i$ prevalent health conditions, then the age of onset of $V_0$ is unknown. In general, health condition vectors contain a mixture of conditions with known ending times (e.g., precursors of incident conditions in $V_0$) and unknown ending times (e.g., prevalent conditions in $V_0$).

Assume that $P_i$ is an incident health condition at age N. The interesting vector is therefore $V_{-1} = (P_{i-1}, C_j, E_k)$, because health condition $P_{i-1}$ evolved to $P_i$ at age N. One possible precursor of vector $V_{-1}$ is $(P_{i-2}, C_j, E_k)$ which would evolve to vector $V_{-1}$ at the age of onset of health condition $P_{i-1}$.

The age of onset of $P_{i-1}$ is constrained in part by the age specific incidence of $P_{i-1}$, and N. The incidence of health condition $P_{i-1}$, conditioned on race and sex yields the number of new cases per year per number of persons at risk, in each year from birth to age N. Because the simulated patient must belong to a cohort of individuals who lived until age N, corrections to obtain an absolute incidence are usually not important.

The age of onset of health condition $P_{i-1}$ is further constrained by the plausible duration of $P_{i-1}$. For instance, if $P_{i-1}$ always progresses to $P_i$ within ten years, then a case of $P_{i-1}$ must have begun between ages (N−10) and N. The "lead to" relation $PL_{i-1>i}$ provides a duration pdf, conditioned on pertinent facts representing some known modifier. The duration pdf is a probability distribution function defining probabilities of evolution to $P_i$ time intervals subsequent to the development of $P_{i-1}$. The duration pdf is truncated at the time equivalent to the age of presentation, N (assuming that $P_i$ could not have begun before birth), and reversed in time. The reversed duration pdf indicates at age 0 the probability that a transition from $P_{i-1}$ to $P_i$ would take N years, the simulated patient's entire life. In the year before presentation, at age N−1, the reversed duration pdf shows the probability that the transition would occur after exactly one year.

For each year from birth to the age of onset of $P_i$, the incidence of health condition $P_{i-1}$ and the reversed duration pdf are multiplied to obtain a weighting factor for the onset of $P_{i-1}$ in that year. These weights are used to make a random weighted selection of one year to propose as the age of onset for the health condition $P_{i-1}$. This age represents one proposal for the age of onset of $V_{-1} = (P_i, C_j, E_k)$.

Formula 2. Weight ($W_n$) for establishing the onset of health condition $P_{i-1}$ at age n:

$$W_n = \text{Incidence}(P_{i-1}, n) * \text{DurationPDF}(P_{i-1}, N-n)$$

Where:
N=age of onset of health condition $P_i$
DurationPDF (health condition, x)=probability that health condition evolves to its successor during the time interval x−1 to x years after its onset.

In general, this procedure is repeated for each health condition with an onset time after birth (or conception) in the currently interesting vector, $V_{-1}$. The result is a proposed list of ages of onset for a subset of vectors in the set $V_{-2}$. The next step proposes ages of onset for the remaining vector in $V_{-2}$.

Assume that health condition $C_j$ is a prevalent condition in a simulated patient presenting at age N. Assume that the annual incidence of $C_j$ is constant from age N−3 to N, and that $C_j$ is equally likely to evolve to $C_{j+1}$ in 1, 2, or 3 years. The duration pdf from the "lead to" relation $CL_{j->j+1}$ is therefore uniform over years 0 to 3. Consequently, $C_j$ beginning at age N−3 is as likely to continue to age N−2 as to age N−1, but will not be prevalent at age N in either case. Conversely, most cases of $C_j$ beginning at age N−1 would be prevalent at age N. To accommodate the uncertainty regarding the onset time of $C_{j+1}$, the duration pdf is reversed in time (as in the previous step), then converted to a cumulative probability function. The highest cumulative probability occurs just before the age of presentation.

Formula 3. Reversed cumulative probability (RCP) of duration of health condition $C_j$:

$$RCP(n) = \Sigma(DurationPDF(CL_{j->j+1}, N-y))$$

$$y = 0 \text{ to } n$$

Where:
N=age at presentation
y=a number of years between 0 and n.

For each year from birth to the age of presentation, the incidence and reversed cumulative probability of duration are multiplied to obtain a weighting factor for the onset of $C_j$ in that year, a random weighted selection chooses the year to propose as the age of onset for the health condition $C_j$. This age represents a second proposal for the age of onset of $(P_i 1, C_j, E_k)$.

Formula 4. Weight ($W_n$ for selecting age n for the onset of health condition $C_j$:

$$W_n = \text{Incidence}(C_j, n) * RCP(n)$$

At this point, the simulator has completed these steps. It found vector $V_0$ to have a single possible predecessor, $V_{-1}$. Each health condition listed in $V_{-1}$ could have been the last to develop, therefore the simulator proposed a plausible age of onset for each. The simulator used one of two algorithms to calculate age of onset of each condition, depending on whether or not it could identify the age at which the condition ended.

Each proposed age corresponds to a change in one element in vector $V_{-1}$. The collection of vectors produced by these single health condition changes is the set $V_{-2}$. Consequently, selecting the health condition to change specifies which member of the set $V_{-2}$ is part o the history of this simulation. Although only one vector in $V_{-2}$ will appear in the history of this simulation, all of the health conditions in $V_{-1}$ will be traced back to birth through vectors from sets $V_{-3}$, $V_{-4}$, etc. The question is not whether each condition has a history, but when events occurred.

A safe strategy is to instantiate the vector from $V_{-2}$ occurring at the latest age, along with any facts that had been tentatively proposed with that age and vector. If two or more vectors from $V_{-2}$ share the latest moment in age, one may be selected at random. The history generation step is repeated with the instantiated vector from $V_{-2}$ replacing $V_{-1}$ as the focus of attention.

The "lead to" relations, such as $PL_{j-1 \to i}$, may need to instantiate modifiers in order to produce a duration pdf.

Some modifiers might be defined by a history of a health condition in an active network. Instantiations of health conditions in active networks create additional temporal constraints for these conditions. These constraints typically dictate that a comorbid health condition, $C_x$, is present at a point in time (e.g. at age N, the moment of transition from $P_{i-1}$ to $P_i$), for a period of time (e.g. at least five but not more than ten years), or both (e.g. for the past two to four years). These conditions can be evaluated for logical compatibility with incidence data and the case. For instance, the instantiation of a modifier may require that $C_x$ is present at the moment of transition from $P_{i-1}$ to $P_i$. If $x \ne j$ and $C_j$ is part of the target vector $V_0$, then this instantiation can not apply in this simulation. The probability of a modifier requiring $C_{x,j}$ is therefore zero. A slightly different constraint indicating that $C_x$ is concurrent with $P_{i-1}$ for five to ten years, where $x=j-1$, may be logically possible.

Note that the outlining algorithm will select this instantiation only if the onset of $P_{i-1}$ is proposed for an older age than the onset of $C_j$. The simulator can therefore be required to add $C_j$ at an older age than the onset of $P_{i-1}$. It is important to reconcile this age of onset of $C_j$ with incidence data for $C_j$, before the tentative instantiation.

The simulation algorithm does not require that exacerbation networks reach any particular health condition prior to changes in their parent conditions. For instance, health condition $P_i$ may permit exacerbations to reach condition $E_k$, while health state $P_{i-1}$ only allows exacerbations to reach condition $E_{k-2}$. The simulation algorithm may suggest that $E_k$ developed before $P_{i-1}$, creating an intermediate vector such as $V_i=\{P_{i-1}, \ldots E_{k-1}\}$, which is in turn instantly preceded by $V_{i2}=\{P_{i-1}, \ldots E_{k-2}\}$. The simulated medical history would indicate that the patient developed $P_i$ and $E_k$ simultaneously.

Figure 7:
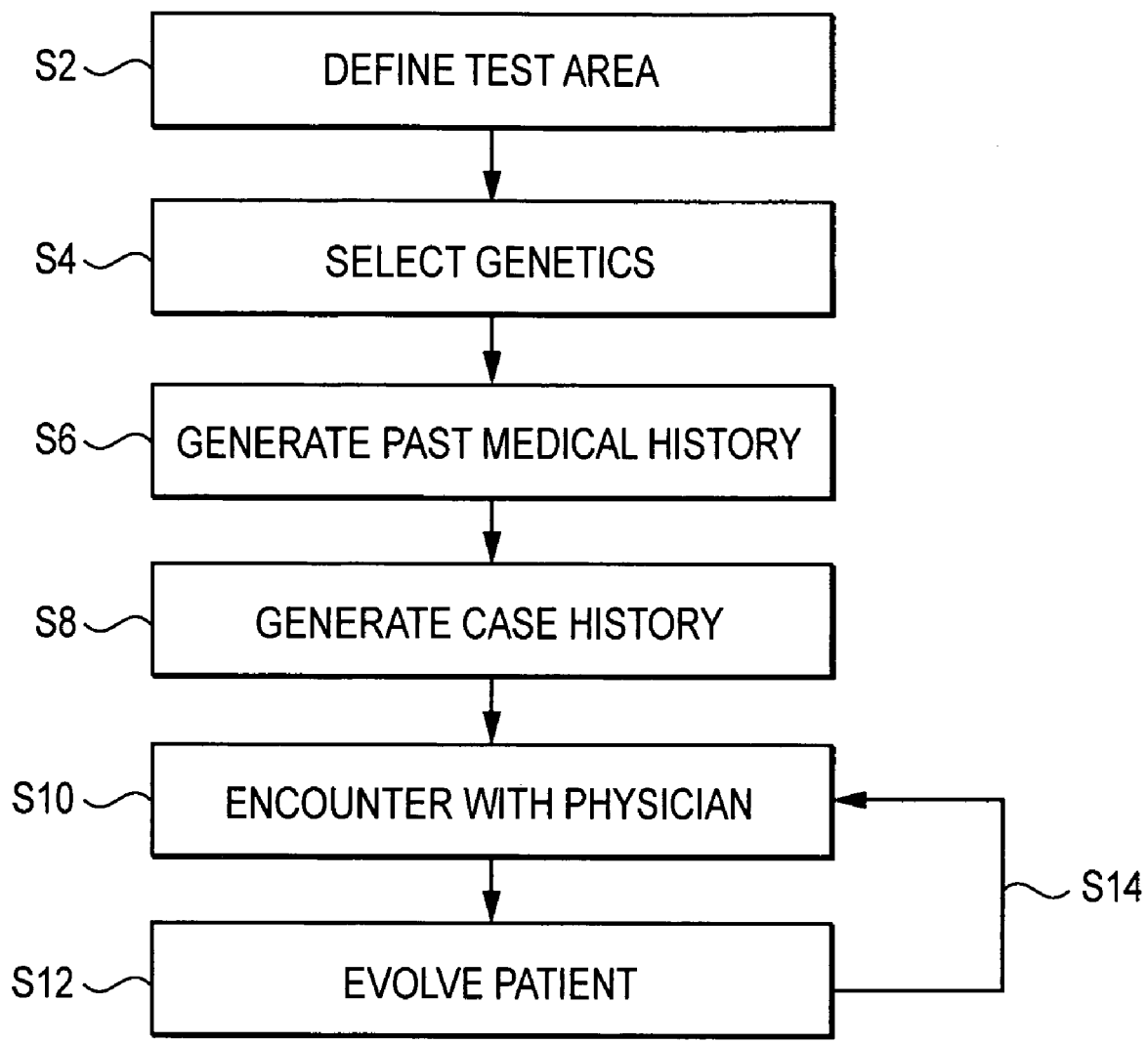
FIG. 7 is a flowchart providing an overview of the stochastic process in accordance with another embodiment of the computer based examination system of the present invention.

FIG. 7 is a flowchart providing an overview of the stochastic process. In FIG. 7, the stochastic process begins with defining a test area or subject area to be tested in Step S2. In Step S4, the sex, race, and other genetically determined facts are assigned to the prospective patient. In Step S6, the past medical history of the patient is generated, by proposing concurrent histories for each of the health conditions. In Step S8, the case history that will be accessible to the examinee is generated for use in the examination.

In Step S10, the examinee or physician encounters the patient at a predetermined stage that is suitable for the examination. The examinee makes a decision as to whether treatment or intervention is appropriate, and either performs the treatment or not. The patient is optionally evolved in Step S12 in accordance with the examinee's decision and actions performed in Step S10, and the examinee may be optionally tested again in Step S10.

Stochastic Process History Outlining Example

Consider an examination of the management of osteoarthritis. Among several cases in this area is one describing a patient with an acute flare of osteoarthritis of the knee. The case presents with established grade II chronic osteoarthritis, obesity, and No Gastric Ulcers. No other networks are active in this case. The health conditions in parallel networks are:
P: Grade 0 Knee Osteoarthritis (OA), Grade I Knee OA, Grade II Knee OA, Grade III Knee OA
C: Normal weight, Obesity, Morbid Obesity
C*: No Gastric Ulcer, Grade I gastric ulcer The health conditions Grade I Knee OA and Grade II Knee OA are associated with exacerbation networks:
$^E$grade-II: Baseline Knee OA, Acute Flare of Knee OA
$^E$grade-I: Baseline Knee OA The presenting vector is $$V_0 = \{P_3, E_2, C_2, C'_1\}$$

$$= \{\text{Grade II Knee } OA, \text{ Acute Flare of Knee } OA, \text{ Obesity, No Gastric Ulcer}\}$$

The "lead to" relations required for history generation are $PL_{1 \to 2}$, $PL_{2 \to 3}$, $PL_{3 \to 4}$; $EL_{1 \to 2}$, $EL_{2 \to 1}$; and $CL_{1 \to 2}$. The "lead to" relations required for evolution are $PL_{3 \to 4}$; $EL_{2 \to 1}$; $CL_{2 \to 1}$, $CL_{2 \to 3}$, and $C^*L_{1 \to 2}$.

The normal health condition in the $E$grade$_{II}$ exacerbation network, Baseline Knee OA, may be instantiated twice. The Acute Flare of Knee OA health condition is incident, and all other conditions are prevalent.

Age-specific prevalence data about the presenting health condition in the primary network, Grade II Knee OA, conditioned on sex, race, and other essentially predetermined and generally permanent patient characteristics are provided.

The probability of generating a white female patient, given a case of Grade II Knee OA is asserted to be 63%, the fraction of all OA cases found to occur in white females.

When sex and race are selected, the state of the prevalence node is defined. The prevalence node supplies the prevalence of Grade II Knee OA in white females as a shape defined by the points {(0 years, 0%); (25 years, 0%); (35 years, 0.2%); (60 years, 5%); (100 years, 45%)}. The prevalence of Grade II Knee OA at any specific age is found by linear interpolation, so that the prevalence at age 20 is zero, and the prevalence at age 80 is 25%. The rapid rise in prevalence from age 60 to 100 suggests a high probability of generating a very old patient, because these data do not reflect the scarcity of very old people.

To correctly simulate the age distribution of patients, an absolute prevalence is calculated using formula 1. Assume that the prevalence of the special condition "Alive" for white females is a roughly sigmoid curve with a median survival around 78 years, such as {(0 years, 100%); (1 week, 99.9%); (1 year, 99.8%); (15 years, 99.5%); 20 years, 99.2%); (50 years, 95%); (60 years, 85%); (80 years, 30%); (90 years, 8%); (99 years, 05%); (100 years, 0%)}.

Formula 1 produces absolute prevalence weights including the points {(0 years, 0); (2 years, 0%); (35 years, 0.2%); (50 years, 2.9%); (60 years, 4.25%); (80 years, 7.5%); (90 years, 2.8%); (99 years, 0.2%); (100 years, 0%)}. The peak absolute prevalence (8.77%) of Grade II Knee OA therefore occurs at age 73 rather than age 100, and absolute prevalence is skewed toward younger patients, so that the median age of prevalent cases is 71. The product of the Alive and Grade II Knee OA prevalence is similarly multiplied by the prevalence of the Obesity and No Gastric Ulcer conditions. This could further skew the age distribution away from the elderly as obesity, a risk factor for death at relatively young ages, is less prevalent in older patients.

Finally, the incidence of Acute Flare of Knee OA is obtained, if it is available. Since this health condition is part of an exacerbation network, it might be safely assumed to be equally likely to occur at any age where its parent, Grade II Knee OA, is present, if the incidence of $E_k$ is not specified. In this case, no further adjustment to the prevalence product produced above is required.

In general, the incidence shape for an incident health condition can be multiplied by the product of the prevalence shapes obtained above. One year is chosen at random from the resulting distribution in a weighted random selection process. We will assume that the process selects age 70 for this patient's presentation. This means that a white woman with a history of Grade II Knee OA, Obesity, and No Gastric Ulcer, presents at age 70 with an acute flare of her osteoarthritis.

The next process generates the past medical history of the patient, by proposing concurrent histories for each of the health conditions in the presentation vector $V_0$={Grade II Knee OA, Acute Flare of Knee OA, Obesity, No Gastric Ulcer}. The first step in this process traces health condition transitions as illustrated in FIG. 8.

Figure 8:
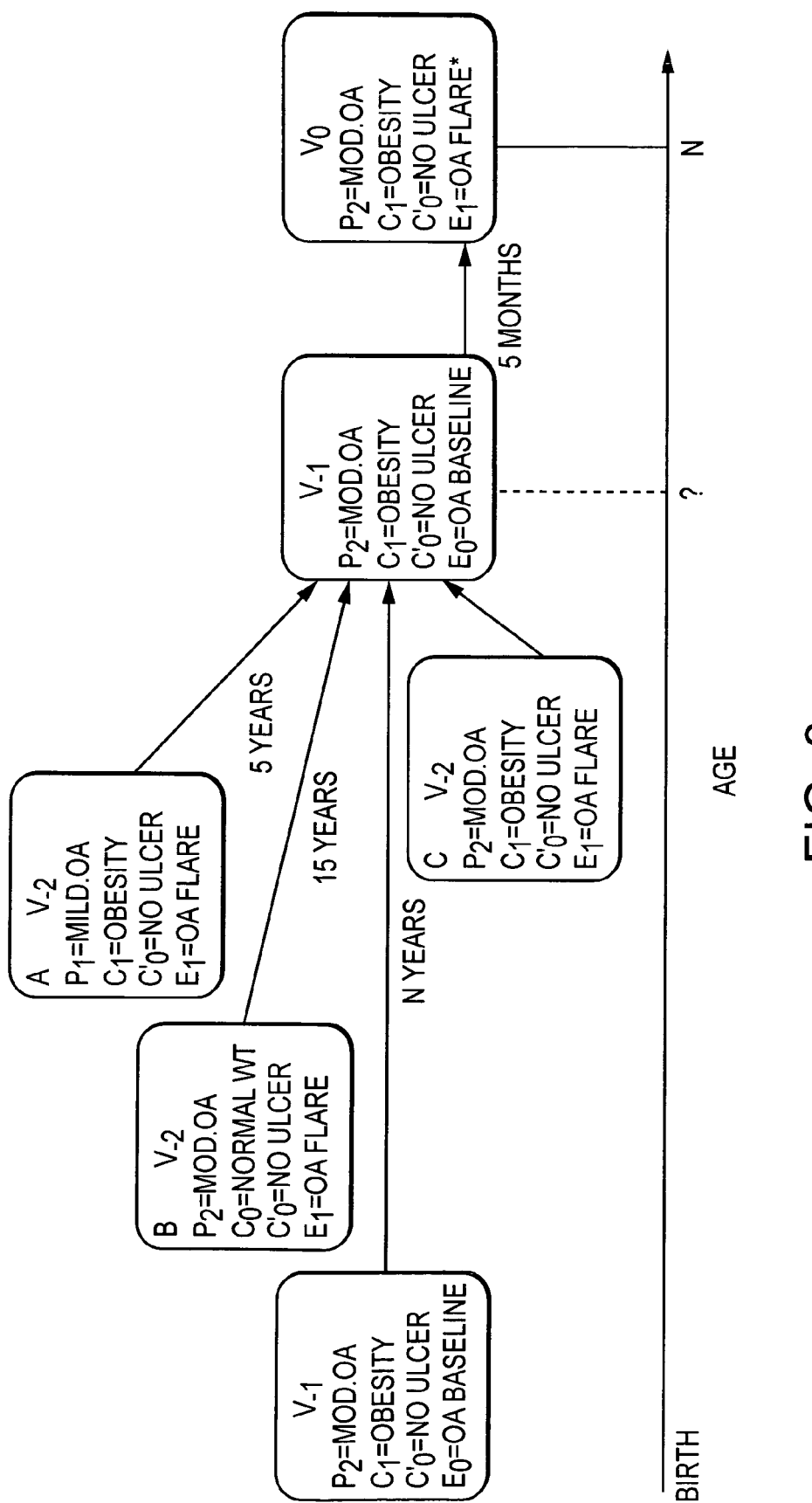
FIG. 8 is a flowchart illustrating a first step in tracing previous health conditions to generate past medical history of the patient for the stochastic process of the computer based examination system of the present invention.

As illustrated in FIG. 8, the Acute Flare of Knee OA is incident, so that its precursor, Baseline Knee OA, must be present in vector $V_{-1}$={Grade II Knee OA, Baseline Knee OA, Obesity, No Gastric Ulcer}. The age of onset of $V_{-1}$ and the preceding vector $V_{-2}$ are obtained simultaneously by predicting when each element of $V_{-1}$ might have developed, and asserting that the last predicted change did occur.

Grade II Knee OA, an element of vectors $V_0$ and $V_{-1}$, will eventually evolve to Grade III Knee OA. A history generating relation, Grade II Knee OA leads to Grade III Knee OA, describes how long this might take, perhaps 5 to 10 years. If this relation posits a shorter interval between these conditions, then the simulation is constrained to produce patients with a recent onset of Grade II Knee OA. If the history generating relation posits a longer interval, then patients may have a long established osteoarthritis condition.

Grade II Knee OA is prevalent in vector $V_0$, presenting at age 70, and with no more than 10 years allowed for evolution to Grade III knee OA, the earliest age at which the grade II condition could have appeared is 60 years. If so, this patient remained a longer time than usual in Grade II Knee OA, and the transition to Grade III Knee OA is expected shortly. The patient is most likely to have developed Grade II Knee OA between age 65 and 70, among a cohort in which no one would have progressed to Grade III Knee OA by age 70. If the incidence of Grade II Knee OA rises from age 60 to 70, the product of the reversed cumulative PDF and the incidence shapes will be further skewed towards later ages. We will assume that age 65 years is randomly selected from this product.

A similar procedure produces an age of onset for obesity. A history generating relation, Obesity leads to Morbid Obesity, describes the length of transitions, perhaps 10 to 25 years. Obesity is prevalent in $V_0$, so a reversed cumulative PDF is multiplied by the incidence of Obesity, and an onset age between 45 and 60 is proposed.

The No Gastric Ulcer element in $V_0$ is a stage 0 condition, which might evolve to stage I at some time. Since the incidence of stage 0 conditions is always between 0 and 100% at birth, but is always 0% after birth, so that the duration PDF is irrelevant to the selection of the age of onset, as long as the reversed cumulative duration PDF is non-zero at birth.

Figure 9:
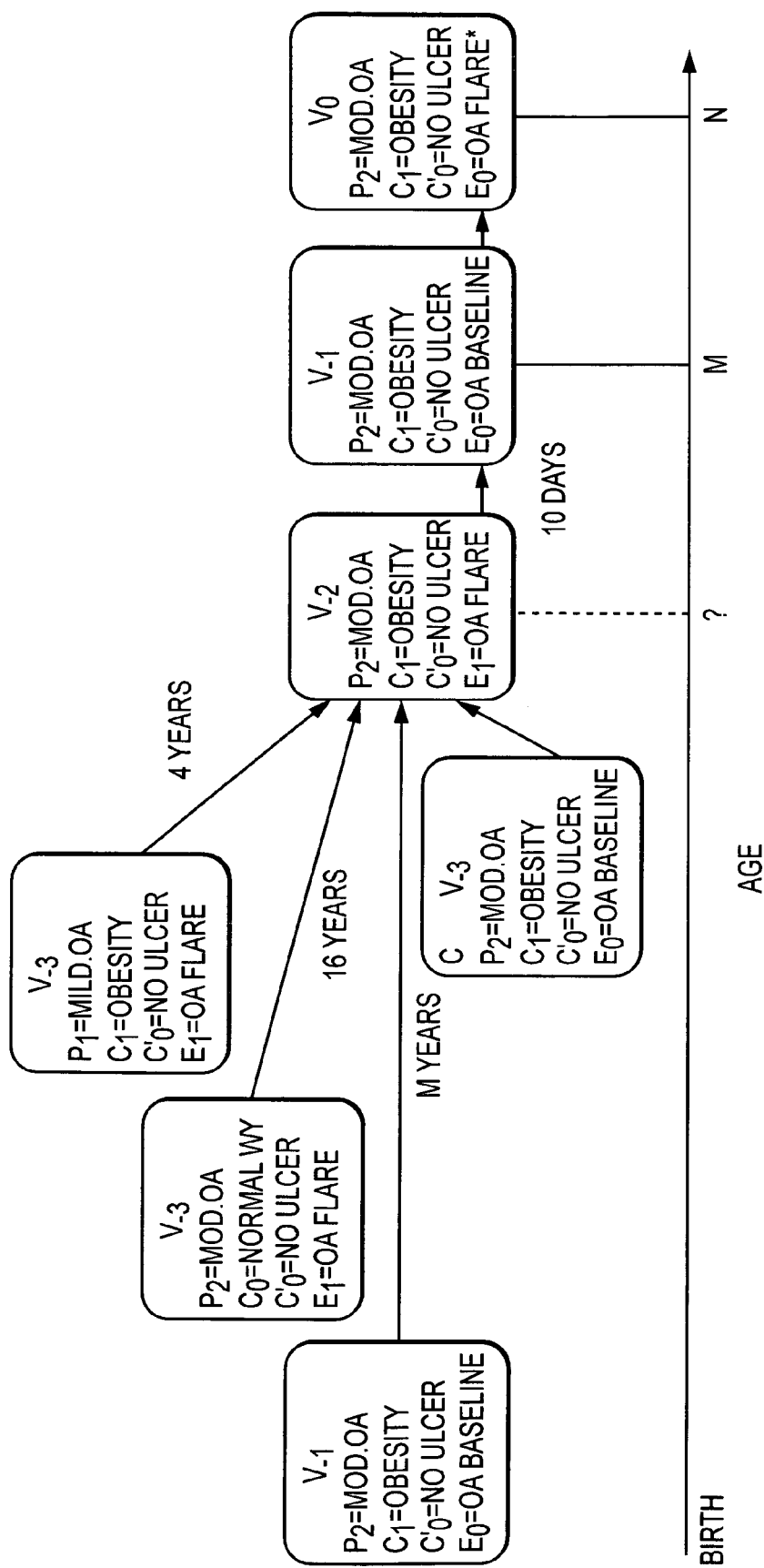
FIG. 9 is a flowchart illustrating a second step in tracing previous health conditions to generate past medical history of the patient for the stochastic process of the computer based examination system of the present invention.

Finally, the Acute Flare of Knee OA condition has a known onset time, at age 70. The history generating relation, Baseline Knee OA leads to Acute Flare of Knee OA, describes the duration of Baseline Knee OA, perhaps 3 to 12 months. If the duration of acute flares is very short, and there are no other conditions in the exacerbation network, then this PDF also describes the periodicity of flares, given the presence of Grade II Knee OA. If specific incidence data for the acute flare condition are not available, the incidence of the parent condition for the exacerbation network (Grade II Knee OA) can be substituted. The product of the reversed (but not cumulative) duration PDF and the incidence supplies a distribution from which to select an age of onset, for instance 69 years, 7 months. Since this is the oldest age proposed, it is selected and instantiated. Step 2 of this process, illustrated in FIG. 9, is analogous to Step 1 described above, and therefore, no additional discussion is described herein.

Finding Generation for Stochastic Process

Finding generation adds detailed descriptions of patients' features to the outline generated in the steps above. Beginning with a healthy newborn patient (or embryo) of the specified sex and race, the finding generation process assigns values of specific findings expected in healthy individuals. These may change when the patient develops a new health condition at the age selected by the outlining process.

The patient's detailed features are generated using modeling instructions stored as Reasoning elements with health conditions. Specific findings associated with normal health are created in a sequence indicated by these instructions. Each Specific finding is initially defined from the onset of life until age 100. For instance, the patient's height is derived from a randomly generated percentile and a set of shapes resembling a pediatric growth chart extended to age 100. The set of shapes used may be conditionally dependent on the sex, race, and any other established facts about the patient.

The finding generation process should generally create dependent findings, e.g., knee pain, after generating the findings upon which they depend, e.g., joint space narrowing. Careful selection of findings to represent may reduce some dependencies. For example, the model in general is more robust if height and body mass index are considered to be independent findings, and weight is not calculated until explicitly requested during a simulation. Therefore, the model in general is more robust if height and body mass index are considered to be independent findings, and weight is not calculated until explicitly requested during a simulation. Most findings are instantiated as a series of pairs of values and ages. Values at other ages may be found by linear interpolation.

Findings may vary with predictable circadian, lunar, and annual rhythms, described by shape subpatterns. Shape subpatterns can be combined with a shape to produce fluctuations on realistic temporal scales.

Finding distortions illustrate events having temporary effects on the shape of some value. For instance, a temperature shape during a febrile illness might be 39° C., with a distortion pattern indicating a 1° C. drop for four hours following administration of acetaminophen. The exact temperature reported at a given time would depend on the current value of the lifetime temperature shape and whether the patient consumed acetaminophen in the last four hours.

After determining patterns for all findings present at a point in time, the simulator proceeds forward in time to the next health condition vector. The simulator updates findings for the new situation. This loop continues until the computer has described the findings of the patient in the final health condition vector.

Using Pre-Generated Patients

In accordance with one design of the present invention, when the computer based examination system generates and evolves a random patient, it cannot reuse the patient information if the patient is evolved once. That is, every time the examination is executed, we need to generate a patient to continue the test. Not only does the process of generating a patient take tremendous time, but also the evolved patient cannot generally be tested again in the future.

In accordance with another design of the invention, the patient is pre-generated, evolved and stored in the Whiteboard database. The presentation system can test the patient in countless time if wanted. Furthermore, different physicians can test the same patient at the same time.

Figure 10:
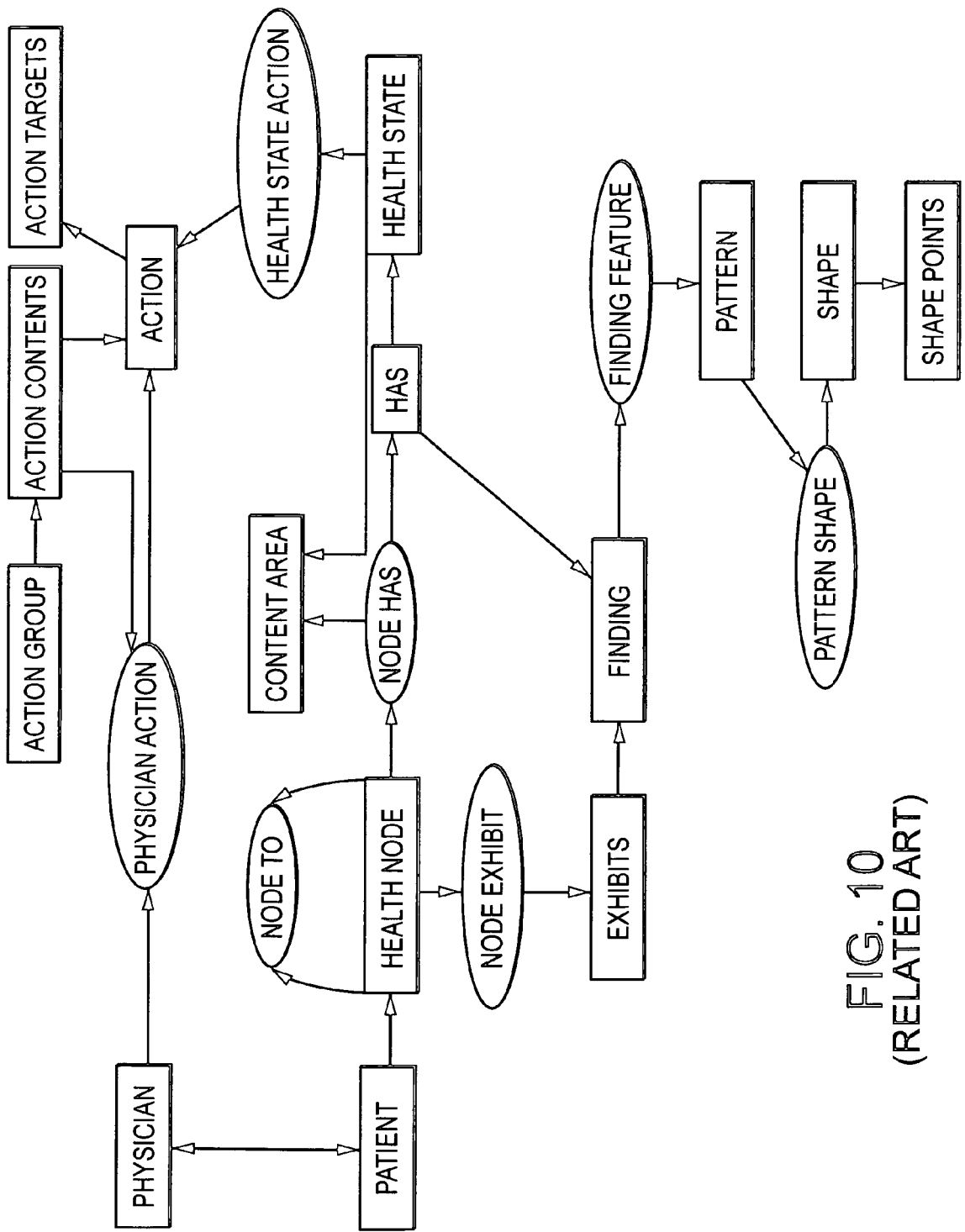
FIG. 10 is an illustration of the entity-relationship model data structure stored in the white board database when patients are not pre-generated.
Figure 11:
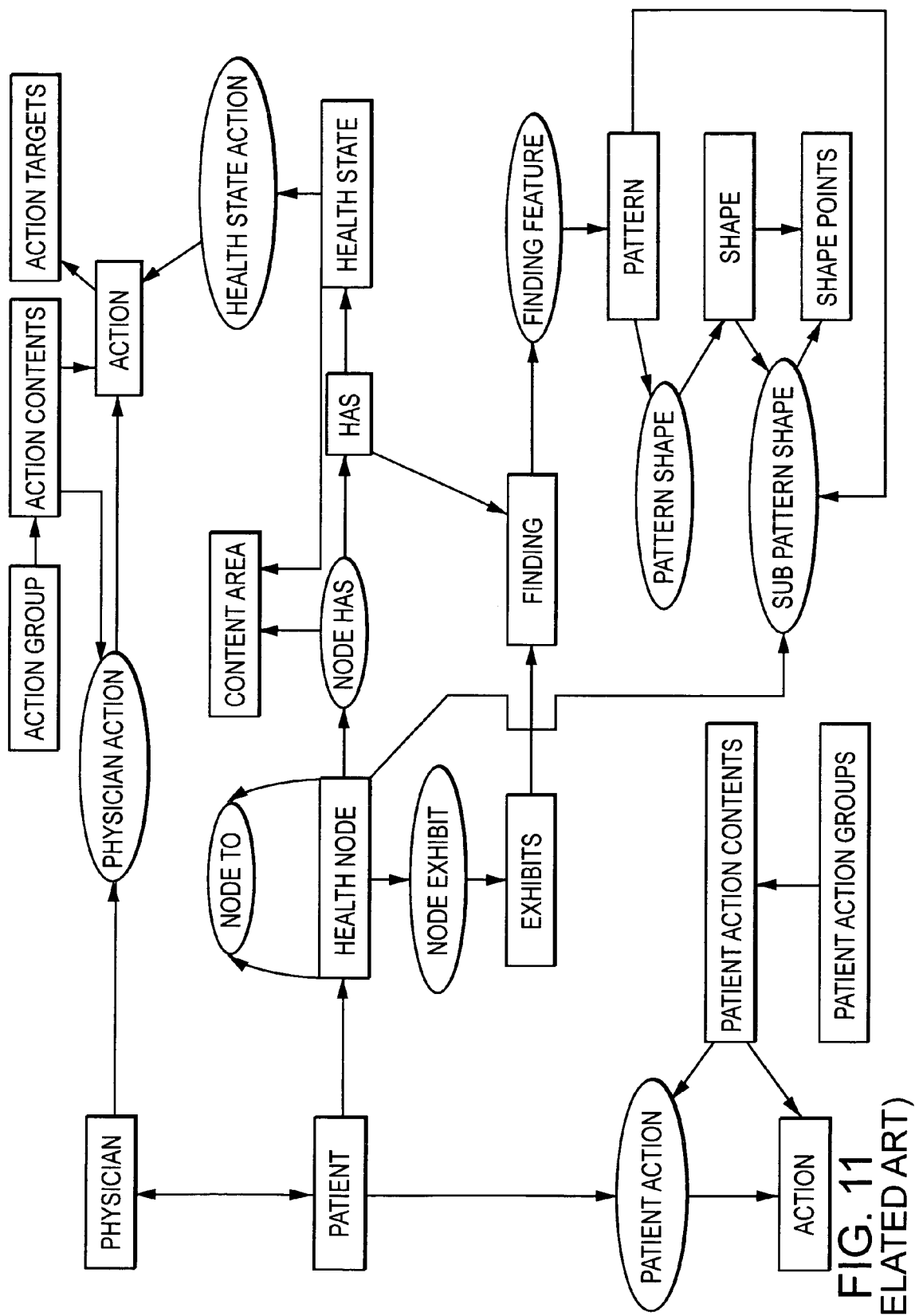
FIG. 11 is an illustration of a modified entity-relationship model data structure stored in the white board database when patients are not pre-generated.

FIG. 10 is an illustration of the entity-relationship model when patients are not pre-generated, and FIG. 11 presents the modified entity-relation diagram of the modified Whiteboard database when the patient is pre-generated. Each node represents a status of a patient with parallel health states. For example, when a patient is generated, he or she is located at node 1, the patient might be evolved to several status located at node 2, 3, 4 . . . , etc. Therefore, a patient can have many nodes.

Many nodes can share same EXHIBITS and HAS. For instance, when a patient is evolved to a severe knee problem, we first take out the most updated EXHIBITS of the previous node, modify it and then write it to the new node, and at the same time generate a new EXHIBITS for the new node. The new node will point to the EXHIBITS prior to the most updated EXHIBITS of the previous node. If nodes are in the same content area, they also share the same FINDINGS and PATTERNS, but their shapes are different, which can be found in table Pattern_Shape.

Since different physicians can use the same patient for the test at the same time, the corresponding action contents needs to be given for each physician. Therefore, every time a patient has a new node, we also generate the patient's action contents. When the physician gets to the patient with the specific node, the action contents are copied to physician_actions tables.

The table ACTIONS, HEALTHSTATE and ACTION_HEALTHSTATE are pre-generated, and a corresponding utility integrated with pre-generating COA is created. Accordingly, the evolution process for pre-generated patients is, for example, as follows:

a) Based on the parallel health states of the patient at the specific node, fetch all corresponding actionID from action_healthstate.
b) Based on the possible target of each actionID, construct all combinations that lead to different parallel health states.
c) Create a new node for each possible action combination.
d) Copy the SHAPE from old node to the new node.
e) Construct a tuple in table NodeToNode where the action combination, old nodeID and new nodeID will be stored.

Generating Patients with Parallel Health State Networks

A detailed description of parallel health state networks is now described. We have determined that parallel health state networks provide a model with a reasonable biological basis, more easily defined data, greatly improved reuse potential, and a better segmented implementation. Evolution of synergistic health problems (e.g., vicious cycles) are managed using structures from the original data model. A working patient generation process is creatable using the parallel network model.

We have determined that the number of conglomerate health states expands combinatorially, and the incidence and duration of these conglomerate health states is often a matter of speculation or is redundant with previously stored information.

We have also determined that a parallel network approach improves on the accessibility and reusability of health state data, while retaining the ability to handle the dependencies inherent in synergistic cycles.

Humans are composed of inter-dependent cells organized into tissues and organs. Some tissues directly or indirectly control the state of cells in other organs through mechanical, neurohumoral, or other processes.

An individual's health reflects the current health of all of these cells. Therefore, a very high resolution model of the life of a human body might describe the histories of the cells comprising the body, including their dependency on other cells. In clinically recognizable processes, the cells comprising one tissue share similar structure, function, and health with many of their immediate neighbors. Their health may diverge rapidly from the health of the cells in other tissues. Therefore, a model concentrating on the histories of tissues retains considerable resolution.

Each tissue can be imagined to evolve on its own standard schedule unless some local insult occurs, or an insult to another tissue alters the schedule. The normal tissue schedules proceed in parallel. For instance, bone, Islets of Langerhans, nephrons, and retinal tissue all gain and lose function at predetermined rates. If bone loses function (strength), a local pathological parallel process (fracture) becomes more likely. If Islet cells lost function (insulin secretion), distant pathological parallel processes in nephrons and retinas become more likely or progress more rapidly (diabetic nephropathy and retinopathy).

Without parallel networks, distractors, such as randomly appearing colds or a history of appendicitis might require many conglomerate states. Also, information collected for one disease domain might have to be completely replicated in other domains (for instance, obesity descriptions would occur in osteoarthritis, diabetes, hypertension, combinations of the above, and independently).

We have also determined that many therapeutic complications are acute site-specific illnesses superimposed on an antecedent illness. On the other hand, some problems interact in synergistic cycles: Osteoporosis increases the likelihood of fractures, and immobility (following a fracture) increases the rate of progression of osteoporosis. Consequently, many of the most interesting disease processes are intertwined with others. In a network of conglomerate health states, these dependencies can be explicitly described at nodes and along edges between nodes. In a parallel network model, the interacting networks must be aware of each other.

This view of health and function, we have determined, suggests a definition of parallel health state networks: A parallel health state network for a tissue describes a collection of clinically discoverable and mutually exclusive states in which that tissue may exist, and possible transitions between states. For example, the normal development of a tissue, described from a person's birth to death, is one distinct state in a network.

Physically separated cells of the same tissue type may exist in very different states. For instance, the left and right knee joints are susceptible to pathologically indistinguishable osteoarthritic changes, but one knee may exhibit more advanced changes than the other. Therefore, parallel networks require identification of involved sites.

A parallel network is, not coincidentally, a disease staging scheme. Parallel networks for chronic diseases are typically restatements of familiar staging concepts (e.g., Stage 0 or no disease, followed by Stage I or mild disease, and so on). The parallel network illustrates these as sequential stages, even in acute processes such as ankle sprains or burns. A third degree burn is always preceded by a second degree burn, if only for the briefest moment of time.

Parallel networks alter knowledge acquisition and storage requirements, as well as patient generation algorithms, when compared to conglomerate health state models. Diagnoses previously combined in a conglomerate state become distinct states in different parallel networks. The conglomerate health state of the body is described by a vector indicating the current status of all parallel networks.

Figure 12:
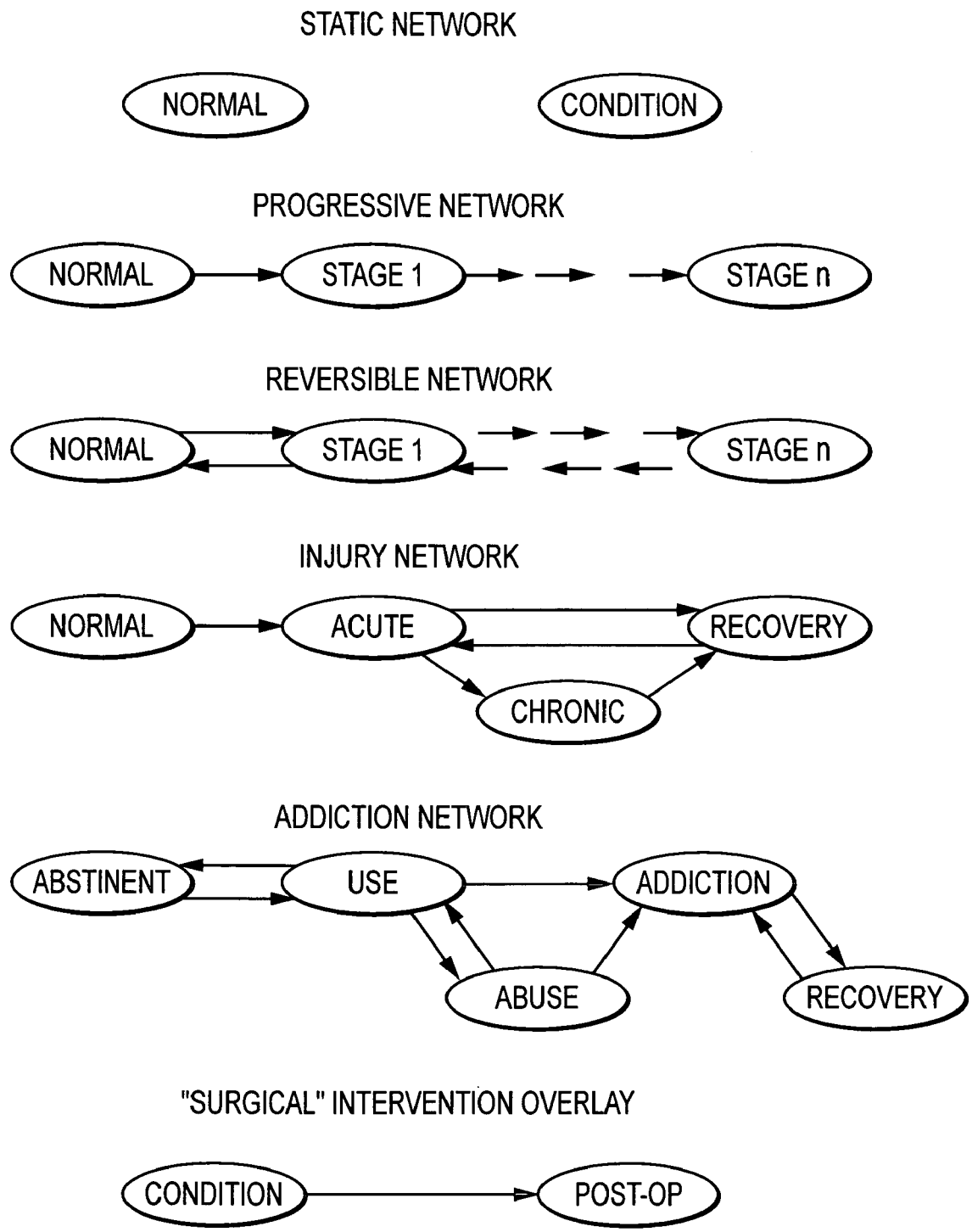
FIG. 12 is an illustration of parallel network structures for the computer based examination system of the present invention.

Illustrations of their disease domains help medical experts understand the scope of their knowledge acquisition task. Initially intricate domain models were decomposed into much less threatening parallel networks. FIG. 12 illustrates parallel network structures. The simplest network is a collection of one or more static states, typical of genetic (e.g., Down's syndrome) and some congenital conditions (e.g., anencephaly). The progressive network is a series of states with no cycles, typical of degenerative illnesses such as osteoarthritis. The reversible network illustrates chronic but reversible conditions, such as essential hypertension and weight disorders. In the injury network an acute insult evolves to either recovery or a chronic condition with a later recovery. Injury networks describe many infectious diseases and trauma.

The addiction network illustrates that a person may abstain from, use, abuse, or become addicted to something; in the current model, a previously addicted person can only be addicted or recovering, but cannot return to abstinence, use or abuse. The surgical intervention overlay illustrates that new states can be added to the above networks using irreversible therapies such as radiation or surgery.

Parallel networks of three types are identified. The primary network contains the diseases that define the domain, such as diabetes mellitus. The second type of network contains a risk factor for progression through the primary network, such as obesity. The third type of network includes complications attributed to states in the primary network or its management, such as retinopathy.

We have also determined that the following information is used to create parallel networks: 1) how long a risk factor should exist before it could influence a transition between states in a primary network, 2) the time required for transitions in the primary network, given different combinations of risk factors, and 3) the number of passes an individual patient should be allowed to make through a cycle (e.g., from acute injury to recovery back).

The data model objects originally intended to store risk factors included a "Person HAS Health State" relation, which identified a health state, its onset and duration. In addition, HAS relations indicates a preceding HAS relation to support tracing of medical histories. These attributes are adapted to describe parallel synergistic networks.

The patient generation process uses a weighted random process to select all times and events, starting with an age of onset for a health state on the primary network. Risk factors are selected next. Unlike the conglomerate health state patient generation algorithm, any diagnoses associated with altered risk must be described in a parallel network. The plausible range of duration for each risk factor is stored in a HAS relation, and used in selecting its onset age. If the risk factor evolves independently of the primary network, the HAS relation does not indicate a preceding HAS, and the algorithm creates the risk factor history using default assumptions in its parallel network. If the primary network does interact with the risk factor, the preceding HAS relations provide time constraints that promote plausible concurrent evolution of the primary and risk factor networks.

The original history generation algorithms are used within independently evolving parallel networks. Consequently, the system continues to support conglomerate health states described as a parallel network. In contrast to the conglomerate health state model, the parallel network technique may require explicit and separate generation of the histories of the primary network and any number of risk factors.

Computer Implemented Process

Figure 13:
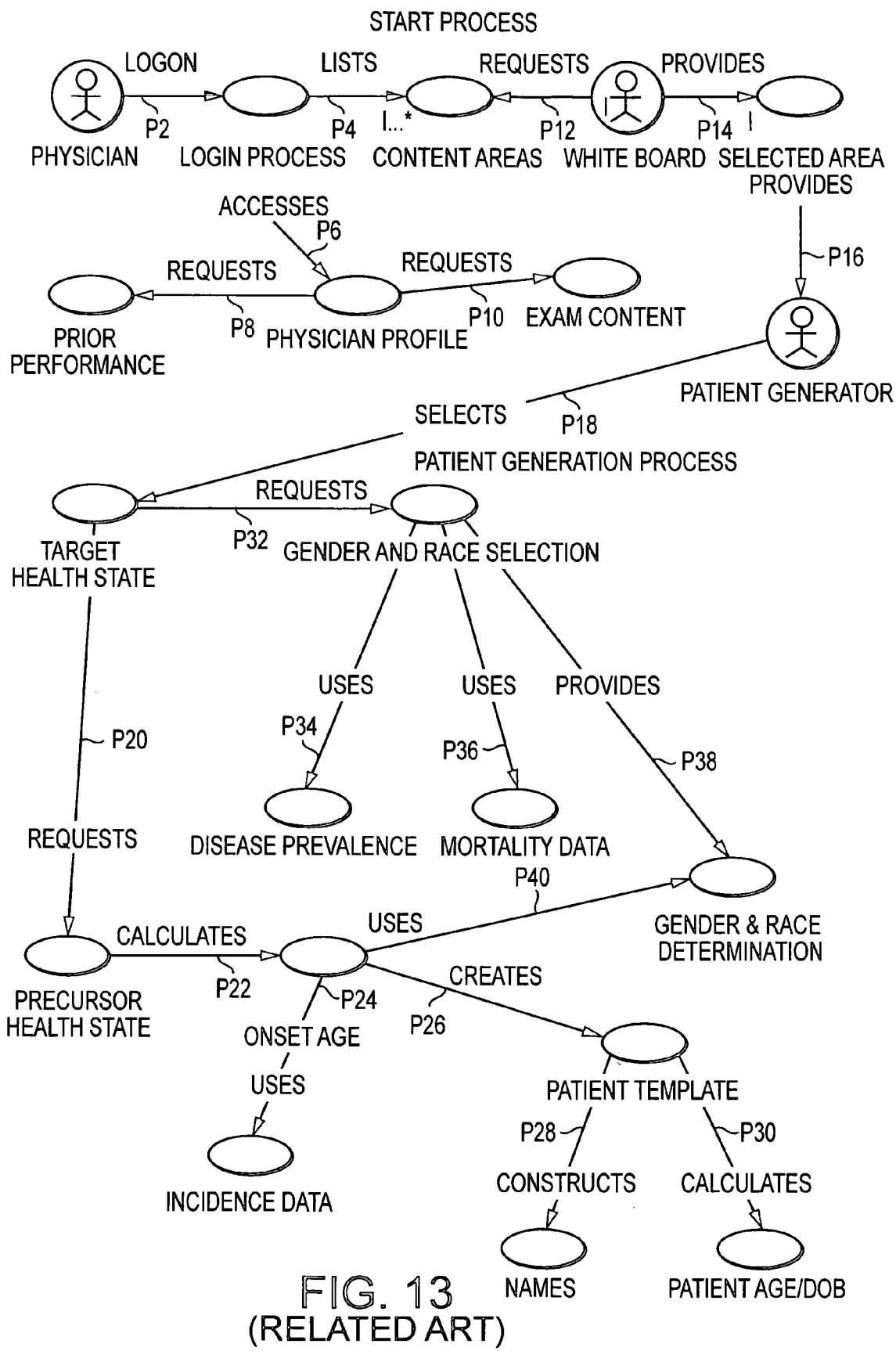
FIGS. 13-14 are detailed flowcharts of the process of the computer based examination or assessment system of the present invention.
Figure 14:
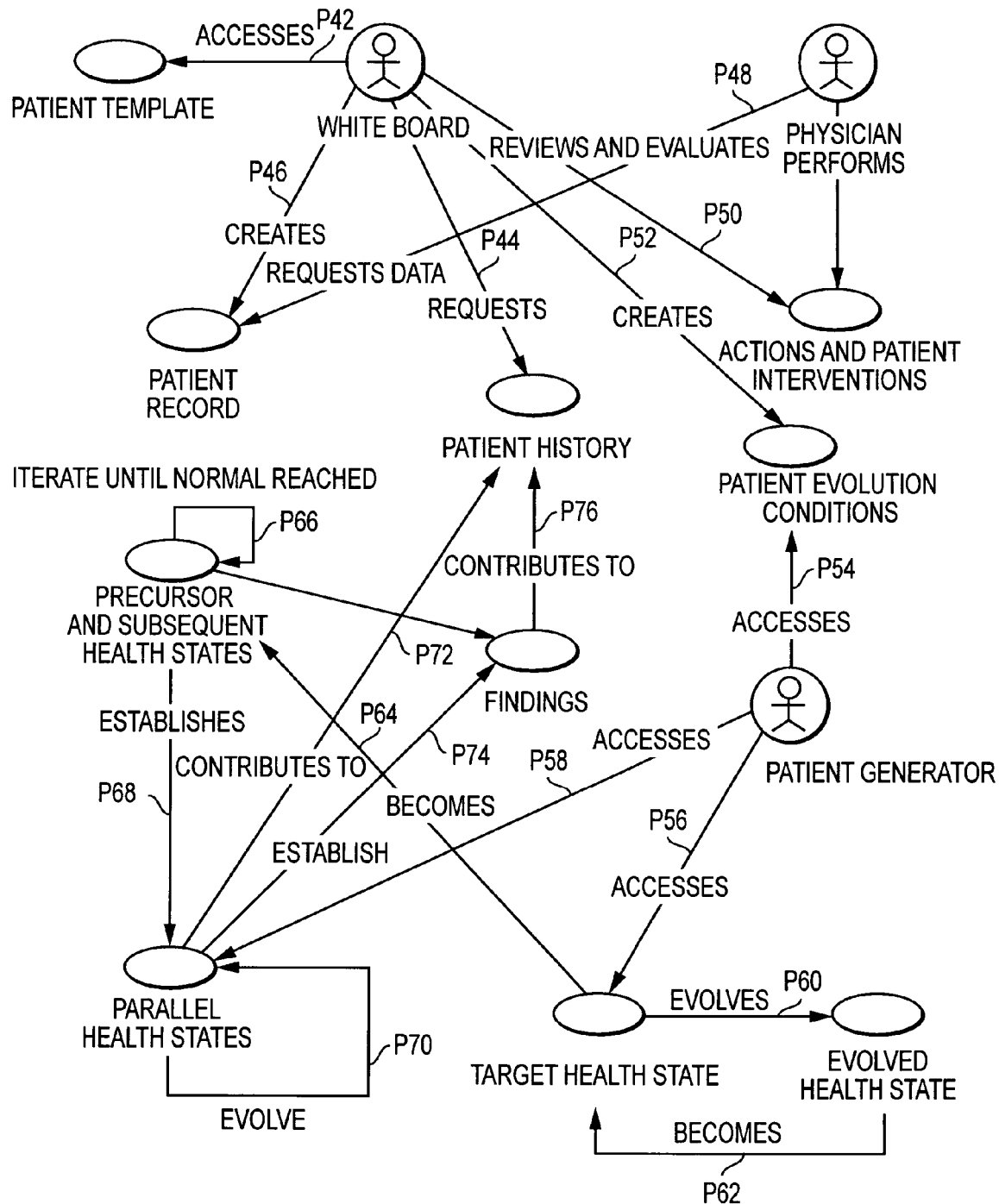

The process of the computer based examination or assessment system is described in detail in connection with FIGS. 13-14. The computer implemented process includes the overall concept that the physician is presented with an examination, and the process generates multiple instances of patients. These generated patients represent clinical scenarios that a physician would have to go through to administer proper treatment. These scenarios are stored in a white board database which stores both the database implementation (i.e. the patients stored in data structures), as well as computer codes which operate from base structures including information on physician.

There are three basic actors in the computer based examination system: physician, white board and patient generator. The physician/examinee initiates the white board action by logging in. Once the examinee logs in, then the white board makes one or more requests to the patient generator. The white board generally provides the patient simulator with the basic testing area. The patient generator then starts the process of generating the patient and evolving backwards, and optionally forwards in time for pre-generated patients. Thus, the computer based examination system includes separate programming objects in the general C++ programming sense for physician, the patient and the white board.

In general, the physician/examinee pre-registers to take the examination, and provides (or the system already has stored) detailed background information on the physician, areas of weaknesses, prior examination information, and the like. Thus, the physician logs-in to the computer based examination system in Step P2, and the system validates the physician in accordance with predetermined criteria, e.g., user ID, password, correct examination, and the like.

The physician/examinee is either presented with an optional list(s) of subject areas for examination or mandatory subject areas for examination in Step P4, responsive to information stored in the whiteboard database via requests thereto in Step P12. Alternatively, the examination areas might be hidden, and the examinee might be told that this is a diabetic problem, with certain management issues. The examinee may optionally have a series of selections, whether it is in terms of individual patients or they could be in specific areas.

In some instances, the examinee may be provided a patient with some specific statements about the patient. The computer implemented process may optionally determine whether the physician has been examined before. If the answer is yes, then the physician might require, for example, five of fifteen specific subject areas for the examination, of which one or more would be available for testing.

In addition, prior performance of the physician may also be considered using a pre-stored or generated physician profile via Step P6, and requests to the prior physician performance via Step P8. The specific exam content is then requested in Step P10 responsive to at least one of physician profile, prior performance, content areas. Accordingly, one or more of prior performance, the physician profile, the content of the examination, are used to provide a selection list of the physician to choose from in Step P14.

Depending on the above information, the patient generator process is then initiated to create a patient for the examination in Step P16. The patient generation process may be performed in Step P18 in real-time for each patient, or may be pre-generated as described above. Under the real-time scenario, the selection of a problem area in Step P14 translates into a target health state or area.

For example, if the problem area selected was diabetes, the target health state in the knowledge base would be diabetes. Using the target health state, there are generally a plurality of health states associated therewith. The computer implemented process then optionally randomly selects one of these areas as a precursor health state in Step P20. For example, a mild case of diabetes may be the precursor health state for normal health state of diabetes.

The selection of the precursor health state is based on, or calculates, onset age in Step P22 via incidence data in Step P24. The history generation computer process is a mechanism that sets up a reasonable beginning time and ending time for the patient that is being presented. The computer process chooses a target health state, precursor information, sex and race from the target health state, and establishes the age of the patient. The computer process then moves backwards in time to establish onset age when the condition occurs, and proceeds backwards in time all the way to the normal state. Next, the process moves forward in time to determine potential subsequent health states for the patient based on a variety of possible interventions performed by the examinee. Thus, the process has two stages.

Depending on the precursor information/health state, information such as the sex and race, along with disease prevalence in Step P34, mortality data Step P36 and incidence information in Step P24, are used to select the specific sex and race for the simulation.

The mortality data is based on sex and race. The sex and race is selected from the health state, incidence or prevalence data and sex and race specify mortality data. For example, if the health problem that is presented to the examinee is new to the patient, then it is incident (e.g., a recently broken bone). Alternatively, if the health problem is an old established problem such as long term diabetes, the health problem is prevalent. Thus, the incidence and prevalence is inserted into the patient case history over and over again depending on the particular problem. Accordingly, a pre-determined decision is generally made as to what types of disease are to be tested, prevalent disease or incident disease.

The sex and race selection uses the disease prevalence and mortality data in the sex and race selection process. The mortality data and disease prevalence are used to establish the reasonable ages and sexes, and also ages of on[−]set. For example, this mechanism prevents generation of pregnant males, 14 year old Type-II diabetics, and the like.

For example, the computer system determines, or is instructed as described previously, that the problem area is arthritis. The sex, race, and age of the patient are determined, for example, at the point in time where treatment may be necessary. The patient history is then generated back through the process/time to establish onset times of the various different health states. That is, from, for example, the point in time where the arthritis is severe, the patient history is generated at a point when the arthritis was mild, and back to when the arthritis was substantially normal.

When the sex and race selection process is completed via the combination of sex and race selection in Step P38 and onset age calculation in Step P40, a patient has been generated at a specific point in time with a specific health state problem and the characteristics of that problem. Thus, the computer process has generated the patient, moved backwards in time from the disease onset age all the way back to normal. For example, if the computer process started with a mild condition for a specific disease, the computer process goes backward one time interval to normal from mild. If the computer process begins with moderate, the computer process will move backward in time from moderate.

As a result of the computer process, a patient template is also generated in Step P26 using the onset age determination in P40 and sex and race selection in Step P38. In addition, the generated patient is given a name in Step P28, and age including a date of birth in Step P30. The physician/examinee is then provided with the history of the patient for use in diagnosing or prescribing treatment for the generated patient. The patient history includes, for example, age of the patient, race and sex. Up to this point in the computer process, the patient is created. From this point of the examination/computer process and forward, the patient and physician's interaction with that patient determine both the information provided to the physician/examinee, as well as potential evolution of the patient. Changes in the patient's characteristics is a function of physician's action or inactions using the evolutionary process described below.

The evolutionary process is performed using the knowledge base structure or entity relationship model described in detail above. The knowledge base structure has been separated from the white board structures described above for administrative purposes, but alternatively may also be combined therein. The knowledge base represents all the information that does not necessarily have to go with the patient for purposes of presentation to the examinee. The knowledge base includes information used to create the patient and provide instances of information.

However, separating the knowledge base from the white board structure has the advantage that the computer generated patients do not require as much data to be transported therewith. Accordingly, a separate structure is created called the white board structure. The white board structure advantageously includes the information required to generate the patients and to present the patients to the physician/examinee. The white board structure includes information containing patient description and all the findings that are typically generated that are not necessarily related to the problem, for example, blood pressure, blood glucose, and the like.

That is, the white board structure provides all information that is generally available to the examinee, such as information satisfying examinee queries on prior history, laboratory tests, and the like. In addition, when pre-generated patients are used, all findings associated with the patient including all pre-generated evolutionary states are also stored in the white board data structure.

For example, if the patient had moderate arthritis, the patient may generally transition to two other health states: severe arthritis, or mild arthritis. Thus, in one embodiment of the invention, the computer process pre-generates the possible health states for the patient. According to this embodiment where the patient is pre-generated, the process of evolving a patient may, in some circumstances, be more computationally efficient than to generate the patients dynamically. Thus, for pre-generated patients described above in detail, all possible states are generated ahead of time and then used by the white board structure in accordance with the pre-generated state when activated or selected by the examinee.

The white board accesses the patient template in Step P42, and generates the patient record in Step P46, responsive to requests initiated by the white board to the patient history information in Step P44. The patient record is not generally reviewable by the examinee, except on individual requests by the examinee in Step P48. The examinee requests information from the patient record in Step 48 which provides the examinee the physical view of the patient. For example, the patient's blood pressure may be stored in the patient record for retrieval by the examinee. Other examples of information stored in the patient record include chief complaint, past medical history, past patient behavior or compliance information.

The white board will also generate examinee actions and patient interventions in Step P52 by reviewing and evaluating the physician intervention in Step P50, responsive to the patient record. The examinee actions and patient interventions contribute to the patient evolution conditions used in the patient evolution process described above in detail.

Whether the patient is pre-generated or not, the computer process/patient generator generates the initial patient, and subsequently evolves the patient, and subsequently presents same to the examinee. The patient is generated by the patient generator accessing the patient evolution conditions in Step P54, the target health state in Step P56, and any existing parallel health states in Step P58. The patient is evolved by the patient generator in Step P60 to the evolved health state, which may become the target health state in Step P62.

At this point we have a patient on the white board presented with a particular health state, which typically is the form of a chief complaint. From this time on, the examinee/physician takes control of the process, and nothing is going to happen in the computer based examination system unless the examinee/physician does something, unless the health state is time dependent and able to advance to another state automatically, such as by inaction on the part of the examinee.

For example, if the health state is an acute problem, such as a heart attack, there may be a time dependency built in that is going to force some action of the physician within a specific time before the patient experiences another heart attack. In this example, the examinee using the computer based examination system may dismiss the patient, the patient will walk out of the doctor's office/hospital, and the examinee would receive notification that the patient just showed up in the emergency room with a problem.

Alternatively, if the examinee is too slow in diagnosing an illness, the inability to treat the patient in a short period of time may also result in the patient progressing to a different health state. For example, a patient that has a heart attack might progress to a more serious state if the examinee does not perform corrective measures very quickly while the patient is, for example, in the hospital. In general, allowing time to elapse without intervention is an intervention choice along with the other active interventions that an examinee might choose.

In order to determine the target health state, the "iterate until normal reached" process is initiated via Step P64 which sets one or more pre-cursor health states to the target health state. The "iterate until normal reached" process iterates in Step P66 until the normal health state is reached backward from the target health state. For example, if a mild health state is selected, the precursor health state is normal. The "iterate until normal reached" process also establishes one or more optional parallel health states in Step P68. Precursor parallel health states are then generated as needed in Step P70, which are then used to contribute to the patient history in Step P72.

The computer based examination system ensures that the age of onset for the various parallel health states is reasonable. Thus, the process of generating precursor health states for the parallel health state is a multi-dimensional process of monitoring health states to be consistent, to prevent unreasonable scenarios, time frames, and the like. If the parallel health states are related, they have to be related to each other sufficiently enough so that the evolution of health states makes sense.

The parallel health states are also used to establish the findings in Step P74, which contribute to the patient history in Step P76. While the above steps have been described in, more or less, a sequential manner, it should be clear that the various steps described herein may be performed in parallel, independently, and/or non-sequentially, as needed or for computational efficiency.

Advantageously, the computer implemented process includes the capability of utilizing parallel health states as part of the patient generation process, which is described above in detail. As part of the generation process, a decision is generally made to include or exclude those particular parallel (e.g., morbid or co-morbid) health states along with the original state of the disease.

We have determined that sometimes health problems tend to be concurrent, but they are not generally defined as being necessarily interrelated. The computer based examination system provides the feature of handling a plurality of health states, either related or not related to each other. For example, there tend to be lots of people with diabetes and high blood pressure. Accordingly, we define these two health states as related to each other. Alternatively, the plurality of health states may be considered to be substantially independent and still within the scope of the computer based examination system of the present invention.

The present invention further provides the feature of dealing with parallel health states substantially or completely independent of each other to permit dependent or independent management decisions. For example, a person that has diabetes and high blood pressure generally requires slightly different management decisions than a person who just has high blood pressure or a person who just has diabetes. For example, the physician/examinee may prescribe a more expensive anti-hypertensive drug if the patient has both diabetes and high blood pressure because of potential complications unique to the combination of health states. Thus, the computer based examination system may be used to determine whether the examinee has made the appropriate management decision. Alternatively, the computer based system may be used to collect various responses from different well recognized physicians to establish a minimum level of care for insurance companies, health care organizations, other physicians, and the like.

The present invention also provides the feature of providing distractions when attempting to diagnose the disease/illness. That is, the patient may include symptoms and/or indications that might be related to the problem seemingly presented to the examinee, but, in fact, these indications distract the examinee along an inappropriate path, such as excessive testing, over-prescribing medications, and the like. Accordingly, we have also determined that distraction makes a good argument for having parallel problems.

At this point and time, the computer based examination system selects an area for examination, and is in the process of working backwards in time. The process iterates from precursor health state down to the normal health state, where at each precursor state the process considers potential co-morbid problems. Both the precursor or subsequent health states are the primary problem, and the parallel health states generate findings. The findings are a part of the patient history. For example, a finding of obesity might be a change in weight. The process moves backwards while at the same time looking at potential parallel health states have been substantiated. The history of findings are generated at the white board level.

Now if the physician takes some action at this point in time that causes patient evolution (that is, the physician causes some action which the white board is checking at this point and time), the white board matches the action up against something that is going to cause patient evolutionary health state change. The white board then makes a request to the patient generator to evolve the health state.

If the full patient has been generated on the white board, then the patient generator is replaced with the white board itself to provide a pre-evolved patient from memory. If, however, the knowledge base is linked for a dynamic situation, then the patient generator dynamically evolves the patient. In either situation, the evolved health state becomes the target health state at this time. For example, the health state has evolved from mild to moderate arthritis, or from mild obesity to moderate obesity.

The computer implemented process also includes the possibility of treating patients with management health issues that do not generally become totally normal (e.g., long term diabetes, arthritis, and the like), as well as health conditions that may return to completely normal (e.g., broken bone, and the like).

In fact, we have determined that it is particularly likely that patients will revert to normal conditions when the patient experiences an exacerbation health state/condition for the computer based examination system. For example, we have determined that an exacerbation condition can have, for example, mild, moderate and severe states. If the patient has a moderate exacerbation, there is a chance that the patient experienced a mild exacerbation before evolving to the moderate state. There is also a chance that the patient had a severe exacerbation, is now recovering, and may return to the normal state a few minutes later.

In summary, the computer based examination system utilizes three actors, the white board the physician and the patient generator. The examinee initiates the whole process by logging in. The examinee logs into the white board, and the white board accesses various information to determine whether the examinee is valid. If the examinee is valid or verified, the white board looks up the examinee's profile to determine any background specifics on the examinee, such as specific areas needing improvement, past examination results, and the like.

The white board then determines or is provided the exam content, and then contacts the patient generator. The patient generator begins the generation process, selects the disease or subject area, and controls the actual combinations of health states and co-morbid health states via a case structure. The case structure controls both the presenting health state as well as the co-morbid health state. The case structure filters the generation process and makes a predetermination to eliminate predetermined impossible situations, or difficult or unimportant situations that are not to be used in the testing. The case structure indicates that even though a specific health state or parallel health state is in the knowledge base and even potentially legitimate, the case structure will not present that problem. Thus, the case structure simply controls which of the health states will be presented to the examinee, and which of the co-morbid health states, and possibly flare states will also be presented to the examinee simultaneously or sequentially.

The white board then retrieves the patient template including, for example, the patient history, the chief complaint, the assessment test, and the like. From this time on, the examinee performs some action by either requesting data which is controlled by the white board or by causing, directly or indirectly, some action to take place. Once an action is performed, the patient may be evolved to the next health state by the patient evolution process.

Both the request of information and the review and evaluation of the examinee's actions or intervention are generally handled by the white board for convenience, but multiple control mechanisms may also be used. If the white board sees there has been a change in health state for the patient, then the white board would then go to patient evolution process to initiate the evolution, and request the patient generator to provide information regarding the evolved patient.

The patient evolution information may optionally be pre-generated for computational efficiency. That is, even when patients are created dynamically, some predetermined evolution information may be ready for use by the computer based examination system based on the potential of the possible evolution periods/health states. For example, if the target health state was moderate, the computer based examination system may have predetermined onset time of moderate, and therefore, know the time for mild, normal, severe, and the like. In effect, the white board database/object optionally includes a complete possible look at the future appearance, as well as the past characteristics for this particular patient at a particular health state.

The underlying goal of the computer based examination system is that the evolutionary process is generally the same as the patient generation process. Both processes are generally the same, just the generation process has more steps to generate the patient. In the evolutionary situation, the computer based examination system deals with multiple possible health state successors in different parallel networks. The zero state, or state where the examination begins, generally has a primary health state like moderate arthritis, possibly a flare state such as an acute swelling in the knee, and comorbid states such as overweight.

To generate the patient history, the computer process take the moderate arthritis, the flared up knee, and the overweight condition and looks backwards in time to determine the most recent precursor state. For example, the precursor of the moderate arthritis could be mild, the precursors of the flare could be baseline or normal, and the precursor for the overweight condition could be normal weight. The computer process sets the patient's current age, for example, as age 50, and now moves backward in time.

For example, for a 50 year old person with moderate arthritis, it is likely that the arthritis began 5-10 years ago. With respect to the flared knee, it is likely that this condition began within the last couple of days. For the overweight condition, it is likely that the 50 year old person began this condition 10-15 years ago. Therefore, there is a 5-10 year interval (arthritis), a 3 day interval (flared knee), and a 10-15 year interval (overweight). The computer process moves backward in time to that last change that should have occurred. In this situation, the first precursor health state is the flared knee which occurred 3 days ago. The clock then gets reset, and the next earliest precursor health state is determined. The whiteboard generally throws away all the previous information that was used to generate the later precursor health state, and recalculates the next earliest precursor health state until all precursor health states are generated to the normal condition for all conditions/diseases.

Switching to the forward version, the patient evolution process, the computer process looks forward in time instead of backwards in time. Therefore, considering the above example, there may be a change in 3 days (knee flare), another change in 5-10 years (arthritis), and another change in 10-15 years (overweight). The next change that will occur will be in 3 days. That is the evolutionary process which, similar to the patient history generation process, recalculates onset times for each subsequent health state. Thus, the main difference between the history generation process and the patient evolution process is the data being applied to each process.

The computer based examination system may also be used to determine whether specific physicians are practicing cost effective medicine for use by, for example, insurance companies. The system can provide objective criteria for treating patients by defining episodes of care for isolated problems. For example, the computer system can indicate approximately the amount of money to spend on a patient with a heart attack with no other concurrent problems, for an asthmatic patient per year, and the like. The computer based examination system and process provides a "flight simulator" where the physician can practice specific preferred forms of treatment, as appropriate. For example, if the patient has a heart attack, the examinee/physician should generally prescribe aspirin for long term usage, but many do not. Thus, the computer based examination system may also be used as a training system so that the examinees rehearse a desirable behavior such as prescribing aspirin after heart attacks. The computer based examination system can therefore also be used to increase desirable behavior when the physician interacts with a real patient.

Consequently, if a particular physician or group of physicians are determined to be expensive for an insurance company or health care group, and the computer based system shows that the physicians are likely to provide appropriate care, then it is possible that this physician or group of physicians have a particularly expensive patient population, and should therefore not be faulted. Further, the computer based examination system may also be adapted to receive the specific data collected by the physician and interventions associated therewith, to further verify that the practice is delivering the appropriate services. Thus, the computer based examination system, may be used to determine whether a particular practice is delivering services within predetermined guidelines.

Figure 15:
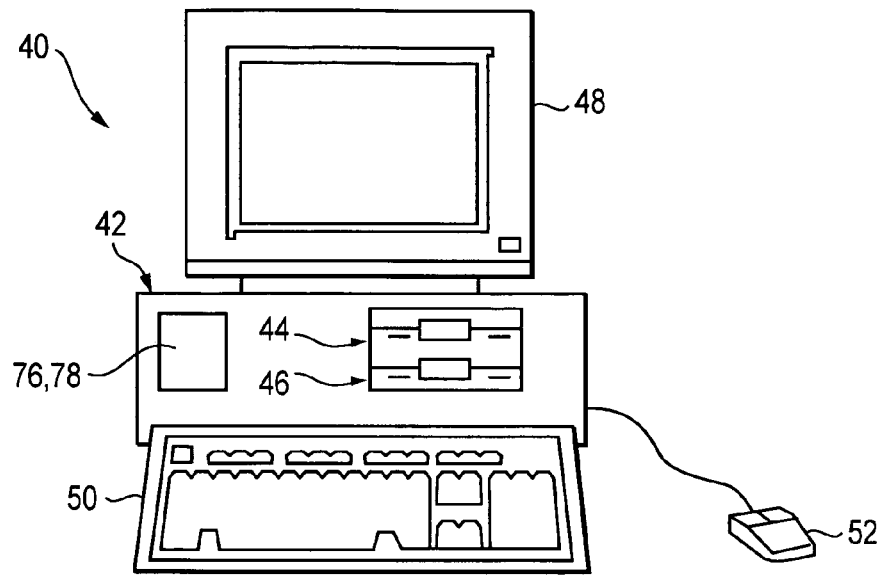
FIG. 15 is an illustration of a main central processing unit for implementing the computer processing in accordance with a computer implemented embodiment of the present invention.

FIG. 15 is an illustration of a main central processing unit for implementing the computer processing in accordance with a computer implemented embodiment of the present invention. The procedures described above may be presented in terms of program procedures executed on, for example, a computer or network of computers.

Viewed externally in FIG. 15, a computer system designated by reference numeral 40 has a central processing unit 42 having disk drives 44 and 46. Disk drive indications 44 and 46 are merely symbolic of a number of disk drives which might be accommodated by the computer system. Typically these would include a floppy disk drive such as 44, a hard disk drive (not shown externally) and a CD ROM indicated by slot 46. The number and type of drives varies, typically with different computer configurations. Disk drives 44 and 46 are in fact optional, and for space considerations, may easily be omitted from the computer system used in conjunction with the process/apparatus described herein.

The computer also has an optional display 48 upon which information is displayed. In some situations, a keyboard 50 and a mouse 52 may be provided as input devices to interface with the central processing unit 42. Then again, for enhanced portability, the keyboard 50 may be either a limited function keyboard or omitted in its entirety. In addition, mouse 52 may be a touch pad control device, or a track ball device, or even omitted in its entirety as well. In addition, the computer system also optionally includes at least one infrared transmitter 76 and/or infrared receiver 78 for either transmitting and/or receiving infrared signals, as described below.

Figure 16:
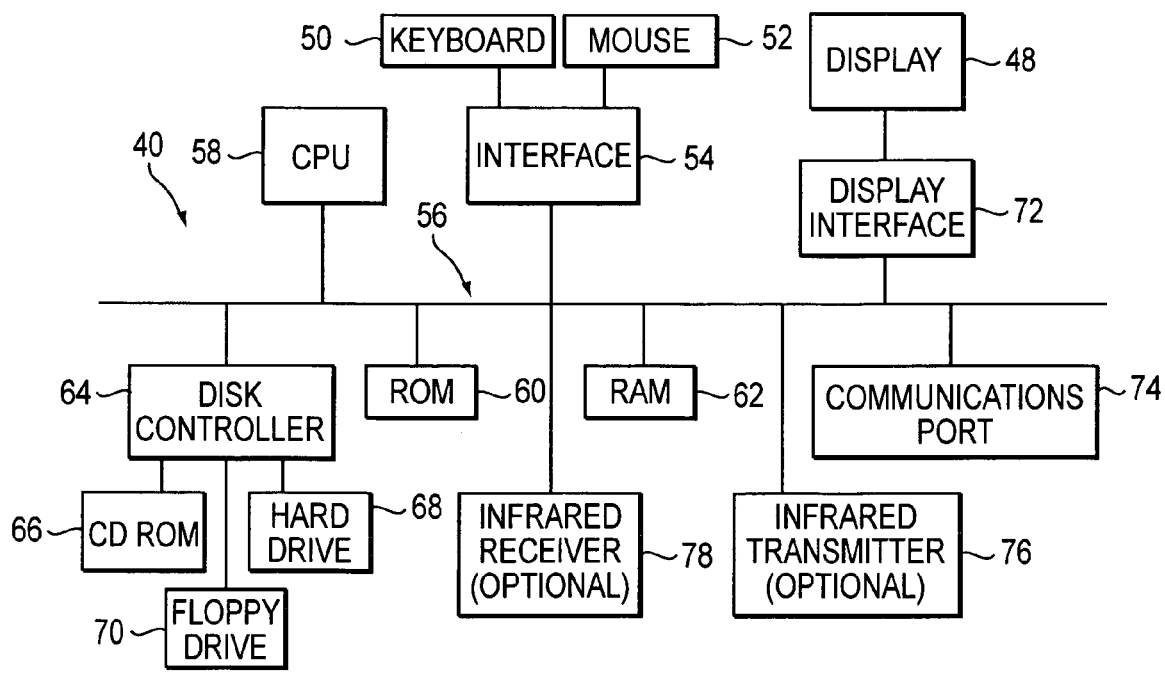
FIG. 16 illustrates a block diagram of the internal hardware of the computer of FIG. 15.

FIG. 16 illustrates a block diagram of the internal hardware of the computer of FIG. 15. A bus 56 serves as the main information highway interconnecting the other components of the computer. CPU 58 is the central processing unit of the system, performing calculations and logic operations required to execute a program. Read only memory (ROM) 60 and random access memory (RAM) 62 constitute the main memory of the computer. Disk controller 64 interfaces one or more disk drives to the system bus 56. These disk drives may be floppy disk drives such as 70, or CD ROM or DVD (digital video disks) drive such as 66, or internal or external hard drives 68. As indicated previously, these various disk drives and disk controllers are optional devices.

A display interface 72 interfaces display 48 and permits information from the bus 56 to be displayed on the display 48. Again as indicated, display 48 is also an optional accessory. For example, display 48 could be substituted or omitted. Communication with external devices, for example, the components of the apparatus described herein, occurs utilizing communication port 74. For example, optical fibers and/or electrical cables and/or conductors and/or optical communication (e.g., infrared, and the like) and/or wireless communication (e.g., radio frequency (RF), and the like) can be used as the transport medium between the external devices and communication port 74.

In addition to the standard components of the computer, the computer also optionally includes at least one of infrared transmitter 76 or infrared receiver 78. Infrared transmitter 76 is utilized when the computer system is used in conjunction with one or more of the processing components/stations that transmits/receives data via infrared signal transmission.

Figure 17:
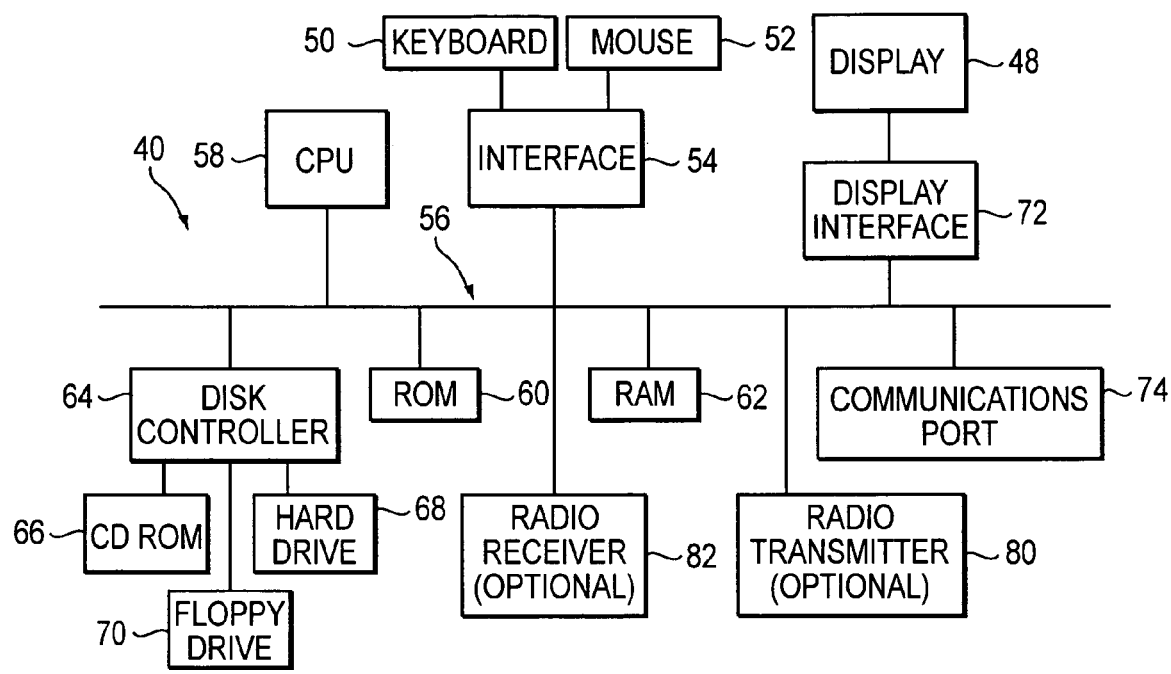
FIG. 17 is a block diagram of the internal hardware of the computer of FIG. 16 in accordance with a second embodiment.

FIG. 17 is a block diagram of the internal hardware of the computer of FIG. 15 in accordance with a second embodiment. In FIG. 17, instead of utilizing an infrared transmitter or infrared receiver, the computer system uses at least one of a low power radio transmitter 80 and/or a low power radio receiver 82. The low power radio transmitter 80 transmits the signal for reception by components of the process, and receives signals from the components via the low power radio receiver 82. The low power radio transmitter and/or receiver 80, 82 are standard devices in industry.

Figure 18:
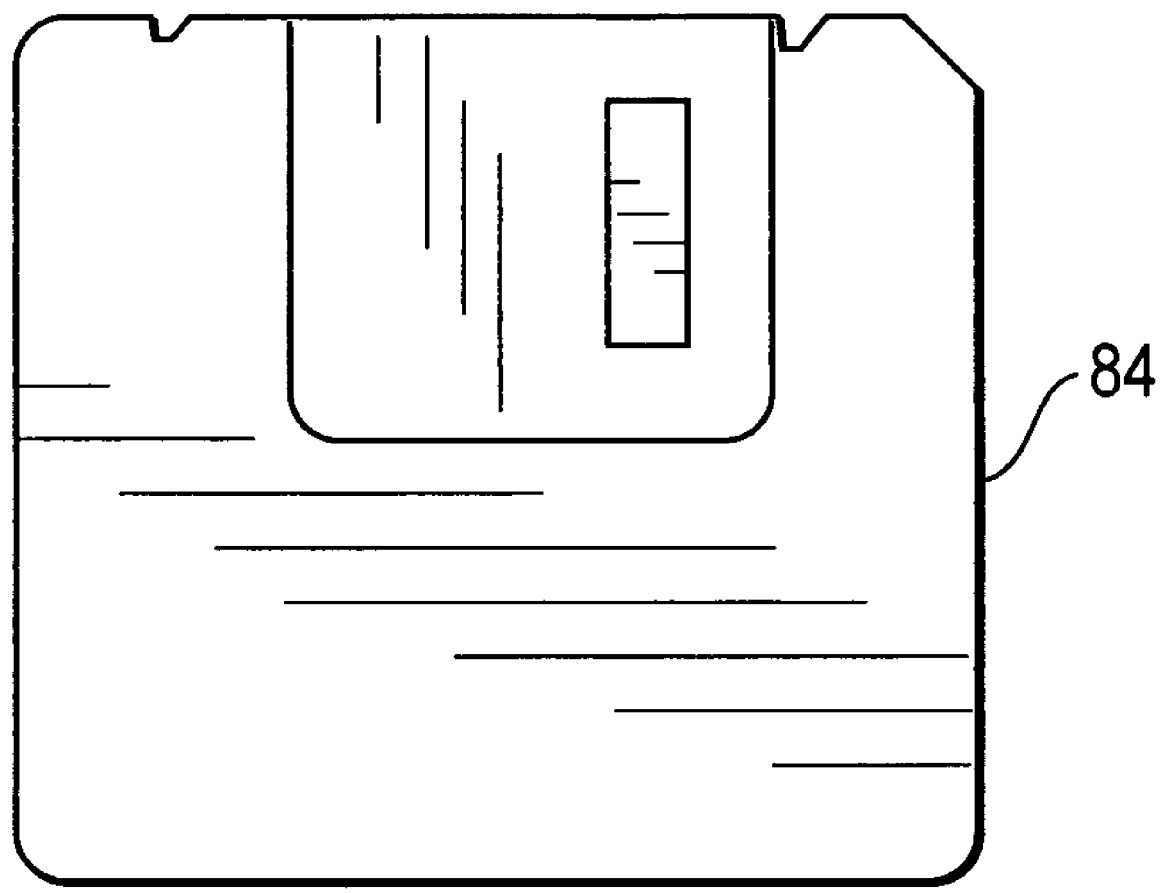
FIG. 18 is an illustration of an exemplary memory medium which can be used with disk drives illustrated in FIGS. 15-17.

FIG. 18 is an illustration of an exemplary memory medium which can be used with disk drives illustrated in FIGS. 15-17. Typically, memory media such as floppy disks, or a CD ROM, or a digital video disk will contain, for example, a multi-byte locale for a single byte language and the program information for controlling the computer to enable the computer to perform the functions described herein. Alternatively, ROM 60 and/or RAM 62' illustrated in FIGS. 16-17 can also be used to store the program information that is used to instruct the central processing unit 58 to perform the operations associated with the process.

Although processing system 40 is illustrated having a single processor, a single hard disk drive and a single local memory, processing system 40 may suitably be equipped with any multitude or combination of processors or storage devices. Processing system 40 may, in point of fact, be replaced by, or combined with, any suitable processing system operative in accordance with the principles of the present invention, including sophisticated calculators, and hand-held, laptop/notebook, mini, mainframe and super computers, as well as processing system network combinations of the same.

Conventional processing system architecture is more fully discussed in *Computer Organization and Architecture*, by William Stallings, MacMillam Publishing Co. (3rd ed. 1993); conventional processing system network design is more fully discussed in *Data Network Design*, by Darren L. Spohn, McGraw-Hill, Inc. (1993), and conventional data communications is more fully discussed in *Data Communications Principles*, by R. D. Gitlin, J. F. Hayes and S. B. Weinstain, Plenum Press (1992) and in *The Irwin Handbook of Telecommunications*, by James Harry Green, Irwin Professional Publishing (2nd ed. 1992). Each of the foregoing publications is incorporated herein by reference.

Alternatively, the hardware configuration may be arranged according to the multiple instruction multiple data (MIMD) multiprocessor format for additional computing efficiency. The details of this form of computer architecture are disclosed in greater detail in, for example, U.S. Pat. No. 5,163,131; Boxer, A., Where Buses Cannot Go, IEEE Spectrum, February 1995, pp. 41-45; and Barroso, L. A. et al., RPM: A Rapid Prototyping Engine for Multiprocessor Systems, IEEE Computer February 1995, pp. 26-34, all of which are incorporated herein by reference.

In alternate preferred embodiments, the above-identified processor, and in particular microprocessing circuit 58, may be replaced by or combined with any other suitable processing circuits, including programmable logic devices, such as PALs (programmable array logic) and PLAs (programmable logic arrays). DSPs (digital signal processors), FPGAs (field programmable gate arrays), ASICs (application specific integrated circuits), VLSIs (very large scale integrated circuits) or the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

For example, while the above discussion has separated the various functions into separate functionality, the functions may be combined, physically and/or logically, and various functions may be combined together. While combining various functions may make implementation details more cumbersome, nevertheless, the functions described herein may still be accomplished to advantageously provide some or all of the benefits of the invention described herein.

As an additional example, the foregoing discussion focused exclusively on medical applications of the current invention. Advantageously, the invention applies equally well to creating simulations of other complex systems, particularly complex systems in which an empiric description is easier to obtain than a comprehensive mathematical description. The concepts in the invention correspond to generic concepts that apply to complex systems in general. The labels in the current invention and the generic concept are listed in the table below.

The Population (or Person or Simulated Patient) concept represents any complex system. Consider a nuclear power plant. All breeder reactors form a population of breeder reactors, and each individual breeder reactor is an independent complex system within that population. The Record concept again reflects the knowledge of the system held by either people or computers. The breeder reactor may have its own Record of itself stored in a computer that supervises its operations. The public media and the Department of Energy will maintain other Records regarding the plant. Any of these records may contain inaccuracies.

The Health State concept corresponds to a generic System State. As with Health States, the System States often apply to specific parts of the plant. The Body Site concept corresponds to a generic Physical Component, such as the plant (like the body), the core (like the heart), and pipes (like the throat, blood vessels, or urethra). Each System State will apply to some of these components. For instance, it may be reasonable to describe the integrity of any pipe by naming its System State from a group of Pipe leak states. Obviously, one pipe may be leaking or ruptured while another pipe is intact, exactly as we have found with Health States occurring at Body Parts. A System State might include an error in a supervising computer's code, leading the complex system to respond inappropriately in some situation. This roughly corresponds to mental illness manifested by maladaptive behavior.

The Lead to relation again connects System States into parallel networks. Lead to relations again contain Modifiers which describe events that make transitions between System States more or less rapid. For instance, an earthquake might cause a fatigued pipe to twist, leak, and finally rupture, just as a sports injury can cause an ankle tendon to stretch, tear, and finally rupture.

Findings again represent observable facts about the Complex System, such as the temperature of a reactor's core, the water level of the core, or the flow rate of water through a pipe. System States will be defined primarily by the Specific Findings present. The exact Findings required will be provided by a generation method, such as a Bayesian network that reproduces experts logic about the clusters of Findings required to classify a Physical Component of a Complex System as existing in a particular System State. The simulation program asserts that the System State required for the simulation is present, then solves for all unknown nodes in this Bayesian network.

Courses of action again represent activities by humans, another external system, or the system itself. Generally, these will be efforts to restore or maintain equilibrium of the system, or to intentionally prepare the systems for a change of State. For instance, preparing the breeder reactor for a scheduled shutdown and maintenance is a course of action similar to preparing a patient for surgery. Agents again represent inputs to the system that influence its Findings or progression, such as cooling rods, water, fuel, or repairs to computer code.

Thus, we believe that the current invention has broad applicability beyond the domain of medical simulations. It is especially likely to be useful when the behavior of a system is so complex that an understanding of the system defies mathematical description. For instance, this invention is not well suited to simulating the flight of an airplane, which is fully described by physical laws. However, it might be excellent for simulating maintenance of the airplane, which is likely to reflect obscure design decisions and even unknown, but empirically observed, interactions between design decisions.

| Label in this invention | Generic concept | Nuclear power plant example |
|---|---|---|
| Population Record | Complex system Record | Nuclear power plant Press releases, DOE documentation |
| Health State | System State | Overheated core, Leaking pipe |
| Body site | Physical comp. | Plant, Core, Pipe |
| Lead To | Lead to | Intact pipe leads to Leaking pipe |
| Modifier | Modifier | Bayesian network describing how age and Earthquake modify the pipe lead to |
| Finding | Finding | Core temperature, Water level |
| Gener. method | Generation method | Bayesian network describing an intact nuclear plant |
| Course of Act. | Course of Action | Manual shutdown, automated shutdown |
| Agent | Agent | Carbon rod, Water, Uranium, Earthquake |

The Empiric Simulation Program

The American Board of Family Practice (ABFP) is developing a computer-based recertification process based on an Empiric Simulation Program (ESP) that produces new cases from an editable knowledge base. This approach could yield practically endless numbers of cases at an affordable cost per case, while maintaining a high level of security. To maintain an affordable cost per case, it is mandatory that the ESP not embed medical knowledge in code, that the ESP allows some stochastic variation between cases, and that large chunks of the knowledge base are reusable. However, to identify acceptable performance, the system must provide means to compare a candidate's actions with those deemed appropriate by a relevant group of peers. This requires that the knowledge base store conditional logic.

Medical diagnosis and management is replete with conditional and probabilistic logic that defies simple models or deterministic description. As an example, patents suffering from osteoarthritis (OA) may experience the disease starting early in life, following joint trauma or other articular diseases, or late in life, especially following years of excessive weight bearing. The rate of progression of the disease has not been described, but it can be slowed by weight loss. Knee joint destruction may occur in the lateral compartment, but more frequently occurs in the medial compartment. Joint pain correlates poorly with objective findings. Patients who seek care because of joint pain should usually be treated with acetaminophen first. If acetaminophen is inadequate, non-steroidal anti-inflammatory drugs can be added or substituted. However, some of these drugs might accelerate joint destruction. Furthermore, the entire class of drugs is more hazardous in the presence of gastric ulcers, renal disease, hypertension, bleeding disorders, and asthma. The gastric ulcer hazard can be mitigated by either misoprostel or omeprazole, but probably not by H-2 blockers or sucralfate. Intra-articular steroid injections are useful for acute exacerbations or if other therapies fail. Knee joint replacement is an option, but replacement joints last about 10 years. Finally, the advent of new treatment options, such as COX-2 inhibitors or injectable hyalin, could completely alter recommended care of OA almost overnight.

Probabilistic and/or conditional logic thus pervades every aspect of OA, including incidence and prevalence, disease progression, physical findings, symptoms, recommenced management, and response to treatment. Nevertheless, the diagnosis and management of OA is relatively simple from a clinicians perspective. Many common problems are considerably more complex. Consequently, we expect many medical problem domains to contain at least as much conditional and probabilistic knowledge as the OA domain.

Early Scripting Efforts

The need for scripts was therefore recognized by Applicants at an early stage of development. We had simultaneously begun to divide medical knowledge into parallel networks comprises of health states (stages of a well described disease process) linked by "leads to" relations (describing the rate of progression from state to stage.) Health states were typically defined by asserting findings such as "normal height" or "normal hematocrit," but the ESP would eventually have to provide an actual height and hematocrit. The range of normal values varies with age, sex and race. We also distinguished a concept of activities that reveal data about a simulation (e.g. questions and lab tests), and a concept of management criteria. Thus, we had five distinct concepts that seemed to hold the vast majority of conditional logic: Health state definitions, Lead to descriptions, Specific Finding definitions, Revealing queries, and Plans for care. Scripts would be needed for each of these.

Fortunately, we determined these scripts could be written to be independent of any particular simulation, and therefore could be reusable. For instance, a health state definition could be completely independent of the process that lead to the health state. Whether OA developed quickly because of overt trauma or slowly because of obesity, the same script would describe associated findings. Similarly, a script that predicted the rate of progression could indicate that greater weight produces faster progression, and that direct trauma produces very fast progression.

Our first scripting approach was inspired by the scripting language of The Medical Record (TMR). TMR used scripts to inspect medical records and alert physicians to actions they might take. Those scripts typically consisted of lines containing a conditional statement, an action to take if the statement were true, and an action to take if the statement were false. The lines were executed in sequence, unless a GOTO statement sent the program to a specified line. Logical loops, such as an instruction to vaccinate for tetanus every ten years, could be implemented using GOTO statements. In our implementation, we developed an interpreted language with a few standard queries to extract data from the simulation, commands to write information from the knowledge base to the simulation, and operators to manipulate information within the script.

This scripting language was rapidly implemented for the first prototype of the simulator, demonstrated at the American Board of Medical Specialties meeting on computer-based testing in Chicago, Mar. 21-22, 1996. It was easily extensible, but very difficult to write and almost impossible to proofread or explain to physicians. In addition, the process of parsing and interpreting the script was an important performance bottleneck. In implementation, the scripts we created had very consistent logical flows related to their tasks. The scripts were monotonously similar.

Sets of Conditions

The consistent scripting requirements allowed us to replace interpreted data extracting queries and data writing commands with new classes of objects called Conditions. Condition subclasses currently include Performance, describing an examinee's previous evaluations; FindingValue, for acquiring continuous values such as height or hematocrit; and Relational, for inspecting and establishing relationships between patients and other entities. For instance, a relational condition may indicate that a patient Has a Health State, was Exposed to a disease causing Agent, or Exhibits a Specific Finding.

A Condition used as a query may return either a Boolean or continuous value. Relational and Performance Conditions typically yield Boolean values, in effect answering questions such as, "Has the patient had knee OA for longer than 5 years?" FindingValue Conditions typically yield continuous values, in effect answering questions such as, "What is the patient's height now?" A Condition used as a command is a template for writing new information to the simulation. These typically establish some concept that persists until succeeded by another concept. For instance, a Condition would establish that a patient "Has glucose intolerance starting now and lasting indefinitely." This Condition would persist until succeeded by the Condition that the patient "Has type II diabetes mellitus."

We also designed a class called Sets to replace some of the probabilistic information previously embedded in scripts. A Set contains several Conditions, and indicates how many ought to be present for the Set to be logically true. Sets support subset concepts such as exactly N Conditions(N>O), between N and M Conditions(M>N≧0), and at least N Conditions. Thus, Sets allow a succinct means of asking whether a simulated patient has any number of arthritic diseases, or asking whether the patient has been prescribed exactly one non-steroidal anti-inflammatory drug, or stating that the patient must have at least 2 and possibly four cartilaginous abnormalities.

Bayesian Networks

We implemented Conditions and Sets in a new model in 1996, but still needed a mechanism for organizing these concepts, and in particular for creating dependencies. We could use Sets to define the state of a node in a graph. We briefly experimented with using tree structures, in which a tree node could have multiple states. Each state would be defined by a Set of Conditions, linked to other arbitrary information (such as multimedia), assigned a probability, and point to another tree node. To use a tree, the ESP would inspect the root node and determine whether any of the states were already established or impossible in the simulation. It would stochastically select one of the remaining possible states, then follow the corresponding branch of the tree, It would repeat this process until it reached a terminal node. The terminal node and the path to it would provide the information the ESP needs to create a plausible patient, critique a physician's management strategy, or produce a laboratory report conditioned on the nuances of a simulation. The ESP would perform these tasks in time proportional to the greatest depth of the tree, or better.

Although the tree approach was technically feasible, many practical problems soon became evident. The first problem was the frequent need to nearly duplicate part of a branch with slight changes. For instance, the root node in a tree that implements OA stages might inspect the simulation for the current stage of OA, then produce findings conditioned on that result. Each of its branches will describe joint space narrowing in a probabilistic way, with some overlap. Mobility and pain nodes might depend on both the stage of OA and the joint space narrowing. Thus the tree has very redundant looking branches with only slight changes in probabilities. These trees are therefore hard to inspect.

Although Bayes nets are NP hard to solve precisely, they have several well known advantages. First, most of our node and state concepts could be reused immediately. Second, a Bayes net will almost never represent the same concept in two separate nodes; conditional probability tables replace the separate branches required in the tree structure. Third, other groups are actively developing analytic techniques that allow very rapid approximation of Bayes net solutions. Fourth, companies such as Norsys Software Corp. (www.norsys.com) are developing affordable software packages such a Neticarm™ and can provide a well documented, correctly functioning application programming interface to developers. Finally, Bayes nets can compactly represent very complicated information, and allow knowledge editors, supervisors, and external reviewers to interactively explore a model by setting the states of nodes and inspecting updated probabilities.

Methods

The knowledge base was revised to accommodate Bayesian networks, for example, represented as Neticarm™ files, node states defined with Sets of Conditions, and additional network and node details required by the ESP. A production quality knowledge acquisition effort was initiated for OA and diabetes mellitus, and other diseases that predispose to or complicate these diseases. We began additional knowledge acquisition efforts in otitis media, depression, hypothyroidism, abnormal Pap smear management, and hypothyroidism.

The use of Bayesian networks as a scripting language has been partially tested by implementation of an object oriented database which was populated with data about OA and obesity. Expressiveness was tested in the other domains. We were actively programming an ESP that will rely almost entirely on Bayes nets and Sets of Conditions to describe conditional and probabilistic information in family medicine, and preparing to enter hypothyroidism data in an object oriented database.

Results

Current Structure

Figure 19:
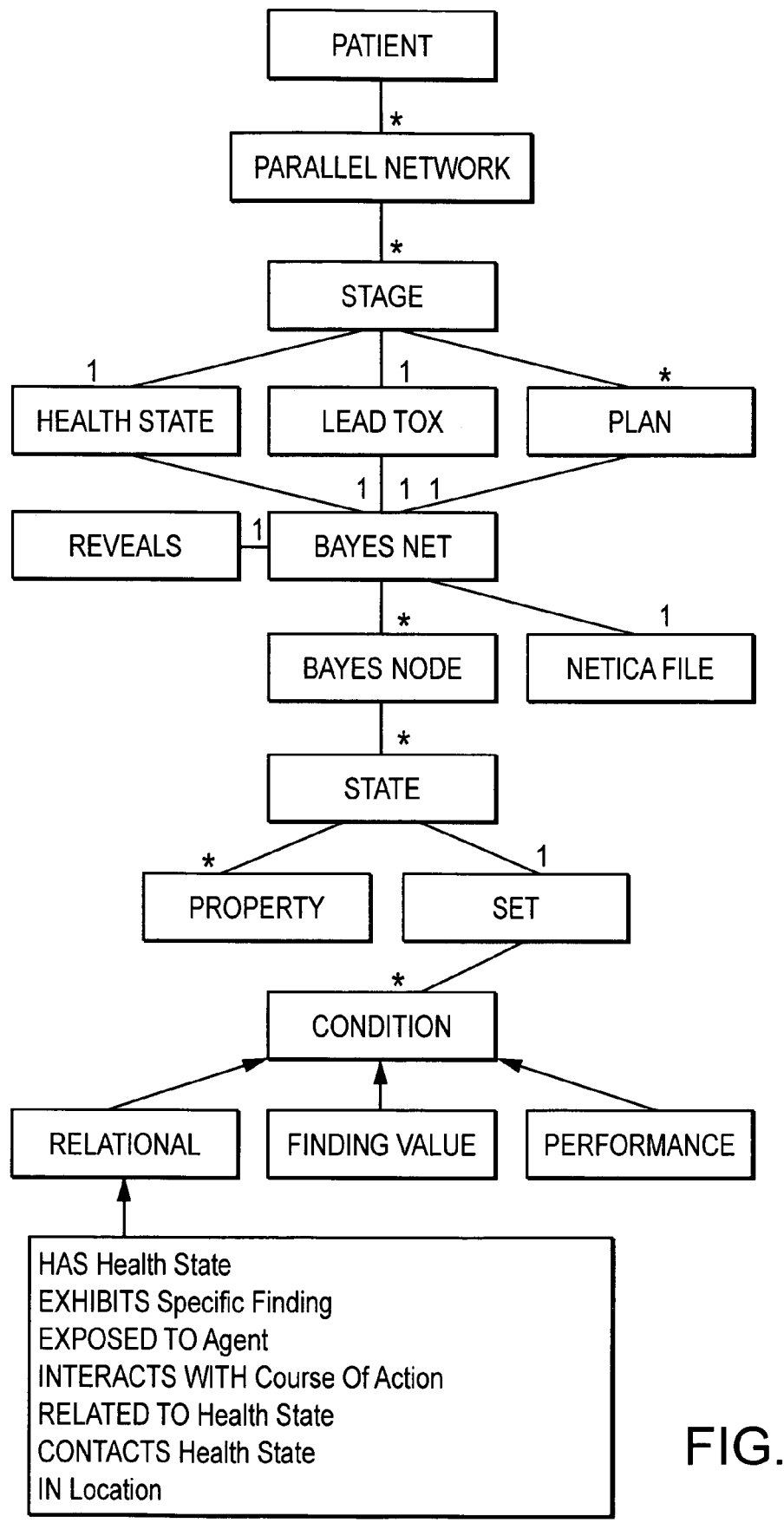
FIG. 19 is an illustration of a relational diagram of the Bayes networks and other supporting structures.

FIG. 19 illustrates classes in the relevant portion of the final knowledge base structure. Lines indicate that one class is associated with another class. An asterisk, "*," indicates a one to many relationship, while a number indicates an exact number of associations. For instance, a Health State is associated with 3 Bayes nets, which provide incidence, prevalence, and disease descriptions. Arrows indicates ISA relationships. The lightly shaded classes require a means of expressing probabilistic and conditional information, once provided by a scripting language.

The Bayes Net, Bayes Node, and State structures are replicated in part in the Netica™ file. This design requires that we maintain very strict name consistency between the knowledge base and Netica™ file. The Property may contain a time function (e.g., incidence or prevalence as a function of age), a multimedia reference (e.g., a sound to play), simple text, or a function of properties of other nodes. The seven most important Relational Conditions are listed.

Expressive Verification

The knowledge acquisition effort has used these data structures to record all of the conditional dependencies found to date. Space prohibits reproduction of Bayesian nets in this specification, but the following fragments illustrate the use of Bayes nets and supporting structures in place of scripts.

Figure 20:
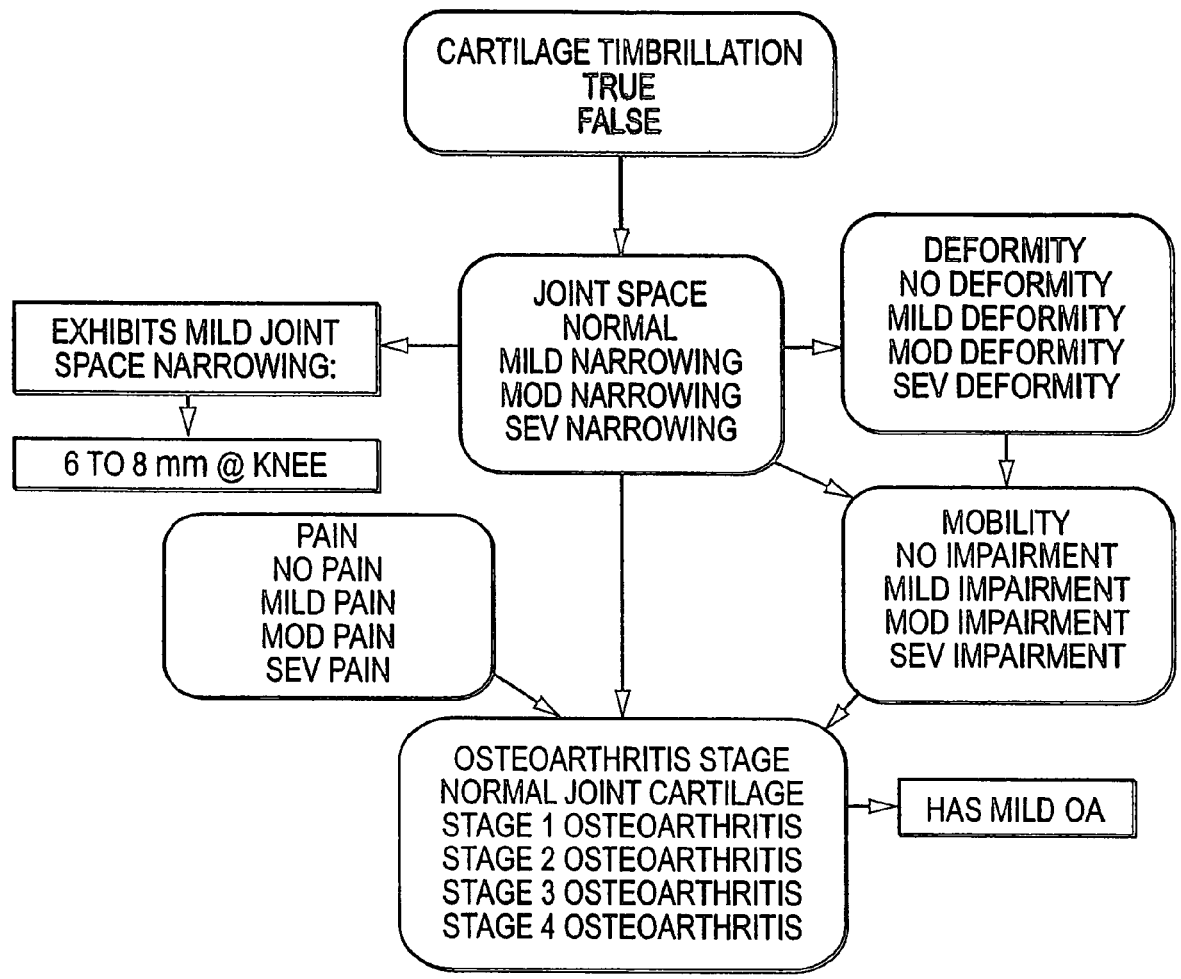
FIG. 20 is an illustration of an example using a Bayes network to describe osteoarthritis.

FIG. 20 illustrates a simplified OA generating Bayes net. The network was built as a roughly physiologic model of the development of OA, assuming that cartilaginous deformities and destruction cause joint space narrowing, accompanied by sclerosis and subchondral cyst formation (not shown), and leading to gross deformities and loss of mobility. Pain is a variable feature, but probably must be present in a test case (otherwise, how would the doctor's attention be drawn to the joint?). The mild narrowing state of the joint space node is defined by a Set containing one Condition, EXHIBITS the Specific Finding, mild joint space narrowing, which is itself defined as a joint space of 4 to 6 mm for the knee. The stage I state of the osteoarthritis stage node is similarly defined by a Set containing one Condition, HAS mild OA. The conditional probability tables for this node are arranged so that certain combinations of joint space narrowing and deformity define mild OA. Other combinations may define other stages, or be declared impossible (e.g. severe deformity without joint space narrowing might be impossible in this context).

Two interesting benefits of this approach are first, that we can use a single Bayes net to describe all five stages of OA, and second, through the logical magic of Bayes theorem, we can now invert a Bayes net built from a perspective of classifying stages of OA, and use it to generate descriptions of OA. We assert that the patient HAS any stage of OA, update probabilities throughout the network, and start stochastically assigning states to indeterminate nodes. With each assignment, we write new information to the simulation, e.g., that the patient EXHIBITS mild joint space narrowing. We can test the Bayes net by experimenting with it from both perspectives, e.g., beginning with an assumption of cartilage damage to see what stage of OA results, or beginning with OA to see what other findings result.

Bayes nets supporting Leads to structures are conceptually very similar to Health State generating Bayes nets, with two important differences. First, the Conditions usually describe task factors for slower or more rapid progression, rather than features of a disease. For instance, an OA Lead To is likely to ask whether the patient HAS Obesity, or to assert that the patient is EXPOSED to some remedy.

Second, the goal of the Lead to structure is to produce a rate of progression, which is not specified anywhere else in the simulation. (In contrast, the Health State generator has a goal of creating a description consistent with an asserted disease).

Figure 21:
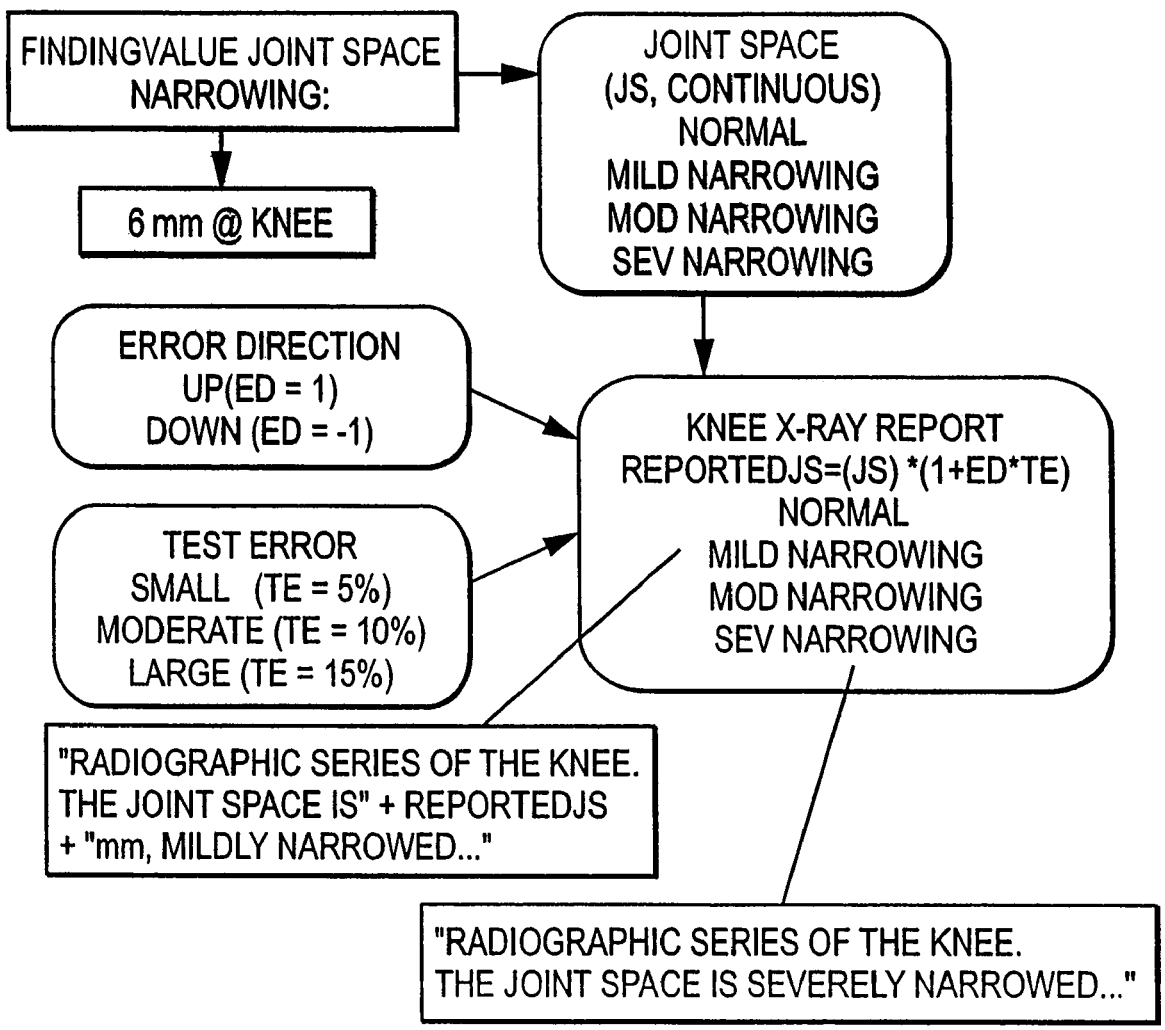
FIG. 21 is an illustration of an example using a Bayes network to generate a report when a user submits a medical finding query.

FIG. 21 illustrates a Bayes net that could produce a report when an examinee requests a Revealing x-ray test. The only simulation data used in this report is the joint space, a value indirectly modified by the Bayes net in FIG. 20. Now we have a continuous Bayes node acquiring its value from a Condition that extracts the current joint space from the simulation. Note that there are no requests to determine whether any Specific Findings or Health States are present. Revealing queries should therefore be reusable across simulations. Also, the accuracy of the test can be built into the Bayes net representing that test. Another test, such as a magnetic resonance image, could have different size errors.

Subjective queries are much more complex, but still possible to construct using the same approach. The primary complication is that subjective responses are uniquely elaborate in temporal detail, yielding statements such as, "the pain has been coming going for weeks, but now it is worse than ever."

Management Plan critiques are similar to Reveals, except that most of the Conditions inspect prescriptions and queries made by the examinee, and the resulting report is a critique of a physicians' strategy. Our experience to date confirms the expectation that Bayes nets support inferences about actions and plans.

Limitations

The current knowledge base design requires the additional validation of supporting a working simulator. We can not yet prove that the concepts presented here will work in the simulator we are programming. Our knowledge acquisition experience has uncovered one instance in which we thought that the data source for a continuous Bayes node (Hemoglobin AC levels) should be another Bayes network. This raised the specter of solving recursive (or accidentally cyclical) NP hard problems to produce a simulation or answer a question. We expect that wary knowledge editing can prevent such problems.

Bayesian networks, with appropriate supporting structures, are capable of representing important concepts in family medicine and seem likely to replace other scripting options in a simulation program that we hope will produce recertification tests in the future. We will soon demonstrate whether we are able to produce realistic simulations using this scripting language.

Computer-based testing holds promise as a technology that could add educational content to the testing process while yielding different, and perhaps more important, information about examinees than paper-based tests. Some computer-based tests use traditional multiple choice item formats. Other tests simulate patient care experiences. Some elegant simulation programs generate patient data from systems of equations, but most outpatient medical problems still require empiric description. Some programs embed the logic of the simulation in 2,3 code, although reuse and knowledge maintenance may be difficult.

The American Board of Family Practice (ABFP) is developing a computer-based recertification process based on an editable knowledge base. This empiric simulation project (ESP) could yield practically endless numbers of high quality cases at an affordable cost per case. Variability in case presentations should help the ABFP maintain a secure test. Conversely, modeling decisions which restrict the details of case histories may reduce security.

The ESP development team designed an entity-relationship model of medical concepts and algorithms to create patient simulations from the data model. These algorithms create patient histories and evolve patients during simulated medical care. The central concept in the history generation algorithm is that patients with some health states evolve to experience other health states.

The assumptions underlying early ESP algorithms and data models were similar to those of a Monte Carlo process. A simulated patient would have partially completed a path through a Monte Carlo network. A physician's management decisions would influence the remainder of the path. Nodes along this path represented the patient's overall health during a period of time, that is, all simultaneous medical problems are represented in a single Monte Carlo node. Arcs between nodes represent the patient's transitions between conglomerate health states. Other common decision modeling techniques, such as Markov processes and decision trees, employ similar models of health states.

The Department of Family Medicine at Duke University and the affiliated Cabarrus Family Medicine Program conducted knowledge acquisition experiments for a variety of problems common in family practice. These included alcohol abuse, ankle sprains, diabetes mellitus, hypertension, osteoporosis, otitis media, peptic ulcer disease, pregnancy, reactive airway disease, and smoking. These domains involve addictions and behavioral problems, acute illness; acute illness superimposed on chronic predisposing illness; and non-systemic illnesses. The ESP development team advised the domain experts, and simultaneously modeled osteoarthritis of the knee and normal health.

These experiments demonstrated many serious difficulties with the conceptual model. First, to obtain variable histories required modeling many nodes in a Monte Carlo simulation. In several domains a chronic progressive systemic illness (e.g., osteoporosis) combined with recurrent acute site-specific exacerbations or complications (e.g., fractures of various bones). The original model implied the need for a large number of conglomerate health states, for instance to define multiple paths from "Normal health" to "Ex-smoker with severe osteoporosis and healed second left hip fracture." The number of conglomerate health states can expand quickly, and data required to define these conglomerate health states (e.g., age specific incidence) is often speculative and redundant.

Second, identical information may be collected in several testing domains. For instance, highly redundant obesity descriptions would appear in tests of osteoarthritis, diabetes, and hypertension.

Third, relations between health problems are unclear. Conglomerate health states do not compartmentalize disease processes, obscuring whether domain experts consider hyperthyroidism or nicotine addiction as direct precursors of osteoporosis, or risk factors, or distracters.

Fourth, modeling one therapeutic complication adds many nodes and arcs. Therapeutic complications are typically new illnesses superimposed on any of several antecedent conglomerate health states. For instance, a patient in any of the osteoporosis nodes might develop uterine cancer while taking unopposed estrogen. The number of nodes required in the Monte Carlo model may double, with an equal number of new arcs. Historical distracters, such as randomly appearing colds or a history of appendicitis might require still more conglomerate states.

Finally, a computer-based test needs to specify the anatomy of disease, so that it can correctly present findings to the examinee. In some diseases the anatomy is erratic. A typical osteoarthritis patient will have joints afflicted to different degrees.

Thus, Monte Carlo modeling techniques have an appealing ability to generate multiple temporal sequences of events. However, the ABFP's need for finer anatomic detail, reusable information, and manageable knowledge acquisition and maintenance required some revision of the Monte Carlo approach.

Methods

The ESP model was revised to define Parallel Networks of Health States, while discarding conglomerate health states. A Parallel Network includes a sequence of distinguishable, mutually exclusive Health States. These typically reflect the medical literature's descriptions of stages of progression or severity of a disease. If the literature does not provide a staging definition for a disease, Health States can usually be defined as absent, mild, moderate, and severe.

A parallel health state network connects these health states with "Leads To" objects, e.g., mild disease leads to moderate disease. A Leads To object associates specific collections of risk factors and treatments with a fuzzy rate of progression from the preceding to succeeding Health States. The risk factors may be Health States from other Parallel Networks, activities (e.g., work, play, and habits), and family history. Treatments may be interventions prescribed by the examinee, or some simulated previous provider.

Separate collections of Leads To objects manage history generation and evolution. In history generation, the ESP creates a life history and context for the examinee's encounter with the simulated patient. The examiner may want an unremarkable story compatible with many simulated medical problems, or a story that is virtually pathognomonic. In evolution, an efficient test might routinely simulate rapid progression of disease or complications of the examinee's treatments, regardless of the likelihood of these events in practice.

Each Parallel Network defined in a simulation imposes its Health States on one or more anatomic sites, which evolve simultaneously. For instance, a rheumatoid arthritis simulation could name a single Parallel Network and all of the joints affected. An osteoarthritis simulation might use two copies of a knee osteoarthritis Parallel Network, applying one to each knee. Different presenting Health States at each knee and independent evolution of the knees would be typical of osteoarthritis. Systemic diseases involve the entire body of a simulated person.

Health States may recursively contain Parallel Networks representing more acute exacerbations of the parent Health State. For instance, moderate osteoarthritis may include a Parallel Network describing transitions between baseline and flare Health States. A simulated patient cycling between these Health States will display or recount episodes of worsening arthritis symptoms.

The algorithms for history generation and evolution were adapted from Monte Carlo techniques. A request for a simulation identifies the presenting Health State in each Parallel Network. Using incidence and prevalence information, the age, sex and race of the simulated patient are selected. The time of the next (or, in history generation, the preceding) event in each Parallel Network is predicted. In history generation, this may require assertions regarding the activities of the simulated patient. The temporally closest event from all of the Parallel Networks is instantiated. In history generation, the process of predicting the most recent preceding Health State change proceeds backward through time until no further transitions are defined by the Parallel Networks. In evolution, this process of predicting the next event continues until one of the events initiates another encounter with the physician.

The revised ESP model was tested by additional knowledge acquisition experiments, implementation of a Poet™ object oriented database and supporting algorithms, and generation of simulated osteoarthritis cases. The database was used to generate cases of osteoarthritis of the knee with obesity as a risk factor, and gastric ulcers induced by non-steroidal anti-inflammatory drugs prescribed without misoprostel.

Results

Knowledge Acquisition

Figure 22:
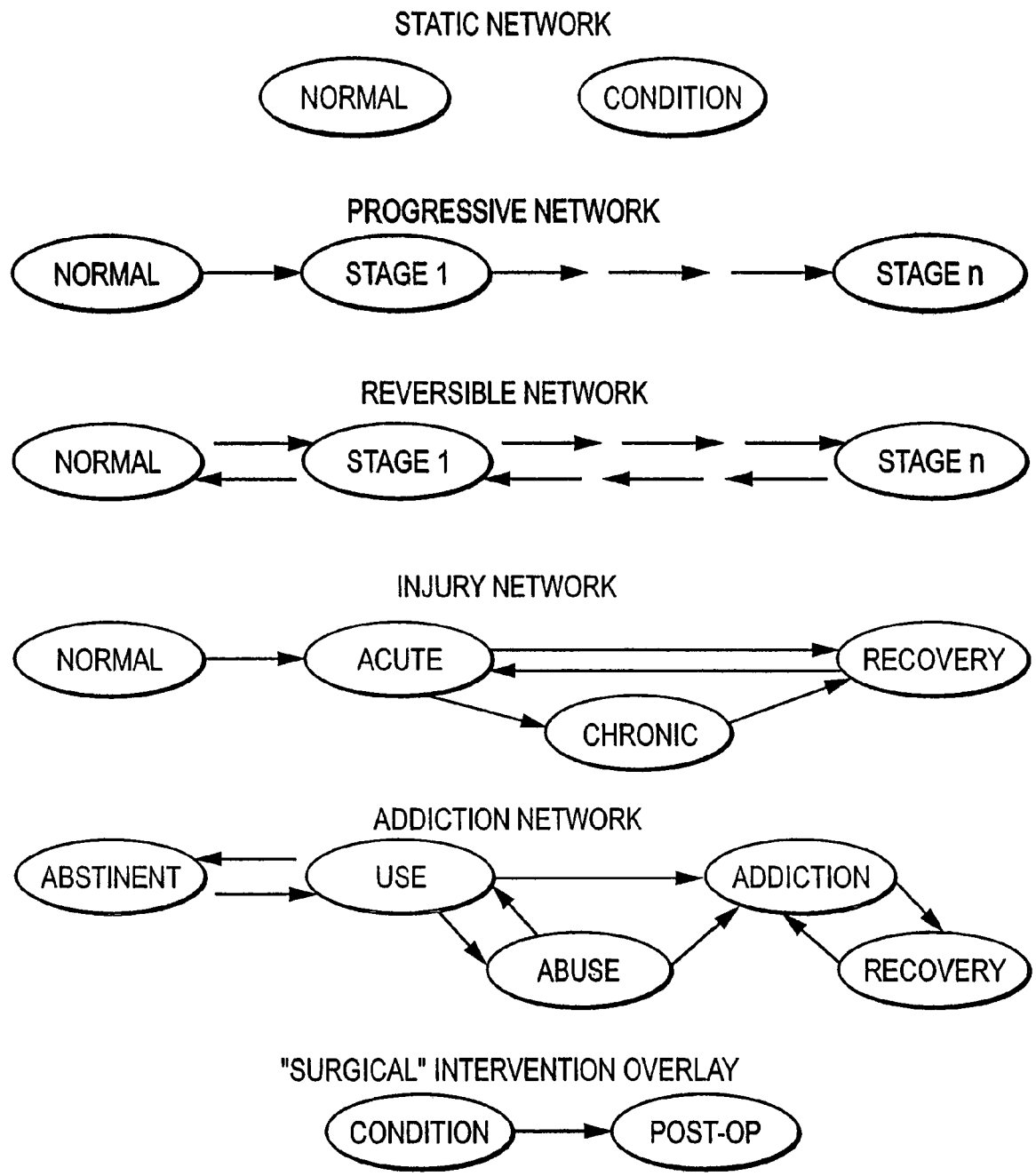
FIG. 22 is an illustration of examples of disease evolution described by parallel health state networks.
Figure 23:
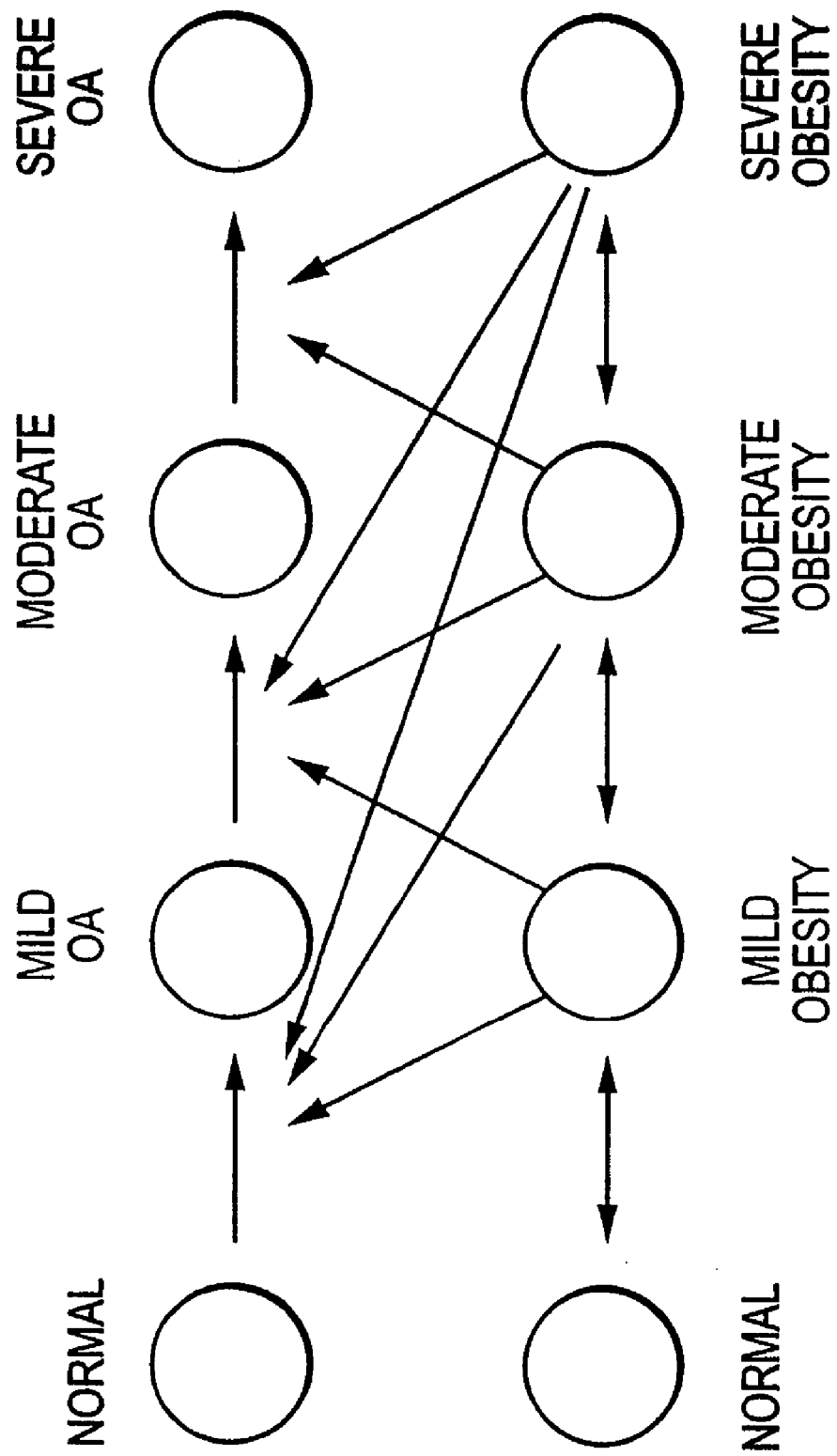
FIG. 23 is an illustration of an example of interactions between parallel health state networks.

Simple illustrations of their medical domains helped content experts understand the scope of their knowledge acquisition tasks. Initially intricate domain models were decomposed into much less threatening Parallel Networks. FIG. 22 illustrates common Parallel Network structures. The simplest network is a collection of one or more static states, typical of genetic (e.g., Downs syndrome) and some congenital conditions (e.g., anencephaly). The progressive network is a series of states with no cycles, typical of degenerative illnesses such as osteoarthritis. The reversible network illustrates chronic but reversible conditions, such as essential hypertension and weight disorders. In the injury network an acute insult evolves to either recovery or a chronic condition with a later recovery. Injury networks describe many infectious diseases and trauma. The addiction network illustrates that a person may abstain from, use, abuse, or become addicted to a substance. In the scheme shown here, a previously addicted person can only be addicted or recovering, but cannot return to abstinence, use or abuse. The surgical intervention overlay illustrates that new states can be added to the above networks using irreversible therapies such as radiation or surgery. Domain experts adapted these networks to their needs by eliminating unwanted nodes and arcs, or replacing nodes with another network.

Domain experts began with a primary Parallel Network to sketch the diseases defining their domain, such as stages of diabetes mellitus. Parallel Networks of comorbid conditions were identified in most domains, typically including risk factors for progression through the primary network, such as obesity. Most domains included one recursive layer of Parallel Networks representing exacerbations of Health States in the primary Parallel Network. Most domains also identified one or more Parallel Network representing complications of Health States in the primary network, such as retinopathy, or of treatment of primary Health States, such as gastric ulcers.

Experts were asked to estimate 1) how long a risk factor should exist before it could influence a transition between states in a primary network, 2) the time required for transitions in the primary network, given different combinations of risk factors, and 3) the number of passes an individual patient should be allowed to make through a cycle (e.g. from acute injury to recovery and back). Although these data were often non-existent in the literature, domain experts could comfortably estimate a range of values from clinical experience. Although the data to gather remained imposing in volume and dauntingly quantitative, Parallel Networks in the revised ESP model appeared to successfully guide segmentation of data into intellectually plausible sets.

Data Model and Algorithm Implementation

The osteoarthritis experiment continued with development of an object oriented database structured after the ESP model. The database was populated with information about four stages of osteoarthritis, three weight conditions, and 2 ulcer states.

The algorithms mentioned above were implemented, but without support for acute exacerbations or multiple Parallel Network copies afflicting different anatomic sites. Conditional probabilities were managed with a simple scripting language. The scripting language has since been replaced by Bayesian networks.

Instantiation of the model confirmed the expected difficulty in authoring a family of cases with the same underlying disease process, but different details in presentation. In particular, giving attention to conditional probabilities slows knowledge acquisition considerably. Memories of individual clinical cases were helpful in authoring a narrowly defined simulation, but much more attention was required to produce Health States generation methods and Leads To objects that were robust to changing assumptions about sex, race, and obesity. In spite of these difficulties, data entry in a data base founded on Parallel Networks was accomplished.

Experimental Verification

The prototype ESP simulator generated a series of patients for demonstration at the American Board of Medical Specialties meeting on computer-based testing in Chicago, Mar. 21-22, 1996. Approximately 30 patients were generated and stored over a four day period, including several during the meeting. Each patient generation required about 20 minutes. After generating a variety of male and female patients, data in the knowledge base were skewed to generate middle aged overweight white females. These patients were typically 55 to 65 years old and complained of recently worsening pain in one or both knees. Patients had been morbidly obese for 1 to 3 years prior to presentation, and had at least a 5 year history of mild arthritis in the affected knees.

Their health problems began with either obesity or mild osteoarthritis 10 to 30 years prior to presentation.

During the demonstration, most history and laboratory requests returned graphs of values over the simulated patient's lifetime, enabling viewers to see how variables such as weight, uric acid, or osteophyte numbers had changed since birth. These graphs demonstrated concurrent histories of worsening osteoarthritis and obesity.

Demonstration patients were managed interactively. Patients managed with high doses of nonsteroidal anti-inflammatory drugs without misoprostel would develop ulcers sometime during a 2 year follow up period. Weight loss was also possible. Optimal management of weight and prescription of strengthening exercises would slow the inexorable progression of knee osteoarthritis, but progression from moderate to severe knee arthritis would inevitably occur within 10 years.

Discussion

The simulations demonstrated that the prototype system could generate patients with plausible medical histories; appropriate symptoms, signs, and laboratory values; and could evolve patients over time. The separation of data controlling osteoarthritis, obesity, and ulcer histories and presentations suggests that these components would be reusable with modest modification, if any, in new disease domains. Substantially different osteoarthritis simulations could be produced by replacing a few history controlling Lead To objects.

Limitations

We are currently developing a simulator with acute exacerbations, past medical interventions, and use of multiple copies of one Parallel Network's data. The new model and algorithms replace simple scripts with Bayesian networks. Although the next generation simulator is not yet functional, no fatal conceptual difficulty is evident.

The knowledge acquisition problem for the ESP model remains daunting. One vexing problem is that the history generation algorithms require solutions to multiple temporal constraints. These constraints may not always have a solution, and it is not yet clear how to react if a history generating step fails, or how to guarantee temporal solutions while reusing data.

The Cartesian product of N parallel networks creates an N dimensional grid whose nodes represent conglomerate health states. This grid is a complex Monte Carlo model with many low probability paths that would never have been considered in an explicit Monte Carlo model. Conditional probabilities within Parallel Network's Leads To objects could provide a means of pruning the N-dimensional space. This mechanism may not work, as it places further burdens on knowledge acquisition and reusable object design.

These limitations must be considered in context. In the absence of mathematical models of the diseases of interest, the ABFP requirements for secure tests, realistic temporal and clinical features, and defensible credentialing decisions, complex data is an inevitable feature of a computerized problem generation process.

Parallel Networks facilitate some aspects of knowledge acquisition for a patient simulation knowledge base, and appropriate algorithms support generation of patients. The data required are relatively reusable, in contrast to data explicitly describing global health. Further experimentation is required to demonstrate that this approach remains tractable with more complex scenarios. Parallel Networks may have application in other endeavors that traditionally describe global health, such as decision analysis.

Background Information for Knowledge Development

Medical certifying organizations have traditionally relied upon paper and pencil cognitive examinations to measure certification candidates' suitability for board certification. Traditional formats such as multiple choice questions have well-defined operating characteristics and reliability for examining cognitive knowledge capabilities. They provide, however, only primitive ability to assess a candidate's problem-solving capabilities. Additionally, traditional testing strategies rely upon a continuous process of item development; once used, the items in an examination must be replaced with new questions in order to preserve security of the certification process. Each examination represents a product that the certifying organization can use only once. The presently used medical certification process thus suffers from two weaknesses: 1) test development requires re-generating an examination with new material on a recurring (usually annual) basis; 2) although multiple choice questions demonstrate reliable performance in measuring cognitive knowledge, this format doesn't measure adequately problem-solving capabilities.

Several organizations have experimented with computer-delivery of clinical content and evaluation. In the late 60's and 70's, the Ohio State University developed a self-directed Independent Study Program that utilized a "Tutorial Evaluation System" or TES for conveying curriculum content. About the same time, Dr. Octo Barnett's laboratory at the Massachusetts General Hospital began development of clinical simulations using the MUMPS language. Investigators at the University of Illinois developed a simulation model known as Computer Associated Simulation of the Clinical Encounter, or "CASE"). Research supported by the American Board of Internal Medicine demonstrated that a computerized examination system appeared feasible in professional evaluation/certification settings. Stevens and colleagues also demonstrated the feasibility of using computer-based systems for testing problem-solving ability in undergraduate medical school curriculum applications. Additionally, Sittig and colleagues examined the utility of computer-based instruction in teaching native users basic computer techniques such as "drag and drop" and other computer operations. These efforts suggest that computer-based testing techniques will similarly transport to the computer-native medical certification candidate.

Another system with special relevance to ABFP's efforts was developed at the University of Wisconsin. This project served as the nidus for the Computer-Based Examination (CBX) developed by the National Board of Medical Examiners (NBME). NBME's CBX development project has been in evolution for over a decade, and has demonstrated validity in examining professional degree candidates. The CBX development experience suggests that clinical computer simulations with automated scoring algorithms can produce professional certification examinations at reduced cost compared to traditional methods. However, the CBX model suffers from one major drawback: the clinical simulations are "hard-wired" in computer source code which must be re-coded for each new examination. Once the simulation has been used widely, the examination contents are no longer secure, necessitating continuous cycles of new simulation development.

To circumvent these weaknesses, ABFP embarked upon a computer-based testing project which will 1) generate new patient cases for each candidate examined, and 2) test a candidate's problem-solving ability. The system relies upon a knowledge base of family practice that represents in probabilistic terms disease/condition incidence, prevalence, evolution over time, and response to interventions.

Discussions with other certification organizations (other specialty boards, professional organizations) have emphasized the potential need and market for knowledge-based systems in training and evaluation contexts. The expert system literature affirms this evolution in evaluation and training systems. Early artificial intelligence/expert system work concentrated on "rules of thumb" or heuristics to represent problem-solving strategies identified by domain experts. Instances of these rule-based systems demonstrated that they were necessarily constrained to narrow domains, and that the knowledge contained in the rules was difficult to validate. Research has also indicated that experts relate only one dimension of knowledge when defining a rule, but also rely upon expansive knowledge of how systems work (i.e., physiology and pathophysiology in the medical domain) in performing real-world problem-solving. This realization has led to re-thinking regarding structure of knowledge-based systems to reflect the tasks such a system should accomplish, the methods the system should use to accomplish the tasks, and the knowledge required to support these methods.

Knowledge-acquisition for such systems entails development of a model for the domain and instantiation (ie, encoding and enter needed information into the system's data structure) of the model with information acquired from knowledge "donors". The model structure necessarily drives the knowledge acquisition effort. ABFP's computer based testing system under development at ATL while not an expert system per se, represents knowledge at multiple levels of complexity. For example, reactive airways disease is represented as a series of health states: Normal (Non-reactive) Airways, Reactive Airways-Mild, Reactive Airways-Moderate, and Reactive Airways-Severe. Each health state contains identifiers which relate the particular health state to precedents and antecedents (eg, Normal Airways serves as the precursor health state for Reactive Airways-Mild which precedes Reactive Airways-Moderate, which in turn leads to Reactive Airways-Severe.) Each health state in turn is associated with specific versions of universally observable findings. For example, a Finding called "Asthma Attack Frequency" is universally observable, although most people enjoy a Normal Airways health state and its associated frequency of asthma attacks of No Attacks (e.g. a Specific Finding indicating 0 attacks/month, indefinitely). Similarly, the Finding "Shortness of Breath" is instantiated with the Specific Finding "No shortness of breath" in the Normal Airways state. Likewise, other Findings such as Respiratory Function and Severe Asthma Attack Frequency are instantiated with corresponding normal Specific Findings (Normal Respiratory Functions, and No Severe Attacks.) This representation of Findings with Health State-specific instances of Specific Findings provides re-usable structure which transports to each new health state. Such reusability has been identified as a characteristic which contributes to the robustness of a knowledge-based system.

Another example will illustrate further the relationship between Findings and Specific Findings. Consider the growth curve charts we use in assessing child development. A Finding associated with growth is Height, a universal property of individuals. Normal Height would represent a Specific Finding which describes the range of heights associated with normal growth. Growth charts for Boys and Girls would then be described as Patterns which define the normal probability distributions for growth in boys and girls. At the start of a simulation, a percentile (e.g., 29th percentile) would be selected for the patient's growth characteristics. Then a Pattern for the particular patient is instantiated using the 29th percentile curve from the appropriate gender growth chart. How does the examinee learn about the patient's height? A Reveal Course of Action (COA) is initiated (the mechanics of this aren't important to understand at this point) to obtain the patient's current value for Height Finding.

Simmons and Davis have identified the importance of the distinction between actual knowledge and representation of knowledge. Knowledge describes the attributes of a health state; representation consists of the symbols and language used to encode the knowledge in the testing or expert system. Sinunons and Davis have additionally identified that knowledge of multiple types is needed for robust performance. These authors have partitioned knowledge into three fundamental types: knowledge about tasks, knowledge about methods, and knowledge about models of system behavior. These types correspond to those included in ATI's Computer based Testing system. Findings, Specific Findings, Patterns and Sub-pattens describe system behaviors and characteristics. Courses-of Action describe tasks and methods used to apply, modify, and evaluate the health state information and characteristics described in the model. As also indicated by Simmons and Davis, subdivision of knowledge types in this manner facilitates the knowledge acquisition process. This subdivision also promotes multiple levels of knowledge abstraction, which enhances the system's ability to represent varying levels of complexity. For example, in the Computer-based Testing system, a Pattern such as incidence is further subdivided into sub-pattens such as incidence in females versus males, and incidence in various racial/ethnic groups.

To facilitate development of such a system, the developers divided the system development task into three components: the knowledge base, the patient simulation generator, and the presentation system.

The knowledge base has been designed and represented as a series of entity-relationships. The model has several fundamental entities: Patient, Health States, Findings, Courses of Action (COA), and Agents. These entities have relationships of INTERACTS—WITH, CONTACTS, IS—RELATED, EXHIBITS, HAS, EXPOSED—TO, LEADS—TO, ASSOC—WITH, LINKS_TO, USES, IDENTIFY, MANAGE, ALTER, REVEAL, and EVALUATE.

Referring to FIG. 1, which describes the entities and relationships included in the model, rectangles indicate relationships between entities in the model. Hexagons indicate entities. Solid lines indicate Medical Knowledge Relationships (e.g., a course of action such as treatment with non-steroidal anti-inflammatory agents can modify Specific Findings such as pain in the patient with osteoarthritis). Dotted lines indicate Simulation/Evolution relationships which define how a particular domain simulation can proceed.

The model depicted in the figure has been published in the Journal of the American Board of Family Practice, and presented to national audiences.

The patient simulation generator relies upon a series of generation methods to create patients for presentation to the certification/recertification candidate. These algorithms function to evolve the patient forward (to reflect progression of the disease process and response to interventions) and backward in time (to create a past history for the patient.)

The patterns which describe patient progress and characteristics are defined as probability distributions (discrete and continuous as appropriate for particular finding) during the knowledge acquisition process. At the beginning of a simulation, a random number generator selects a master percentile" (MP) which then serves as the reference for selecting particular patterns from the appropriate specified distributions. Properties of these patterns are then presented to the candidate as findings for a particular health state (e.g., the current glucose level as a manifestation of diabetes.) Once presented with the patient description (age, race, gender, clinical findings), the candidate then selects appropriate COA's for further evaluation and/or management of the patient's health state.

Selection of an interventional COA disturbs the simulation in one or both of two ways. First, it may cause the simulated patient to change health states, e.g., by removing a appendix, the patient may proceed from a health state called "appendicitis" to one called "post appendectomy." Second, the intervention may initiate a pattern representing a temporary perturbation of some finding. For instance, administering acetaminophen to a febrile otitis media patient may not cause a change in health state—an infection may still exist, and the fever it induces will return in a few hours. Nevertheless, acetaminophen administration will reduce the fever for a short time. This perturbation might be represented in the knowledge base in the Temperature Finding, Fever Specific Finding, Antipyretic perturbation, with a four hour duration temperature change initiated by any antipyretic. When the examinee requests a temperature, the COA that reveals the current temperature must combine information about the underlying temperature and all antipyretic drugs administered in the last four hours.

The distinction between changing health states and perturbing findings is necessarily artificial (health states are just collections of findings), and the decision to model a particular process one way or another may often depend on testing goals, and subsequent decisions about how finely to model health states. In general, very fine distinctions between health states should result in more interventions that change health states, while coarsely defined health states may require more perturbations in Findings.

A COA can modify the health state in which a patient exists at one point in time. When the candidate selects such a COA, the simulated patient may evolve to a new health state on the basis of patterns specified for health state evolution in the knowledge base. The knowledge for a particular health domain is stored as a parallel health state network. For example, the initially generated patient for a case of osteoarthritis will demonstrate some stage of osteoarthritis. However, other health states such as obesity might influence the progress of the patient's arthritis from mild to moderate and moderate to severe disease. In the parallel networks of health states representation, a newly-generated patient will display findings consistent with a health state in the primary domain (for example, osteoarthritis) and in the parallel health states (e.g., obesity) which influence the primary health state's progress. As shown in the following figure, osteoarthritis can progress over time from the normal state to mild, moderate or severe osteoarthritis.

For this particular illness, progress occurs in one direction only; osteoarthritis doesn't regress once developed, but can stabilize at a particular degree of severity. Obesity represents a parallel health state which can influence the progression of osteoarthritis. Mild, moderate, and severe obesity can influence this progress at different rates: the model permits representation of greater impact for more severe obesity states. Notice also that obesity can regress (severe obesity can revert to moderate obesity, etc.) Similarly, other parallel health states might exist which could modify progression of osteoarthritis. For example, the patient who has osteoarthritis will frequently utilize nonsteroidal anti-inflammatory drugs (NSAID's) for treatment. These agents can improve the symptoms of osteoarthritis, but also impact on the parallel state of peptic ulcer disease, ie treatment with NSAID's can induce an ulcer, which will then evolve in parallel with the course and treatment of osteoarthritis. Initial experience with this representation indicates that these modifier-relationships are not well-defined in the medical literature and constitute a research area for further development.

The simulation system's fidelity depends upon access to a rich representation of health state-specific knowledge. This knowledge consists of Findings obtained from physician "knowledge-donors" working from templates provided by the Assessment Technologies, Inc. development team. The template includes a NAME for the health state and an associated SNOMED code. The template also includes specific descriptions of the Findings, and Patterns for these Findings. The patterns are stored as distributions; these distributions are obtained from the medical literature where available, and from physician expert opinion where such published data don't exist.

The development team doesn't expect the knowledge groups to provide these distributions but rather to indicate the relationships between health states, how parallel states influence each other qualitatively (e.g., increase, decrease, or stay the same), and possible sources of information about the relevant probabilities.

The knowledge model has evolved over the past six months to include extensive use of belief networks (also called Bayesian networks). Belief networks provide a graphical process for describing the relationships between entities in a health state. For example, some set of characteristics (family history, age, gender, racial origin/ethnicity, body weight) influence the development of impaired glucose tolerance.

Figure 24:
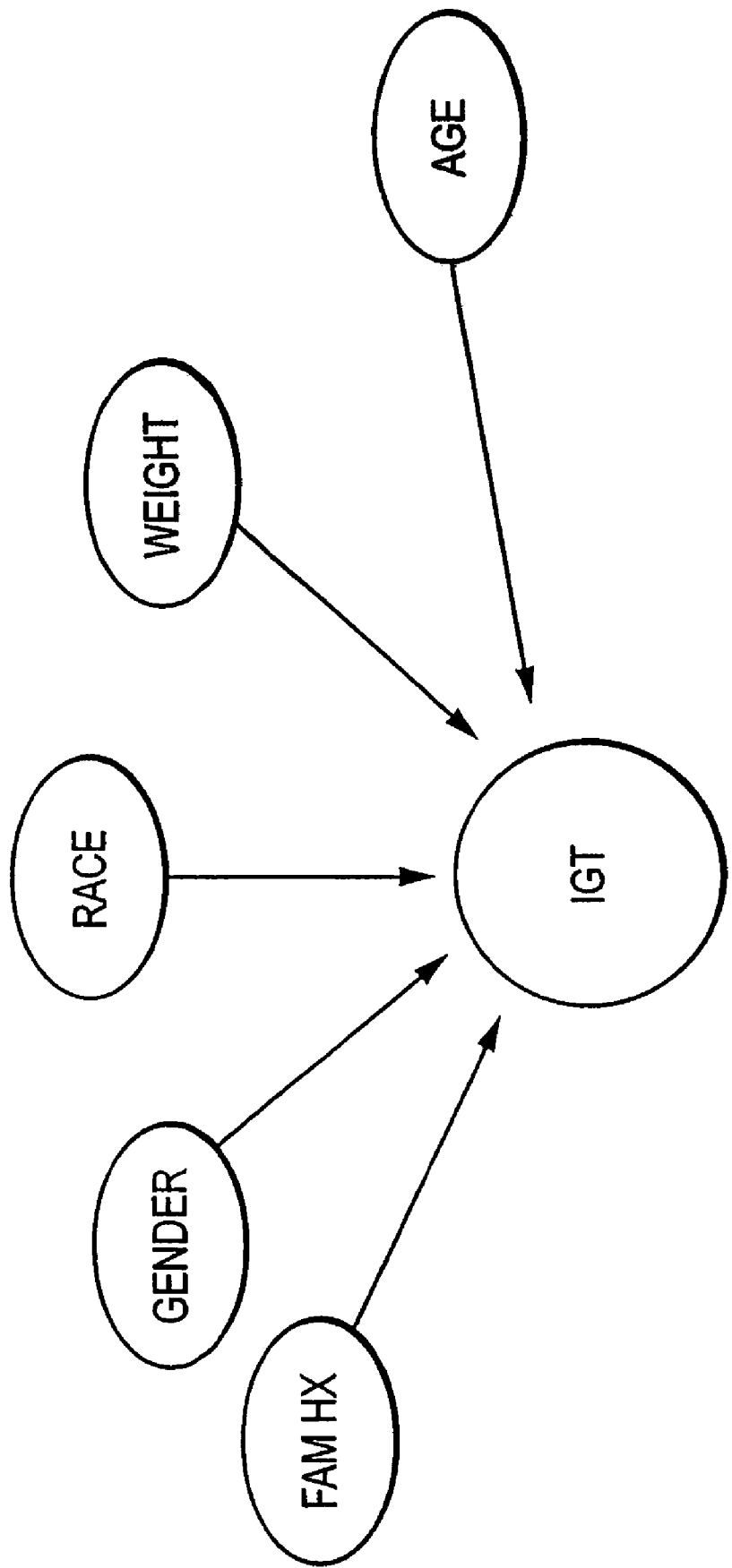
FIG. 24 is an illustration of an example showing the relationships between entities in a health state.

FIG. 24 illustrates these relationships: Family History, Gender, Race, Weight, and Age, all of which influence the development of impaired glucose tolerance. The raw pictorial doesn't say how they influence IGT, but rather that they "influence" the development of IGT. In the background, we incorporate probabilistic information which describes these relationships quantitatively, but would expect the knowledge development group to provide only semiquantitative guidance (e.g., a person whose mother has diabetes has twice the likelihood of developing IGT compared to an individual who has no such family history.) We intend to fill in the more specific quantitative probabilities on the basis of data in the literature where available; if such information does not exist, we will have to rely on expert opinion.

How the Knowledge Development Process Will Work

What will we need from the knowledge team in order to generate the information required in our system? The team should proceed in a step-wise fashion to address the following issues:
  How is the health state defined? (e.g., What criteria do we use to define the presence of impaired glucose tolerance or diabetes mellitus?)
  What population/s do/es the condition affect (should the system emphasize a particular population group?)
  What are the commonly accepted stages of the disease process? What demographic/patient characteristics, risk factors, and behaviors influence a patient's movement from one stage to another? (e.g., obesity's influence on hypertension and diabetes.)
  How do particular characteristics vary within a given stage of illness (e.g., what blood pressure ranges would we expect in Stage 1, 11, etc., for hypertension) How should these relationships appear in the Bayesian network format? What therapeutic modalities (pharmacologic, nonpharmacologic) exist to modify the progression and/or severity of the disease process? (e.g., magnitude of effect of weight loss on blood pressure in Stage I, Stage 11, etc; how much will weight loss lower blood pressure? How much will weight loss decrease the likelihood of progressing from Stage I to Stage 11 hypertension?)
  What guidelines exist to describe optimal management plans for the disease process (e.g., JNC VI for hypertension)
  For a given health state, what management and diagnostic concepts should we emphasize in creating the knowledge base (we cannot reproduce Harrison's in the knowledge base, nor should we—the system has to be good enough, not necessarily exhaustive)
  What parallel health states should the model reflect for the primary disorder in questions (e.g., for osteoarthritis, obesity and peptic ulcer disease might affect disease progress and treatment, respectively)
  What multimedia resources will we need to represent adequately the clinical findings associated with the health states?

How is the health state defined?
  The group should identify the criteria (physiologic, clinical, demographic, etc) which define the disease process, and which distinguish the various stages of the disorder. To whatever extent possible, we should rely on nationally accepted criteria as published in the peer-review literature and highly regarded textbooks.

What populations does the condition affect (should the system emphasize a Particular population group?)

We might encounter health states or diseases for which the ABFP wants to emphasize how the disorder affects certain groups. We will attempt to have one family physician ABFP director on each of the knowledge teams to provide the Board's perspective in this regard.

What are the commonly accepted states of the disease process?

The ABFP has used for many years the Disease Staging system produced by Systemetrics (originally developed at Jefferson Medical College). For disease processes which don't have commonly accepted staging criteria, we should use the Systemetrics system. However, for those disorders which have nationally accepted staging criteria, we should use those instead. For example, the INC VI has described the following stages for hypertension: Optimal, Normal, High-normal, Stage 1, Stage 2, and Stage 3.

What demographic/patient characteristics, risk factors, and behaviors influence a patient's movement from one stage to another? (e.g., obesity's influence on hypertension and diabetes)?

Issues such as age, gender, family history, body habitus, behaviors, occupational exposures, etc, affect the likelihood that an individual's disease will progress (or regress) from one stage to another. We will need information regarding 1) what are the important risk factors, 2) what is the magnitude of these factors' impact on the disorder's progress, and 3) what is the approximate time frame for these changes?

How do particular characteristics vary within a given stage of illness (e.g., what blood pressure ranges would we expect in stage I, II, etc., for hypertension)?

This relates to the stage descriptions alluded to above; however, individuals within a given disease stage will also exhibit some variability, ie patients within Stage I of hypertension will demonstrate a frequency distribution of systolic and diastolic blood pressures within the stage definition. These values might define normal distributions, uniform distributions, or some totally skewed dispersion. The group might not know the exact shape of these curves, but, to the extent possible, should indicate qualitatively what general configuration we should anticipate. Staff at A.T.I. will generate these distributions from literature sources.

How should these relationships appear in the Bayesian network format?

As noted earlier, the model uses Bayesian networks extensively to depict relationships, effects of therapy, progression of disease, choice of therapy, calculation of drug doses, and results of diagnostic testing. As the group identifies health states, the members should enumerate the demographic characteristics which influence state transitions, attributes which influence selection of therapy, etc. Each disease domain will include literally dozens of these structures. Although the team will not be expected to construct and develop fully each of these networks, the knowledge engineer will need guidance in what networks to develop. Again, we do not expect the team members to become facile in the creation of these networks; however, once developed, the team will have the opportunity to observe the behavior of these structures to confirm that they behave as intended.

What therapeutic modalities (pharmacologic, nonpharmacologic) exist to modify the progression and/or severity of the disease process? (e.g., magnitude of effect of weight loss on blood pressure in Stage I, Stage II. etc, how much will weight loss lower blood pressure? How much will weight loss decrease the likelihood of progressing from Stage I to Stage II hypertension?)

We will need information regarding optimal recommended therapies, pharmacologic and nonpharmacologic, which we would expect family physicians to employ in managing the particular health state. Additionally, we need some indication about how the therapy affects the disease process. For example, does weight loss decrease blood pressure, and by how much (large, moderate, small amount)?

What guidelines exist to describe optimal management plans for the disease process (e.g., JNC VI for hypertensions?

To whatever extent possible, we want the system to reflect well-done and broadly-accepted clinical guidelines. For some of the domains, no such documents exist and we will have to create our own "guideline" as we develop the health state. For others, such as hypertension, fairly extensive and accepted guidelines exist (e.g., JNC VI), and the system should reflect these guidelines as closely as possible. Also, we should attempt to utilize ABFP reference guides for those domains for which the Board has produced these documents.

For a given health state, what management and diagnostic concepts should we emphasize in creating the knowledge base (we can't reproduce Harrison's in the knowledge base, nor should we—the system has to be good enough, not necessarily exhaustive)?

We will attempt to include a family physician ABFP Board of Directors member on each team to provide Board input into health state emphases. In developing diabetes mellitus and osteoarthritis, we frequently find ourselves saying, "That's an issue for ABFP to decide." For example, in assessing a candidate's ability to manage osteoarthritis of the hand, do we want to investigate the candidate's ability to interpret a hand radiograph, or rather do we want to know how the candidate uses the information that a patient's x-ray demonstrates stigmata of osteoarthritis? The first question deals with a psychomotor skill (radiograph interpretation), while the second question assesses the candidate's cognitive knowledge regarding therapy for osteoarthritis. Having an ABFP Board member on each committee should help provide ABFP input into such decisions. Nevertheless, committee member input may be highly valuable to the Board, and we encourage members to contemplate these issues: What are the critical commissions and omissions in care plans for these patients? What are the simplest approaches to improving length and quality of life? What are the common mistakes in clinical care? What are the new insights into appropriate clinical care? What are likely to be the testable concepts related to this health state domain?

What parallel health states should the model reflect for the primary disorder in question?

For osteoarthritis, what other health conditions might influence the progress and/or management of the arthritis? For example, obesity certainly has an impact on the progress of osteoarthritis. Additionally, the presence of peptic ulcer disease will have a substantial impact on therapeutic options. Extended use of NSAID's could influence renal function. In this context, obesity, peptic ulcer disease, and renal function represent parallel health states: conditions which coexist and interact with osteoarthritis.

What multimedia resources will we need to represent adequately the clinical findings associated with the health staters?

One of the advantages of computer-based testing is the ability to present a variety of media to the candidate: sound, video, still-photographs and graphics can all enhance the system's appearance and provide the ability to assess psychomotor skills in real time. For each of the health states, what media should we acquire and how should we use these resources? For example, as we develop a module on heart failure, do we need third heart sounds and chest x-rays? Media represent a typical cost-effectiveness question in assessment: these resources cost substantial amounts. Does the information gained from presenting the media justify the acquisition cost? There's no easy answer to this, but we need to keep in mind that, for the most part, we will have to purchase a lot of this material. Obviously, we can use photographs currently in an item bank. Optionally, video and sounds come from external sources. Are there testable concepts that require a physical model to test in sufficient detail (performing a sigmoidoscopic examination, suturing) ?}

Further, as indicated herein, the present invention may be applied across a broad range of programming languages that utilize similar concepts as described herein. The present invention may also be used in a distributed environment/architecture, optionally using thin client technology.

FIG. 21 is an illustration of the architecture of the combined internet, POTS, and ADSL architecture for use in the present invention in accordance with another embodiment. In FIG. 21, to preserve POTS and to prevent a fault in the ADSL equipment 254, 256 from compromising analog voice traffic 226, 296 the voice part of the spectrum (the lowest 4 kHz) is optionally separated from the rest by a passive filter, called POTS splitter 258, 260. The rest of the available bandwidth—from about 10 kHz to 1 MHz—carries data at rates up to 6 bits per second for every hertz of bandwidth from data equipment 262, 264, 294. The ADSL equipment 256 then has access to a number of destinations including significantly the Internet 268, and other destinations 270, 272.

To exploit the higher frequencies, ADSL makes use of advanced modulation techniques, of which the best known is the discrete multitone (DMT) technology. As its name implies, ADSL transmits data asymmetrically—at different rates upstream toward the central office 252 and downstream toward the subscriber 250.

Cable television providers are providing analogous Internet service to PC users over their TV cable systems by means of special cable modems. Such modems are capable of transmitting up to 30 Mb/s over hybrid fiber/coas systems, which use fiber to bring signals to a neighborhood and coax to distribute it to individual subscribers.

Cable modems come in many forms. Most create a downstream data stream above 50 MHz (and most likely 550 MHz) and carve an upstream channel out of the 5-50-MHz band, which is currently unused. Using 64-state quadrature amplitude modulation (64 QAM), a downstream channel can realistically transmit about 30 Mb/s (the oft-quoted lower speed of 10 Mb/s refers to PC rates associated with Ethernet connections). Upstream rates differ considerably from vendor to vendor, but good hybrid fiber/coax systems can deliver upstream speeds of a few megabits per second. Thus, like ADSL, cable modems transmit much more information downstream than upstream.

The internet architecture 220 and ADSL architecture 254, 256 may also be combined with, for example, user networks 222, 224, and 228. As illustrated in this embodiment, users may access or use or participate in the administration, management computer assisted program in computer 240 via various different access methods. In this embodiment, the various databases 230, 232, 234, 236 and/or 238 are accessible via access to and/or by computer system 240, and or via internet/local area network 220. These databases may optionally include objective criteria for evaluating the corporate governance characteristics for ranking the corporation.

For example, environmental data is generally publicly available which indicates a corporation's compliance history, outstanding violations or potential violations, and the like. Similarly, standard legal and/or regulatory and/or administrative and/or business databases may be consulted to obtain additional information on corporate governance techniques, potential for government intervention, shareholder participation and/or customer loyalty. All this data may then be collected and analyzed to determine the overall attributes of the corporate, shareholder, government, and customer agents, for input into the simulation. Alternatively, the individual data may be used and input into the simulation, and the simulation may digest or process the data individually or collectively as part of the simulation.

In accordance with this embodiment, workstation 240 optionally includes modules 242, 246, 248, and 250 for individually handling the operations/simulation of the different agents. Alternatively, one module or a different number of modules may be used for processing the agent relationships, processes, and or interactions.

Alternatively, users may access or use or participate in the simulation program for decision making, indexing, ranking, and the like, via various different access methods as well. The above embodiments are only to be construed as examples of the various different types of computer systems that may be utilized in connection with the computer assisted and/or implemented process for decision making, indexing, ranking, with respect to corporate governance.

Of course, another result of the simulation is identifying companies for investment purposes, and actually investing in these companies. Further, the actual investments may be done manually and/or electronically, and optionally over the internet.

Figure 25:
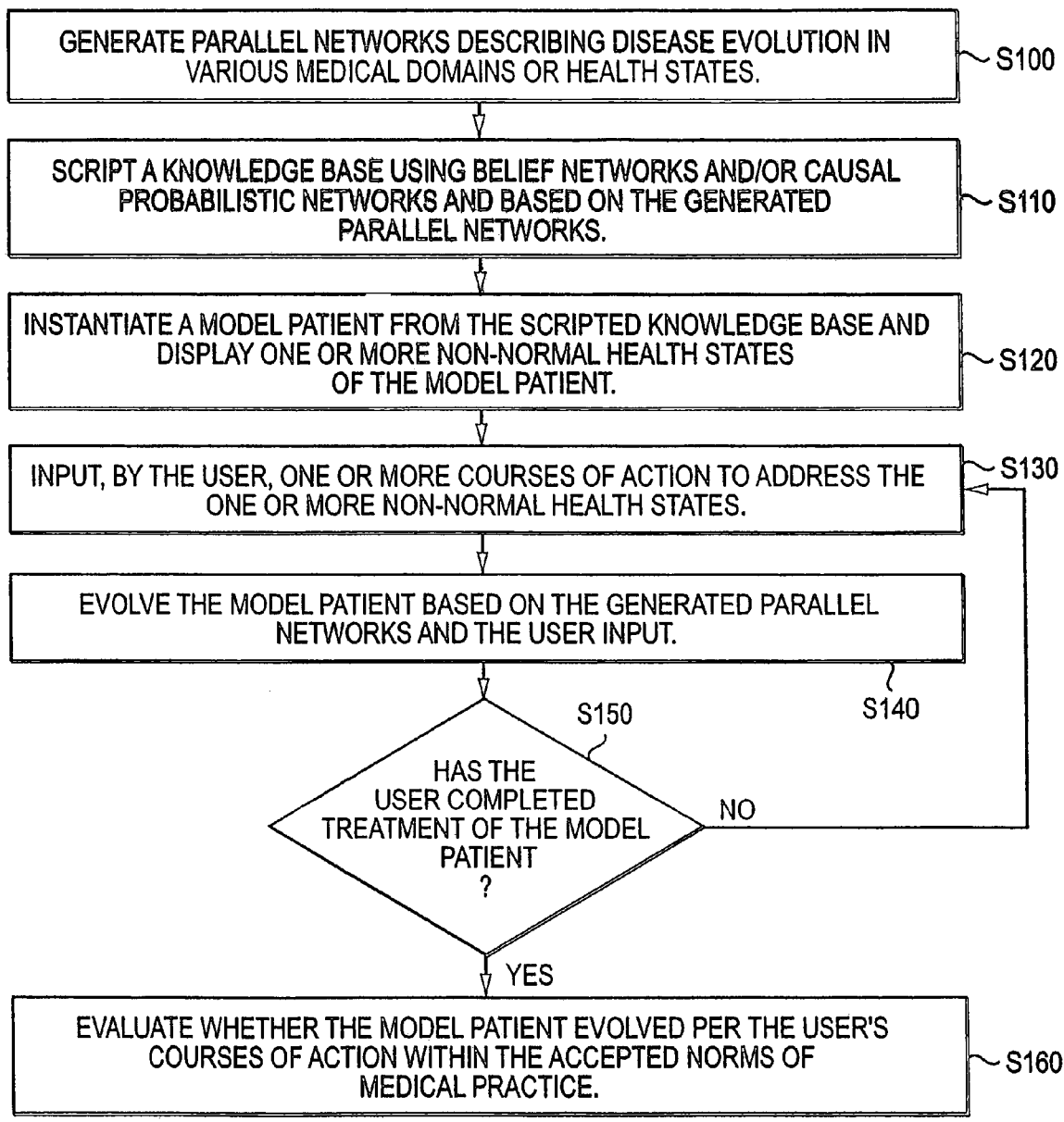
FIG. 25 is an illustrative flow chart outlining operation of an embodiment of the instant invention.

According to another embodiment, the instant invention includes a method for evaluating or educating a user, such as a physician, for example, as shown in FIG. 25. In Step S100, parallel health state networks, for example, describing disease evolution in various medical/domains or health states are generated by a computer or a user. In Step S110, a knowledge base is scripted by a user or a computer using belief networks and/or causal probabilistic networks, such as Bayesian networks, and based, at least in part, on the generated parallel health state networks. In step S120, the computer instantiates a model or virtual patient, at least in part, from the scripted knowledge base and displays to the user one or more non-normal health states of the model or virtual patient. In step S130, the user inputs one or more courses of action to address the one or more non-normal health states. Alternatively, the user inputs a query to the computer for a specific medical finding, for the patient such as would be obtained by running a medical test or examination on the patient. In such an event, the computer provides to the user the requested medical finding and returns to step S130. In step S140, the computer evolves the model or virtual patient based, at least in part, on the generated parallel health state networks and the user input. In step S150, the computer determines whether the user has completed treatment of te patient. if not, method flow returns to step S130. Otherwise, in step S160, the user's inputted courses of action and queries are evaluated relative to accepted norms of medical practice by the computer.

Figure 26:
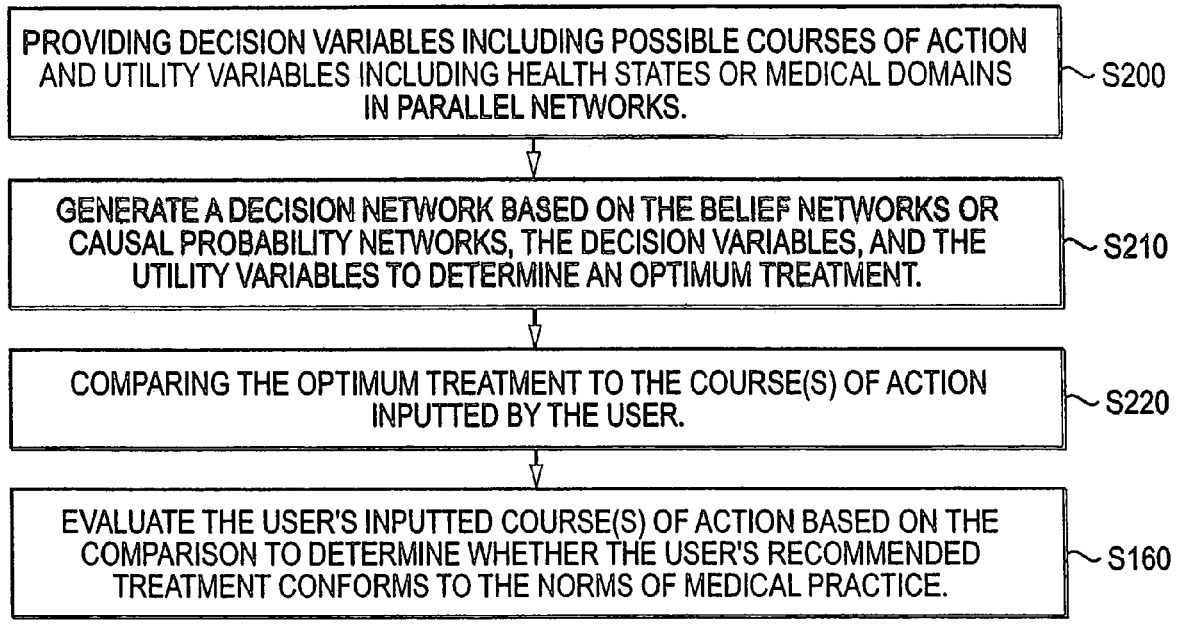
FIG. 26 is an illustrative flow chart showing operation of another embodiment of the instant invention.
Figure 27:
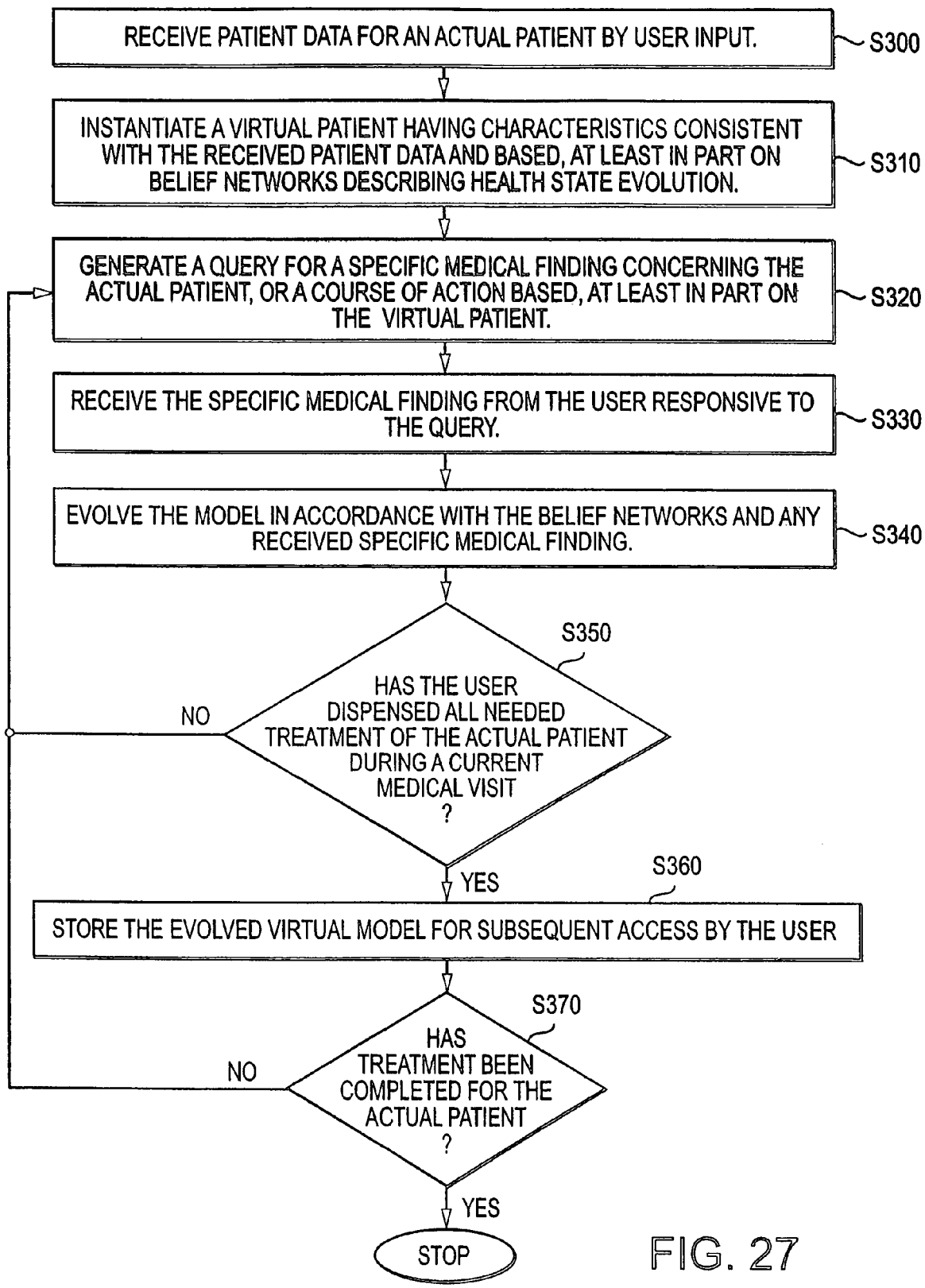
FIG. 27 is an illustrative flow chart showing operation of another embodiment of the instant invention.
Figure 28:
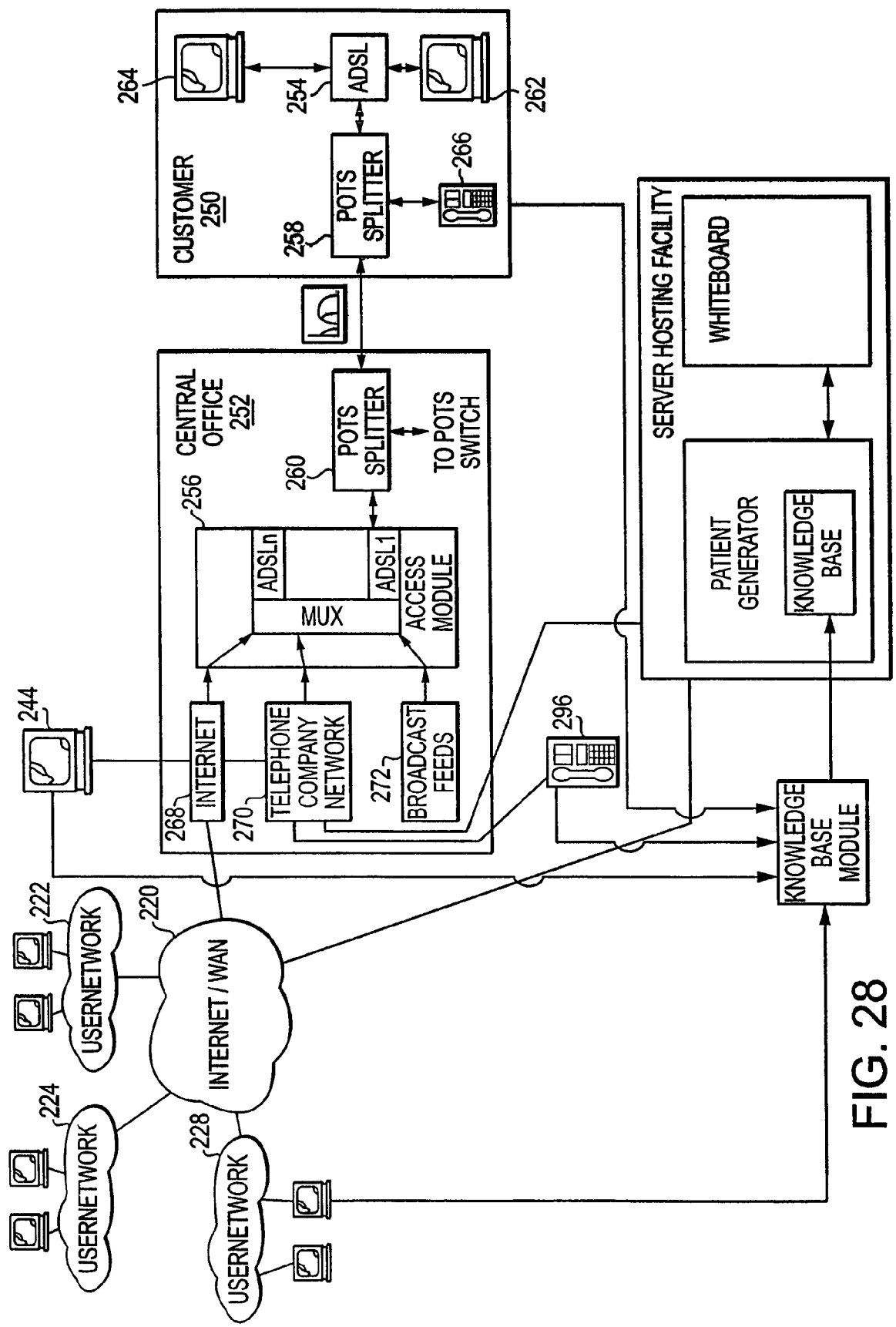
FIG. 28 is an illustration of a computer network architecture.

By way of example, FIG. 26 shows additional or alternative steps for evaluating a user. In step S200, decision variables, which can be controlled, such as courses of action, and utility variables, which are to be optimized, such as health states of medical domain in parallel networks are generated by a user or a computer. In step S210, a decision network based on the belief networks or causal probability networks, the decision variables, and the utility variables, is generated to determine an optimum treatment for the instantiated model or virtual patient. In step S220, the computer compares the generated optimum treatment with the courses of action and queries inputted by the user. The method flow then proceeds to step 150 as discussed above.

In another embodiment, the instant invention includes an expert system. By way of example, the expert system is a stand-alone unit. Alternatively, as shown by way of example in FIG. 21, the expert system is communicatable with a user via a computer network. The computer network includes, for example, POTS for a dial-up expert system and/or the Internet or WAN for a Web-accessible expert system.

In one embodiment of the expert system, the instant invention includes a program having instructions for executing the expert system. By way of example, in Instruction S300, the computer receives patient data for an actual by user input. In Instruction S310, the computer instantiates a virtual patient having characteristics consistent with the received patient data and based, at least in part, on one or more belief networks and/or causal probabilistic networks describing disease or health state evolution. In Instruction S320, the computer generates a query to the user for a specific medical finding concerning the actual patient, or a course of action based, at least in part, on the instantiated virtual patient and the one or more belief networks or causal probabilistic networks. In Instruction S330, the computer receives the specific medical finding from the user responsive to the generated query. In Instruction S340, the computer evolves the instantiated virtual patient in accordance with the above-mentioned belief networks and/or causal networks and the received specific medical finding and/or the generated course of action. In Instruction S350, the computer determines whether the user has dispensed complete treatment of the actual patient based, at least in part, on the generated courses of action, for example, for a given medical visit or encounter. If not, method flow is returned to Instruction S320. In Instruction S360, the computer stores the volved virtual model for subsequent access by the user. In Instruction S370, the computer and/or the user repeat Instructions S320-S370, for example, for each subsequent medical visit or encounter until treatment of the actual patient is completed.

In another embodiment, the instant invention includes a standard thin client or other standard client workstation that is programmably connected via a computer network to an expert system, such as described above. Alternatively, or in addition, the thin client or other standard client workstation is programmably connected via a computer network to an educational or testing system, such as described above.

In another embodiment, the instant invention includes a knowledge base module describing, for example, disease or health state evolution by way of belief networks or causal probabilistic networks, such as Bayesian networks. Advantageously, the knowledge base module enables a user or educator to update a knowledge base with current medical beliefs and practices. By way of example, earlier it was believed that ulcers were caused by certain foods and/or stress levels. Recent studies indicate that at least some ulcers are caused by bacteria, which should, of course, be treated by an appropriate antibiotic. Such a treatment would not have been recommended or accepted by a knowledge base that only reflected the earlier understanding of ulcers. As another example, advances in laboratory test or scanning, which become accepted in the general medical community, are advantageously included in the knowledge base module. For instance, such advances are included in reveal structures or management plan critiques, which are described using belief networks or causal probabilistic networks, such as Bayesian networks.

In another embodiment of the instant invention, the instant causal probabilistic expert systems have medical applications. An example of a medical application includes determining optimal antibiotic selections for an actual patient based at least in part on the patients clinical characteristics and one or more parallel causal probabilistic or belief networks describing health states. Another example of a medical application includes determining a specific chemotherapy regimen among several possible regimens for treating a cancer based, at least in part on, the patient's clinical characteristics and one or more parallel belief or causal probabilistic networks describing health states.

In an another embodiment of the instant invention, the instant causal probabilistic expert systems have non-medical applications. An example of a non-medical application includes determining credit worthiness for loan approval of an applicant in the financial industry based, at least in part, on the applicant's suitability characteristics and one or more parallel causal probabilistic or belief networks describing personal financial states. The personal financial states include financial states relative to balances and payment history, of for example, car loans, home mortgages, credit cards, student loans, business loans, total asset value, cash flow from one or more income sources, and total liabilities. Another example of a non-medical application includes determining optimal oil drilling sites based, at least in part, on one or more parallel causal probabilistic or belief networks describing one or more wildcatters' analysis for identifying potential sites for oil drilling.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed:

1. A method for educating or evaluating a user, comprising the steps of:

scripting a knowledge base responsive to a first plurality of health states;

instantiating a virtual patient for display to the user, the virtual patient including a plurality of health states;

receiving from the user at least one of a query for a medical finding concerning the instantiated virtual patient and a course of action; and at least one of:

generating, responsive to the received query, a specific medical finding at least in part from a first network defining a health state reveal structure corresponding to the instantiated virtual patient and optionally responsive to the knowledge base;

generating, responsive to the received query, an indication of an inappropriate query, based, at least in part, on a second network defining a medical practice management plan and optionally responsive to the knowledge base;

generating, responsive to the received course of action, an indication of an inappropriate course of action, based, at least in part, on the second network and optionally responsive to the knowledge base; and displaying to the user for at least one of education and evaluation the at least one of the specific medical finding, the inappropriate inquiry and the inappropriate course of action.

2. The method according to claim 1, wherein the medical practice management plan includes healthcare provider approved medical finding queries.

3. A computer system for evaluating or educating a user, compromising:
- a processor;
- a computer-readable medium storing instructions executable by said processor, said instructions including at least one of:
- generating a virtual patient based, at least in part, responsive to a description of a plurality of parallel health state networks and responsive to a scripted knowledge base characterizing a first plurality of health states;
- generating the virtual patient based, at least in part, responsive to a description of rates of progression within and/or between the plurality of parallel health state networks and responsive to a scripted knowledge base characterizing the first plurality of health states; and
- generating patient test data concerning the virtual patient, based, at least in part, using reveal structures to display of the patient test data and responsive to a scripted knowledge base characterizing the first plurality of health states; and
- wherein said method further includes the step of displaying to the user for at least one of education and evaluation the at least one of the specific medical finding, the inappropriate inquiry and the inappropriate course of action.

4. The computer system according to claim 3, wherein said computer system is communicatable with a user via a computer network.

5. A computer system for evaluating or educating a user, compromising:
- a processor;
- a computer-readable medium storing instructions executable by said processor, said instructions including at least one of;
- generating a virtual patient based, at least in part, based on a description of rates of progression within and/or between the plurality of parallel health state networks and responsive to a scripted knowledge base characterizing a first plurality of health states; and
- generating patient test data concerning the virtual patient, based, at least in part, on reveal structures to display of the patient test data and responsive to the scripted knowledge base characterizing the first plurality of health states.

6. The computer system according to claim 5, wherein said computer system is communicatable with a user via a computer network.

7. A computer system for evaluating or educating a user, compromising:
- a processor;
- a computer-readable medium storing instructions executable by said processor, said instructions including at least one of;
- generating a virtual patient based, at least in part, on at least one of a plurality of parallel health state networks and responsive to a scripted knowledge base characterizing a first plurality of health states;
- generating the virtual patient based, at least in part, on rates of progression within and/or between the at least one of the plurality of parallel health state networks and responsive to the scripted knowledge base characterizing the first plurality of health states; and
- generating patient test data concerning the virtual patient, based, at least in part, on reveal structures and responsive to the scripted knowledge base characterizing the first plurality of health states.

8. A computer readable medium including instructions being executed by a computer, the instructions instructing the computer to execute an educational or testing system for physicians, the instructions including:
- (a) accessing at least one representation, which describes at least one of a plurality of parallel health state networks;
- (b) scripting a knowledge base, at least in part, from the at least one representation; and
- (c) instantiating a model patient, at least in part, from the scripted knowledge base.

9. The computer readable medium according to claim 8, wherein the plurality of parallel health state networks describe at least one of a plurality of primary networks defining disease evolutions, a plurality of secondary networks defining risk factors affecting progression through a primary network of the plurality of primary networks, and a plurality of tertiary networks defining at least one of causal probabilistic medical complications attributed to at least one stage in the primary network and medical complications attributed to management of the at least one stage.

10. The computer readable medium according to claim 8, wherein the instructions further comprise:
- (d) accessing at least one second representation, which describes rates of progression within and/or between the plurality of parallel health state networks, and describes task factors that affect the rates of progression.

11. The computer readable medium according to claim 10, wherein the instructions further comprise:
- (e) accessing at least one third representation, which supports reveal structures to limit display of patient test data to patient test data specifically requested by the user.

12. The computer readable medium according to claim 11, wherein the instructions further comprise:
- (f) accessing at least one fourth representation which supports plan critiques of queries of and treatment prescribed by the user.

13. The computer readable medium according to claim 8, wherein the scripting step (b) includes scripting the knowledge base, at least in part, from the at least one second representation.

14. The computer readable medium according to claim 11, wherein the instructions further comprise:
- (g) receiving one of a course of action and a query for a specific medical finding concerning the model patient from the user responsive to the instantiated model patient; and
- (h) displaying, if the query is received, the specific medical finding to the user based at least in part on the at least one third representation, and repeating the step (g).

15. The computer readable medium according to claim 14, wherein the instructions further comprise:
- (i) evolving the model patient in accordance with the plurality of parallel health state networks and responsive to the received course of action.

16. The computer readable medium according to claim 14, wherein the instructions further comprise:
(j) repeating the steps (g) through (i) until the user has completed treatment of the model patient.

17. The computer readable medium according to claim 16, wherein instructions further comprise:
(k) generating a combination of treatment and queries based on the at least one fourth representation and the instantiated model patient; and
(l) evaluating the query and the treatment by the user in comparison to the generated optimum combination of treatment and queries.

18. A system for educating or evaluating a user comprising:
a model patient generator including a knowledge base scripted from at least one of at least one first network, which describes a plurality of parallel health state networks, and at least one second network, which describes at least one rate of progression within and/or between said plurality of parallel health state networks, and which describes at least one task factor that affects the at least one rate of progression; and
a display connected to the model patient generator user for educating and evaluating the user in response to at least one task factor.

19. The system according to claim 18, wherein said patient generator instantiating, upon user input, a model patient in a whiteboard, at least in part, from said scripted knowledge base.

20. The system according to claim 19, wherein said patient generator receives one of a course of action and a query for a specific medical finding concerning the model patient from the user responsive to the instantiated model patient, the whiteboard displaying, if the query is received, the specific medical finding to the user based, at least in part, on at least one third network, which describes at least one patient health state reveal structure, the whiteboard evolving the model patient in accordance with the plurality of parallel health state networks and responsive to the received course of action.

21. A knowledge base module for an educational or testing system or an expert system, comprising at least one of:
at least one first network, which describes each parallel health state network of a plurality of parallel health state networks and responsive to a scripted knowledge base characterizing a first plurality of health states;
at least one second network, which describes at least one rate of progression within and/or between said plurality of parallel health state networks, and which describes at least one task factor that affects the at least one rate of progression and responsive to the scripted knowledge base characterizing the first plurality of health states; and
at least one third network, which describes plan critiques including peer-accepted courses of action for addressing said plurality of parallel health state networks and responsive to the scripted knowledge base characterizing the first plurality of health states.

* * * * *